United States Patent
Miltich et al.

(12)

(10) Patent No.: US 6,402,793 B1
(45) Date of Patent: Jun. 11, 2002

(54) IMPLANTABLE MEDICAL DEVICE HAVING FLAT ELECTROLYTIC CAPACITOR WITH CATHODE/CASE ELECTRICAL CONNECTIONS

(75) Inventors: Thomas P. Miltich, Maple Grove; Paul A. Pignato, Stacy; Mark D. Breyen, Plymouth; Kurt J. Casby, Grant Township; William L. Johnson, Vadnais Heights, all of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/608,206

(22) Filed: Jun. 30, 2000

Related U.S. Application Data

(63) Continuation-in-part of application No. 09/103,876, filed on Jun. 24, 1998, now Pat. No. 6,141,205
(60) Provisional application No. 60/080,564, filed on Apr. 3, 1998.

(51) Int. Cl.[7] .......................... H01G 9/00; H01G 9/045; H01G 9/10; H01G 4/228; A61N 1/18
(52) U.S. Cl. ...................... 29/25.03; 361/509; 361/520; 361/522; 361/529; 361/538; 361/540; 361/541; 607/5
(58) Field of Search .............................. 29/25.01–25.03; 361/502, 508, 509, 512, 517, 519, 520, 522, 523, 529, 530–533, 535–539, 540, 541; 607/5

(56) References Cited

U.S. PATENT DOCUMENTS 3,398,333 A     8/1968   Zeppieri ..................... 317/230

(List continued on next page.)

OTHER PUBLICATIONS

P. Lunsmann et al, "High Energy Density Capacitors for Implantable Defibrillators," *DARTS–EUROPE: 10th Europe Passive Components Symposium.*, Oct. 7–11 1996, pp. 35–39.

(List continued on next page.)

*Primary Examiner*—Ha Tran Nguyen
(74) *Attorney, Agent, or Firm*—Girma Wolde-Michael

(57) ABSTRACT

Flat electrolytic capacitors particularly for use in implantable medical devices having stacked cathode and anode layers particular electrical connections of the capacitor anode and cathode layers with a capacitor connector assembly. Anode terminal means extend through the capacitor case side wall for electrically connecting a plurality of the anode tabs to one another and providing an anode connection terminal at the exterior of the case that is electrically insulated from the case. A cathode terminal extends through or to an encapsulation area of the capacitor case side wall via a cathode terminal passageway for electrically connecting a plurality of the cathode tabs to one another and providing a cathode connection terminal at the exterior of the case. The connector assembly is electrically attached to the anode connection terminal for making electrical connection with the anode tabs and to the cathode connection terminal for making electrical connection with the cathode tabs. The cathode terminal passageway comprises a cathode opening extending through the case wall, and the cathode terminal comprises a cathode wire or feedthrough pin extending from the gathered cathode tabs into or through the cathode opening providing the cathode connection terminal electrically connected with the case. Alternatively, the terminal passageway comprises a portion of an interior ledge of the side wall upper opening edge having a width and depth depressed below the upper opening edge and a cover edge portion overlying the ledge to trap the cathode terminal when the cover is welded to the crimped upper edge. The cathode terminal comprises a cathode tab extension foil attached to the gathered cathode tabs or an extension of one, a plurality or all of the cathode tabs.

14 Claims, 33 Drawing Sheets

U.S. PATENT DOCUMENTS

| | | | | |
|---|---|---|---|---|
| 3,555,369 | A | 1/1971 | Yoshino | 317/230 |
| 3,789,502 | A | 2/1974 | Callins et al. | 29/570 |
| 3,883,784 | A | 5/1975 | Peck et al. | 317/258 |
| 3,918,474 | A | 11/1975 | Supancic, Jr. | 141/98 |
| 3,993,939 | A | 11/1976 | Marien et al. | 317/230 |
| 4,004,199 | A | 1/1977 | Pearce et al. | 317/230 |
| 4,010,405 | A | 3/1977 | West | 361/433 |
| 4,065,636 | A | 12/1977 | Herczog | 174/52 S |
| 4,074,417 | A | 2/1978 | Pearce et al. | 29/570 |
| 4,183,600 | A | 1/1980 | Schroeder | 339/218 R |
| 4,254,775 | A | 3/1981 | Langer | 128/419 D |
| 4,352,714 | A | 10/1982 | Patterson et al. | 156/626 |
| 4,521,830 | A | 6/1985 | Aultiman et al. | 361/433 |
| 4,548,209 | A | 10/1985 | Wielders et al. | 128/419 D |
| 4,617,611 | A | 10/1986 | Miura et al. | 361/433 |
| 4,663,824 | A | 5/1987 | Kenmochi | 29/570 |
| 4,942,501 | A | 7/1990 | MacFarlane et al. | 361/523 |
| 4,987,519 | A | 1/1991 | Hutchins et al. | 361/518 |
| 5,086,374 | A | 2/1992 | MacFarlane et al. | 361/525 |
| 5,131,388 | A | 7/1992 | Pless et al. | 128/419 D |
| 5,146,391 | A | 9/1992 | MacFarlane et al. | 361/525 |
| 5,153,820 | A | 10/1992 | MacFarlane et al. | 361/525 |
| 5,370,663 | A | 12/1994 | Lin | 607/5 |
| 5,370,669 | A | 12/1994 | Daglow et al. | 607/36 |
| 5,380,341 | A | 1/1995 | Matthews et al. | 29/25.03 |
| 5,449,574 | A | 9/1995 | Highley | 429/152 |
| 5,522,851 | A | 6/1996 | Fayram | 607/5 |
| 5,545,184 | A | 8/1996 | Dougherty | 607/5 |
| 5,562,801 | A | 10/1996 | Nulty | 156/643.1 |
| 5,584,890 | A | 12/1996 | MacFarlane et al. | 29/25.03 |
| 5,591,540 | A | 1/1997 | Louie et al. | 429/163 |
| 5,621,607 | A | 4/1997 | Farahmandi et al. | 361/502 |
| 5,628,801 | A | 5/1997 | MacFarlane et al. | 29/25.03 |
| 5,660,737 | A | 8/1997 | Elias et al. | 216/6 |
| 5,737,181 | A | 4/1998 | Evans | 361/504 |
| 5,748,439 | A | 5/1998 | MacFarlane et al. | 361/525 |
| 5,749,911 | A | 5/1998 | Westlund | 607/36 |
| 5,801,917 | A | 9/1998 | Elias | 361/535 |
| 5,808,857 | A | 9/1998 | Stevens | 361/503 |
| 5,814,082 | A | 9/1998 | Fayram et al. | 607/5 |
| 5,814,091 | A | 9/1998 | Dahlberg et | 607/36 |
| 5,850,331 | A * | 12/1998 | Matsumoto et al. | 361/502 |
| 5,862,035 | A | 1/1999 | Farahmandi et al. | 361/502 |
| 5,908,151 | A | 6/1999 | Elias | 228/110.1 |
| 5,922,215 | A | 7/1999 | Pless et al. | 216/6 |
| 5,926,357 | A | 7/1999 | Elias et al. | 361/302 |
| 5,930,109 | A | 7/1999 | Fisher | 361/508 |
| 5,968,210 | A | 10/1999 | Strange et al. | 29/25.03 |
| 5,983,472 | A | 11/1999 | Fayram et al. | 29/25.42 |
| 6,191,931 | B1 * | 2/2001 | Paspa et al. | 361/302 |

OTHER PUBLICATIONS

Troup, "Implantable Cardioverters and Defibrillators," *Current Problems in Cardiology*, vol. XIV, No. 12, Dec. 1989, Year Book Medical Publishers, Chicago.

P. Lunsmann et al., "High Energy Density Capacitors for Implantable Defibrillators," *CARTS 96: 16th Capacitor and Resistor Technology Symposium.*, Mar. 11–15 1996, pp. 277–280.

* cited by examiner

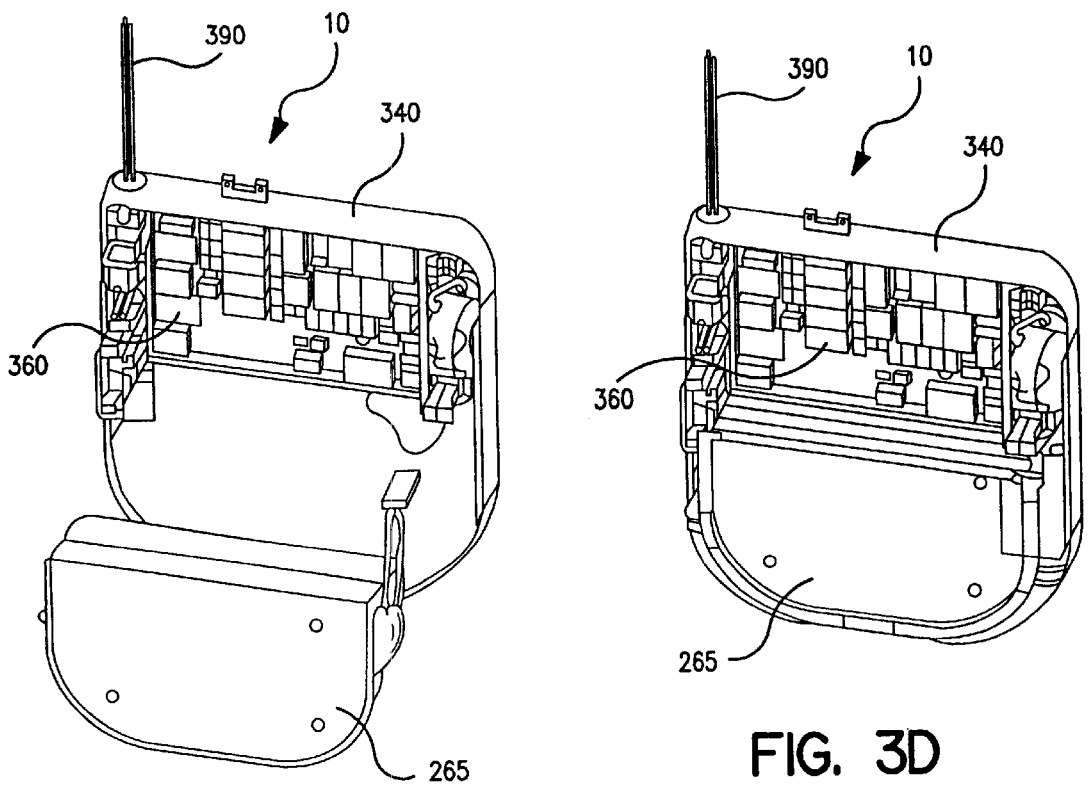
FIG. 3C
FIG. 3D
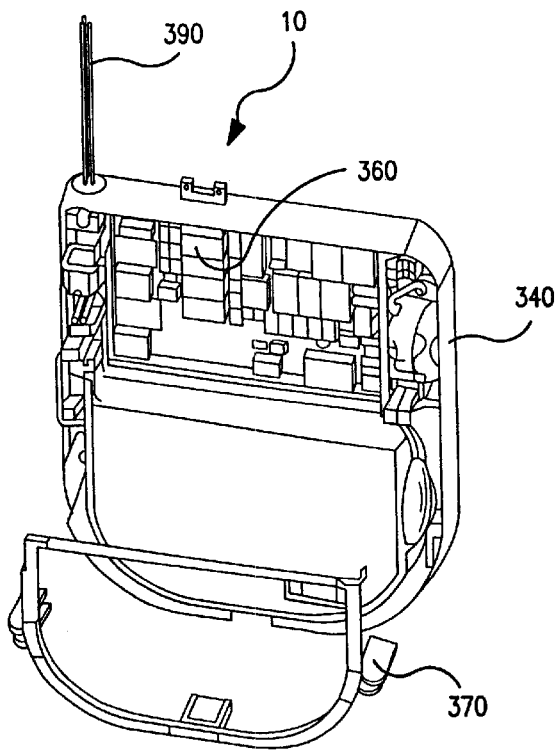
FIG. 3E

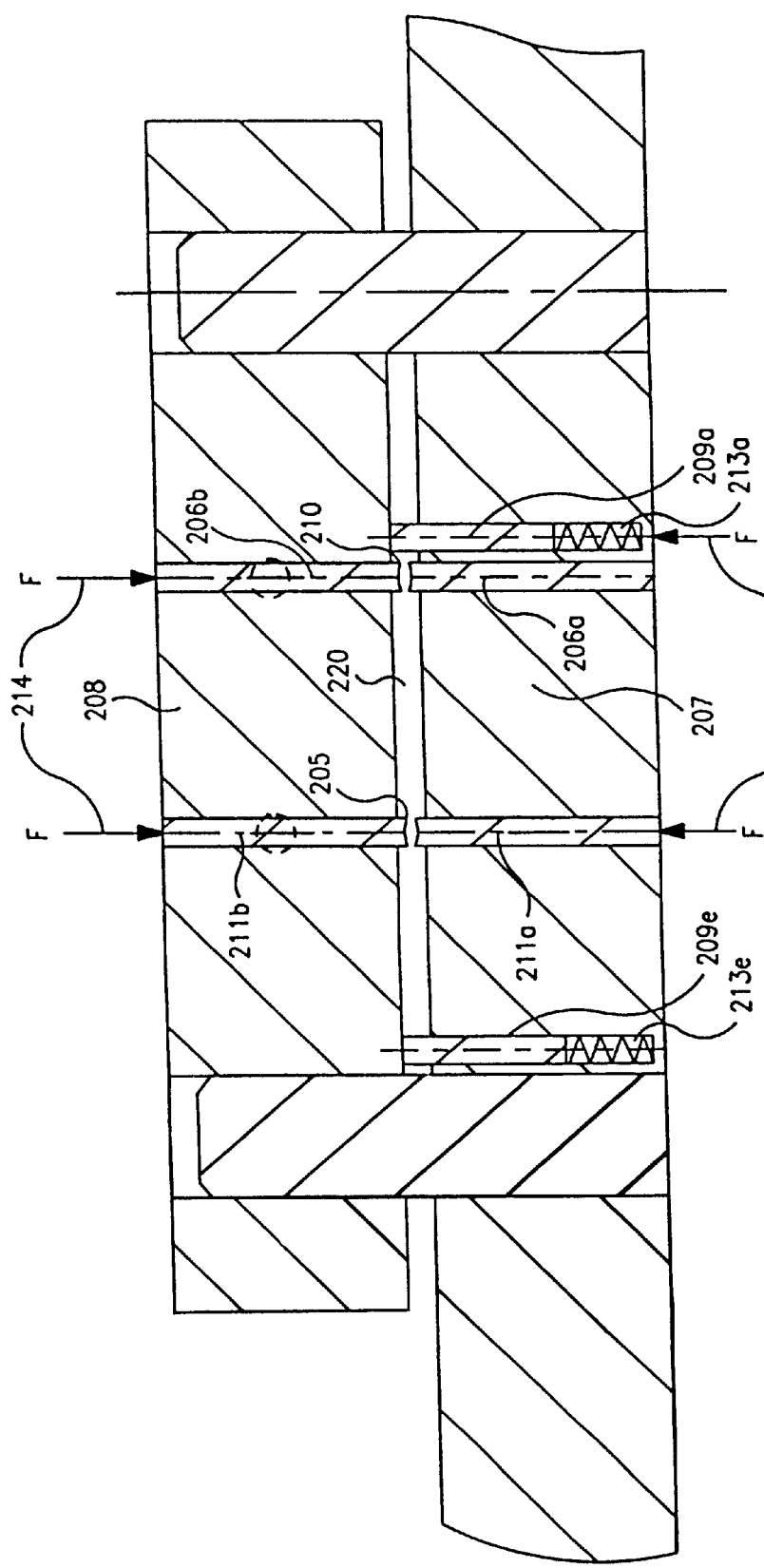

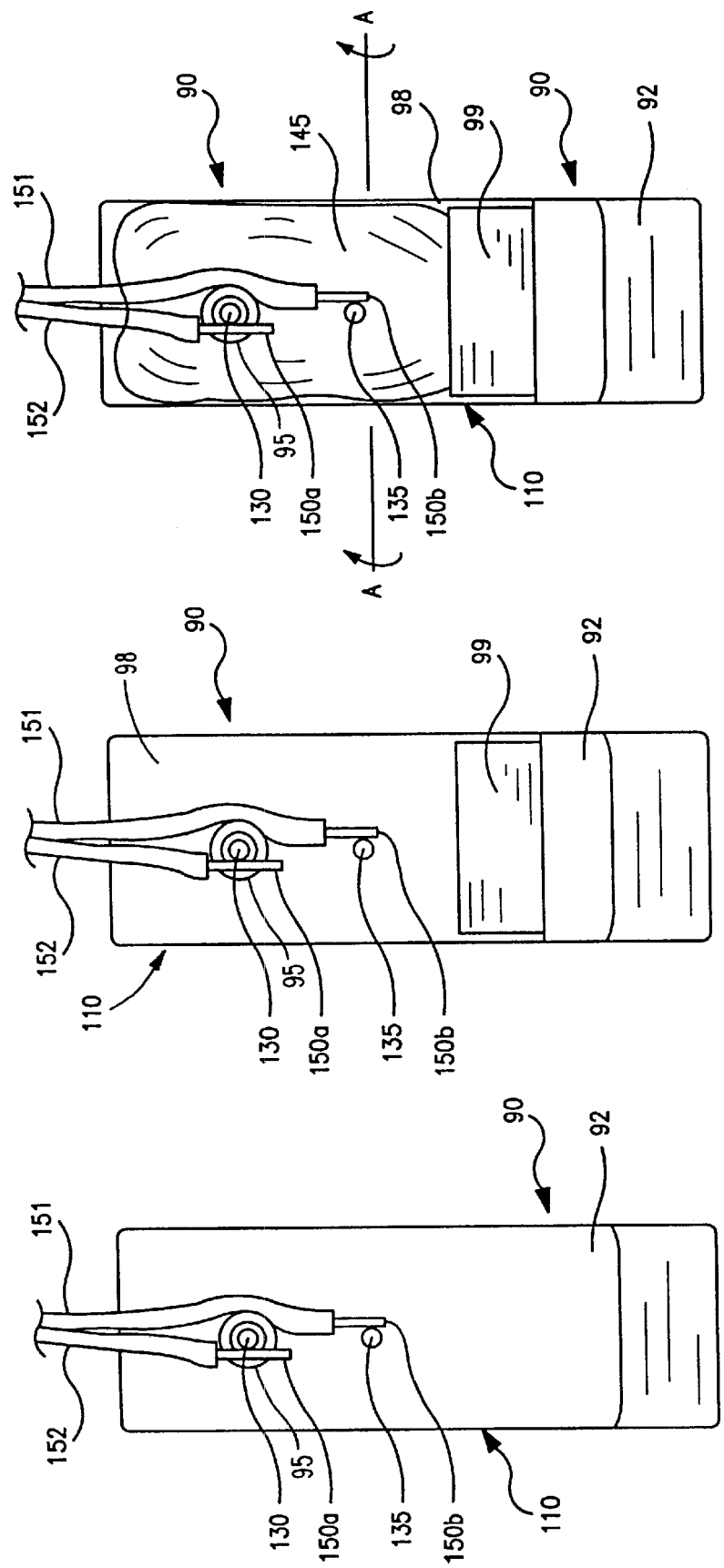

IMPLANTABLE MEDICAL DEVICE HAVING FLAT ELECTROLYTIC CAPACITOR WITH CATHODE/CASE ELECTRICAL CONNECTIONS

RELATED APPLICATION

This application claims priority and other benefits from U.S. Provisional Patent Application Serial No. 60/080,564, filed Apr. 3, 1998, entitled FLAT ALUMINUM ELECTROLYTIC CAPACITOR.

This application is a continuation-in-part of U.S. patent application Ser. No. 09/103,876 filed Jun. 24, 1998, now U.S. Pat. No. 6,141,205 in the names of Thomas M. Nutzman et al., and entitled IMPLANTABLE MEDICAL DEVICE HAVING FLAT ELECTROLYTIC CAPACITOR WITH CONSOLIDATED ELECTRODE TABS AND CORRESPONDING FEEDTHROUGHS.

FIELD OF THE INVENTION

This invention relates to implantable medical devices (IMDs) and their various components, including flat electrolytic capacitors for same coupled through lead wires to circuitry, the capacitors having stacked cathode and anode layers, and particularly electrical connections of the capacitor anode and cathode layers with the lead wires of a capacitor connector assembly.

BACKGROUND OF THE INVENTION

As described in the above-referenced parent application Ser. No. 103,876, and the provisional application that it claims priority from, a wide variety of IMDs are known in the art. Of particular interest are implantable cardioverter/defibrillators (ICDs) that deliver relatively high energy cardioversion and/or defibrillation shocks to a patient's heart when a malignant tachyarrhythmia, e.g., atrial or ventricular fibrillation, is detected. Current ICDs typically possess single or dual chamber pacing capabilities for treating specified chronic or episodic atrial and/or ventricular bradycardia and tachycardia and were referred to previously as pacemaker/cardioverter/defibrillators (PCDs). Earlier developed automatic implantable defibrillators (AIDs) did not have cardioversion or pacing capabilities. For purposes of the present invention ICDs are understood to encompass all such IMDs having at least high voltage cardioversion and/or defibrillation capabilities.

Generally speaking, it is necessary to employ a DC-DC converter within an ICD implantable pulse generator (IPG) to convert electrical energy from a low voltage, low current, electrochemical cell or battery enclosed within the IPG housing to a high voltage energy level stored in one or more high energy storage capacitor, as shown for example, in commonly assigned U.S. Pat. No. 4,548,209. The conversion is effected upon confirmation of a tachyarrhythmia by a DC-DC "flyback" converter which includes a transformer having a primary winding in series with the battery and a secondary winding in series with the high energy capacitor (s) and an interrupting circuit or switch in series with the primary coil and battery that is periodically opened and closed during a charging cycle. Charging of the high energy capacitor is accomplished by inducing a voltage in the primary winding of the transformer creating a magnetic field in the secondary winding when the switch is closed. The field collapses when the current in the primary winding is interrupted by opening the switch, and the collapsing field develops a current in the secondary winding which is applied to the high energy capacitor to charge it. The repeated interruption of the supply current charges the high energy capacitor to a desired level of several hundred volts over a charging time of the charge cycle. Then, the energy is rapidly discharged from the high voltage capacitor(s) through cardioversion/defibrillation electrodes coupled to the IPG through ICD leads and arranged about or in a heart chamber or vessel if the tachyarrhythmia is confirmed as continuing at the end of the charge time. The cardioversion/defibrillation shocks effected by discharge of such capacitors are typically in the range of about 25 to 40 Joules. The process of delivering cardioversion/defibrillation shocks in this way may be repeated if an earlier delivered cardioversion/defibrillation shock does not convert the tachyarrhythmia to a normal heart rhythm.

Energy, volume, thickness and mass are critical features in the design of ICD pulse generators that are coupled to the ICD leads. The battery(s) and high voltage capacitor(s) used to provide and accumulate the energy required for the cardioversion/defibrillation shocks have historically been relatively bulky and expensive. Presently, ICD IPGs typically have a volume of about 40 to about 60 cc, a thickness of about 13 mm to about 16 mm and a mass of approximately 100 grams.

It is desirable to reduce the volume, thickness and mass of such capacitors and ICD IPGs without reducing deliverable energy. Doing so is beneficial to patient comfort and minimizes complications due to erosion of tissue around the ICD IPG. Reductions in size of the capacitors may also allow for the balanced addition of volume to the battery, thereby increasing longevity of the ICD IPG, or balanced addition of new components, thereby adding functionality to the ICD IPG. It is also desirable to provide such ICD IPGs at low cost while retaining the highest level of performance. At the same time, reliability of the capacitors cannot be compromised.

Various types of flat and spiral-wound capacitors are known in the art, some examples of which are described as follows and/or may be found in the patents listed in Table 1 of the above-referenced parent patent application Ser. No. 09/103,876.

Prior art high voltage electrolytic capacitors used in ICDs have two or more anode and cathode layers (or "electrodes") and operate at room or body temperature. Typically, the capacitor is formed with a capacitor case enclosing an etched aluminum foil anode, an aluminum foil or film cathode, and a Kraft paper or fabric gauze spacer or separator impregnated with a solvent based liquid electrolyte interposed therebetween. A layer of aluminum oxide that functions as a dielectric layer is formed on the etched aluminum anode, preferably during passage of electrical current through the anode. The electrolyte comprises an ion producing salt that is dissolved in a solvent and provides ionic electrical conductivity between the cathode and the aluminum oxide dielectric. The energy of the capacitor is stored in the electrostatic field generated by opposing electrical charges separated by the aluminum oxide layer disposed on the surface of the anode and is proportional to the surface area of the aluminum anode. Thus, to minimize the overall volume of the capacitor one must maximize anode surface area per unit volume without increasing the capacitor's overall (i.e., external) dimensions. The separator material, anode and cathode layer terminals, internal packaging, electrical interconnections, and alignment features and cathode material further increase the thickness and volume of a capacitor. Consequently, these and other components in a capacitor and the desired capacitance limit the extent to which its physical dimensions may be reduced.

Some ICD IPGs employ commercial photoflash capacitors similar to those described by Troup in "Implantable Cardioverters and Defibrillators," Current Problems in Cardiology Volume XIV, Number 12, December 1989, Year Book Medical Publishers, Chicago, and as described in U.S. Pat. No. 4,254,775. The electrodes or anode and cathodes are wound into anode and cathode layers separated by separator layers of the spiral. Anode layers employed in such photoflash capacitors typically comprise one or two sheets of a high purity (99.99%), porous, highly etched, anodized aluminum foil. Cathode layers in such capacitors are formed of a non-porous, highly etched aluminum foil sheet which may be somewhat less pure (99.7%) respecting aluminum content than the anode layers. The separator formed of one or more sheet or layer of Kraft paper saturated and impregnated with a solvent based liquid electrolyte is located between adjacent anode and cathode layers. The anode foil thickness and cathode foil thickness are on the order of 100 micrometers and 20 micrometers, respectively. Most commercial photoflash capacitors contain a core of separator paper intended to prevent brittle, highly etched aluminum anode foils from fracturing during winding of the anode, cathode and separator layers into a coiled configuration. The cylindrical shape and paper core of commercial photoflash capacitors limits the volumetric packaging efficiency and thickness of an ICD IPG housing made using sane.

The aluminum anodes and cathodes of aluminum electrolytic capacitors generally each have at least one tab extending beyond their perimeters to facilitate electrical connection of all (or sets of) the anode and cathode layers electrically in parallel to form one or more capacitor and to make electrical connections to the exterior of the capacitor case. Tab terminal connections for a wound electrolytic capacitor are described in U.S. Pat. No. 4,663,824 that are laser welded to feedthrough pin terminals of feedthroughs extending through the case. Wound capacitors usually contain two or more tabs joined together by crimping or riveting.

Flat electrolytic capacitors have also been disclosed in the prior art for general applications as well as for use in ICDs. More recently developed ICD IPGs employ one or more flat high voltage capacitor to overcome some of the packaging and volume disadvantages associated with cylindrical photoflash capacitors. For example, U.S. Pat. No. 5,131,388 discloses a flat capacitor having a plurality of stacked capacitor layers. Each capacitor layer contains one or more anode foil sheet forming an anode layer having an anode tab, a cathode sheet or layer having a cathode tab and a separator for separating the anode layer from the cathode layer. In the '388 patent, the electrode stack assembly of stacked capacitor layers is encased within a non-conductive, polymer envelope that is sealed at its seams and fitted into a chamber of a conductive metal, capacitor case or into a compartment of the ICD IPG housing, and electrical connections with the capacitor anode(s) and cathode(s) are made through feedthroughs extending through the case or compartment wall. The tabs of the anode layers and the cathode layers of all of the capacitor layers of the stack are electrically connected in parallel to form a single capacitor or grouped to form a plurality of capacitors. The aluminum anode layer tabs are gathered together and electrically connected to a feedthrough pin of an anode feedthrough extending through the case or compartment wall. The aluminum cathode layer tabs are gathered together and electrically connected to a feedthrough pin of a cathode feedthrough extending through the case or compartment wall or connected to the electrically conductive capacitor case wall.

Many improvements in the design of flat aluminum electrolytic capacitors for use in ICD IPGs have been disclosed, e.g., those improvements described in "High Energy Density Capacitors for Implantable Defibrillators" presented by P. Lunsmann and D. MacFarlane at *CARTS 96: 16th Capacitor and Resistor Technology Symposium*Mar. 11–15, 1996, and at *CARTS-EUROPE96: 10th European Passive Components Symposium*. Oct. 7–11, 1996, pp. 35–39. Further features of flat electrolytic capacitors for use in ICD IPGs are disclosed in U.S. Pat. Nos. 4,942,501; 5,086,374; 5,146,391; 5,153,820; 5,562,801; 5,584,890; 5,628,801; and 5,748,439, all issued to MacFarlane et al.

A number of recent patents including U.S. Pat. No. 5,660,737 and U.S. Pat. Nos. 5,522,851; 5,801,917; 5,808, 857; 5,814,082; 5,908,151; 5,922,215; 5,926,357; 5,930, 109; 5,968,210 and 5,983,472, all assigned to the same assignee, disclose related flat electrolytic capacitor designs for use in ICDs. In several of these patents, internal alignment elements are employed as a means for controlling the relative edge spacing of the anode and cathode layers from the conductive capacitor case. In many of these patents, each anode layer and cathode layer is provided with an outwardly extending tab, and the anode and cathode tabs are electrically connected in common to a feedthrough pin and a step feature of the conductive capacitor case, respectively. The cathode tabs are gathered together against the step feature and ultrasonically welded together and to the step feature. In the '357 patent, the anode tabs are laser welded to one end of an aluminum ribbon that is ultrasonically welded at its other end to an aluminum layer that is ultrasonically welded to the terminal pin. The feedthrough terminal pin is electrically isolated from and extends outside and away from the case to provide an anode connection pin. A cathode connection pin is attached to the case and extends outwardly therefrom. The anode and cathode connection pins are electrically connected into the DC-DC converter circuitry, but the attachment mechanism is not described in any detail.

It is highly desirable to reduce the number of manufacturing steps and the number of parts required to make reliable electrical connections between the anode tabs and the anode feedthrough terminal pin and between the cathode tabs and the capacitor case or cathode feedthrough pin to reduce costs. It is also desirable that the space within the capacitor chamber required by these parts and the electrical connections be minimized so that capacitance can be maximized.

SUMMARY OF THE INVENTION

The present invention provides various cathode connections with a case of a case negative electrolytic capacitor that provides cathode connection terminals for attachment with a connector assembly, particularly to facilitate connection of the electrolytic capacitor with circuitry of an IMD.

In one embodiment, the capacitor comprises an electrode stack assembly and electrolyte are located within the interior case chamber of a hermetically sealed capacitor case. The electrode stack assembly comprises a plurality of capacitor layers stacked in registration upon one another, each capacitor layer comprising a cathode layer having a cathode tab, an anode sub-assembly comprising at least one anode layer having an anode tab, and a separator layer located between adjacent anode and cathode layers, whereby all adjacent cathode layers and anode layers of the stack are electrically insulated from one another by a separator layer.

Anode terminal means extend through the capacitor case side wall for electrically connecting a plurality of the anode tabs to one another and providing an anode connection terminal at the exterior of the case that is electrically insulated from the case. A cathode terminal extends through or to an encapsulation area of the capacitor case side wall via a cathode terminal passageway for electrically connecting a plurality of the cathode tabs to one another and providing a cathode connection terminal at the exterior of the case. A connector assembly is electrically attached to the anode connection terminal for making electrical connection with the anode tabs and to the cathode connection terminal for making electrical connection with the cathode tabs.

In certain embodiments, the cathode terminal passageway comprises a cathode opening extending through the case wall, and the cathode terminal comprises a cathode feedthrough pin extending through the cathode opening. A cathode feedthrough internal pin end is connected to the plurality of cathode tabs, and a cathode feedthrough external pin end extends away from the case to provide the cathode connection terminal.

In one variation, the cathode opening is hermetically welded with the cathode feedthrough pin extending through it providing the cathode connection terminal extending from the case. The exposed wire end of a cathode wire of the connector assembly is cross-wire welded to the side of cathode feedthrough wire at the cathode connection terminal.

In a further variation, the cathode opening is hermetically welded with the cathode feedthrough pin extending through it either before or after trimming or grinding the cathode feedthrough exterior pin end to be relatively flush with the exterior case wall. In this embodiment, the cathode connection terminal overlies the weld area on the exterior of the case wall. The exposed wire end of the cathode wire of the connector assembly is flush welded to the exterior of the case wall at the cathode connection terminal.

In further embodiments, the cathode terminal passageway comprises a location or section of the side wall upper opening edge having a width and depth depressed below the upper opening edge and a cover edge portion. The second cathode terminal end is trapped between the upper opening edge and the cover. The exposed wire end of the cathode wire of the connector assembly is flush welded to the exterior of the case wall at a defined cathode connection terminal.

In a first variation, the cathode terminal comprises a cathode tab extension foil of conductive material having a foil length extending between a first cathode terminal end thereof coupled with the plurality of cathode tabs and a second cathode terminal end thereof extending across the side wall upper edge opening. The second cathode terminal end of the cathode tab extension foil has a foil end width equal to or less than the step width and a foil end thickness about equal to the step depth. The second cathode terminal end extends across the side wall upper opening edge and is trapped therein by the cover hermetically sealed against the side wall upper opening edge and the foil surface at the second cathode terminal end. The cathode tab extension foil may be formed in a unitary manner as an extended one of the cathode tabs of the electrode stack assembly.

In a further variation, the cathode terminal comprises an extended length of a plurality or all of the gathered cathode tabs that extend to a second cathode terminal end. The extended tabs extend from the cathode layers across the side wall upper opening edge where the second cathode terminal ends of the extended cathode tabs are stacked. The cathode tab stack are trapped between a section of the side wall upper edge opening by the cover hermetically sealed against the side wall upper opening edge and the cathode tab stack. A mating section of the cover edge may be relieved to accommodate the thickness of stacked extended cathode tabs.

The connector block is preferably formed on an encapsulation area of the case side wall of epoxy that is cured for a period of time under elevated temperature conditions while rotating the capacitor assembly. The epoxy is applied in a liquid state, and the rotation and temperature causes the epoxy to flow into gaps of and to completely cover the anode and cathode terminal means and the electrical connections with the connector assembly, to drive air bubbles to the exposed surface, and to shape the exterior surface to a uniform, repeatable configuration.

BRIEF DESCRIPTION OF THE DRAWINGS

These and other advantages and features of the present invention will be appreciated as the same better understood by reference to the following detailed description of the preferred embodiment of the invention when considered in connection with the accompanying drawings, in which like numbered reference numbers designate like parts throughout the figures thereof, and wherein:

FIGS. 3(a)–3(g) are exploded perspective views of the manner in which the various components of the exemplary ICD IPG of FIGS. 1 and 2, including the electrolytic capacitors of the present invention, are disposed within the housing of the ICD IPG;

FIG. 5(c) is a cross-sectional view of the cold welding apparatus of FIGS. 5(a) and 5(b) in which anode layers of the electrode sub-assembly of FIG. 4 are cold-welded therein;

FIGS. 21(a)–21(c) are top views of the case negative capacitor assembly during the fabrication of the epoxy droplet connector block about the connection of the wiring harness and the anode and cathode feedthrough pins;

DETAILED DESCRIPTION OF THE PREFERRED EMBODIMENTS

Figure 1:
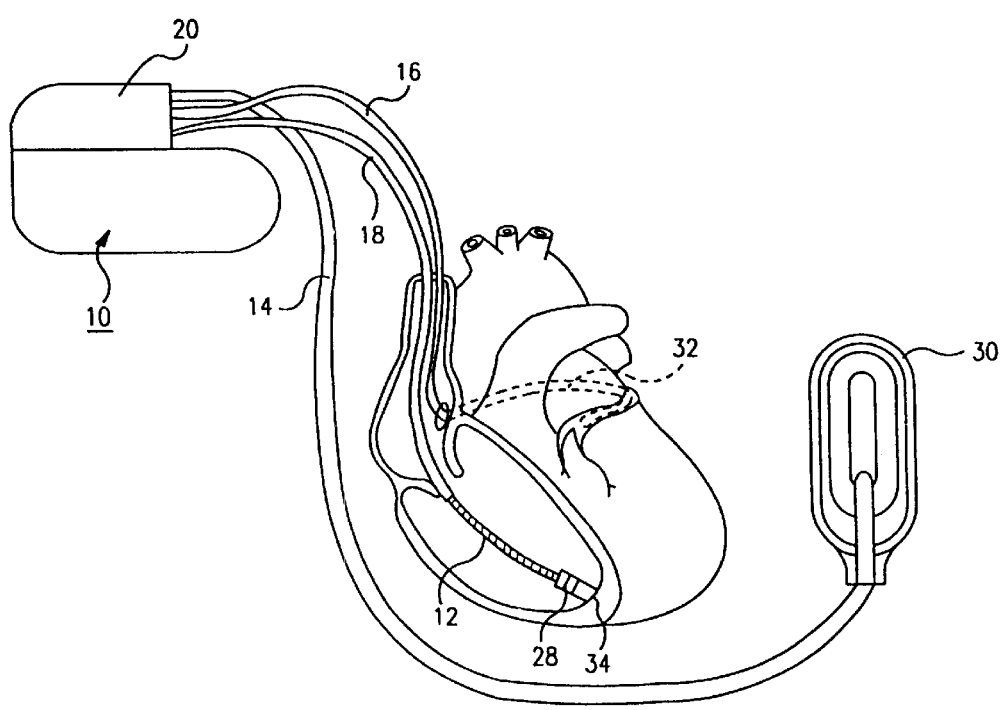
FIG. 1 illustrates the physical components of one exemplary embodiment of an ICD IPG and lead system in which the present invention may be advantageously incorporated.

FIG. 1 illustrates one embodiment of ICD IPG 10 in which the capacitor of the present invention is advantageously incorporated, the associated ICD electrical leads 14, 16 and 18, and their relationship to a human heart 12. The leads are coupled to ICD IPG 10 by means of multi-port connector block 20, which contains separate connector ports for each of the three leads illustrated. Lead 14 is coupled to subcutaneous electrode 30, which is intended to be mounted subcutaneously in the region of the left chest. Lead 16 is a coronary sinus lead employing an elongated coil electrode which is located in the coronary sinus and great vein region of the heart. The location of the electrode is illustrated in broken line format at 32, and extends around the heart from a point within the opening of the coronary sinus to a point in the vicinity of the left atrial appendage.

Lead 18 is provided with elongated electrode coil 28 which is located in the right ventricle of the heart. Lead 18 also includes stimulation electrode 34 which takes the form of a helical coil which is screwed into the myocardial tissue of the right ventricle. Lead 18 may also include one or more additional electrodes for near and far field electrogram sensing.

In the system illustrated, cardiac pacing pulses are delivered between helical electrode 34 and elongated electrode 28. Electrodes 28 and 34 are also employed to sense electrical signals indicative of ventricular contractions. As illustrated, it is anticipated that the right ventricular electrode 28 will serve as the common electrode during sequential and simultaneous pulse multiple electrode defibrillation regimens. For example, during a simultaneous pulse defibrillation regimen, pulses would simultaneously be delivered between electrode 28 and electrode 30 and between electrode 28 and electrode 32. During sequential pulse defibrillation, it is envisioned that pulses would be delivered sequentially between subcutaneous electrode 30 and electrode 28 and between coronary sinus electrode 32 and right ventricular electrode 28. Single pulse, two electrode defibrillation shock regimens may be also provided, typically between electrode 28 and coronary sinus electrode 32. Alternatively, single pulses may be delivered between electrodes 28 and 30. The particular interconnection of the electrodes to an ICD will depend somewhat on which specific single electrode pair defibrillation shock regimen is believed more likely to be employed.

Figure 2:
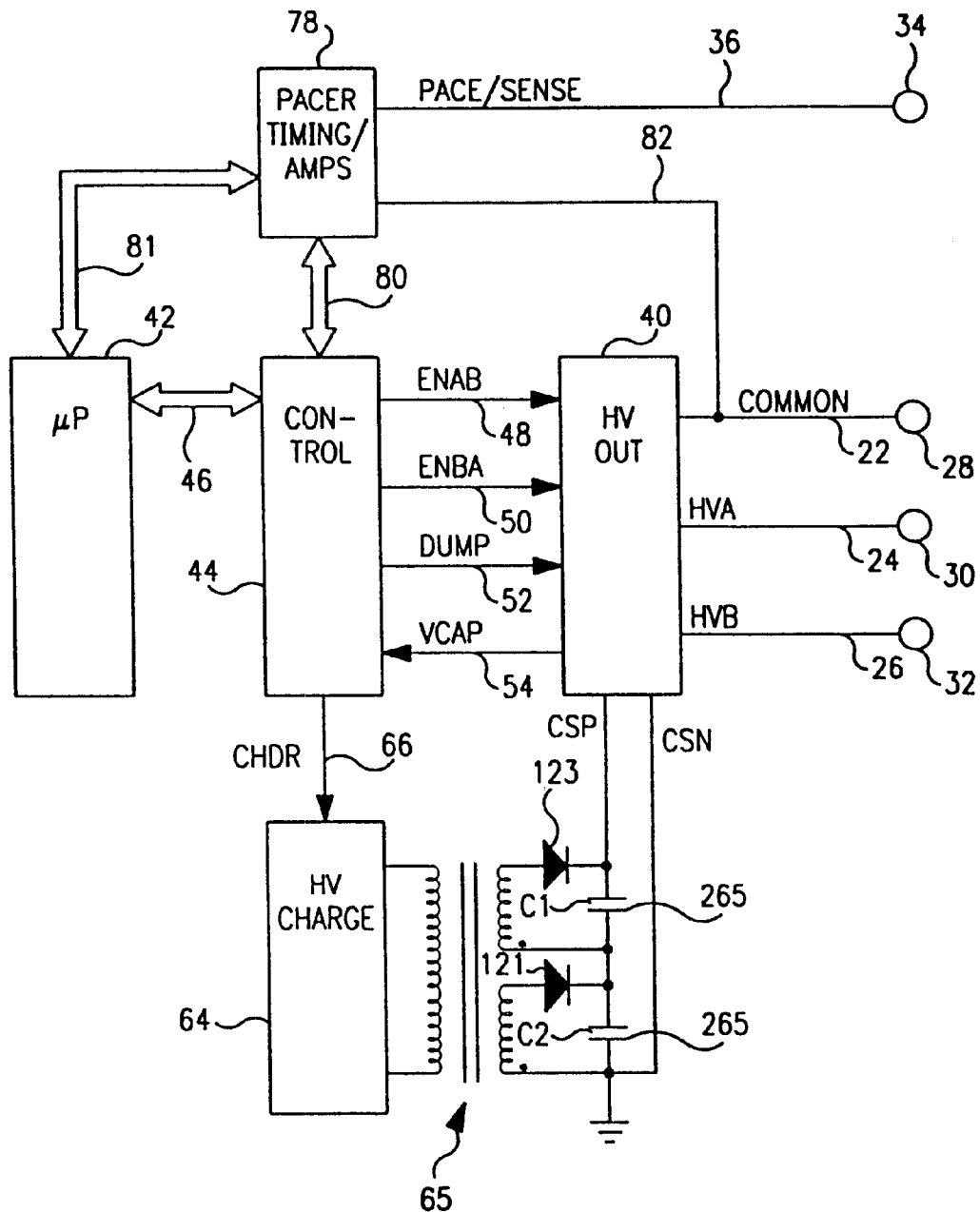
FIG. 2 is a simplified functional block diagram illustrating the interconnection of voltage conversion circuitry with the high voltage capacitors of the present invention with the primary functional components of one type of an ICD.

FIG. 2 is a block diagram illustrating the interconnection of high voltage output circuit 40, high voltage charging circuit 64 and capacitors 265 according to one example of the microcomputer based operating system of the ICD IPG of FIG. 1. As illustrated, the ICD operations are controlled by means of a stored program in microprocessor 42, which performs all necessary computational functions within the ICD. Microprocessor 42 is linked to control circuitry 44 by means of bi-directional data/control bus 46, and thereby controls operation of the output circuitry 40 and the high voltage charging circuitry 64. Pace/sense circuitry 78 awakens microprocessor 42 to perform any necessary mathematical calculations, to perform tachycardia and fibrillation detection procedures and to update the time intervals controlled by the timers in pace/sense circuitry 78 on reprogramming of the ICD operating modes or parameter values or on the occurrence of signals indicative of delivery of cardiac pacing pulses or of the occurrence of cardiac contractions,.

The basic operation and particular structure or components of the exemplary ICD of FIGS. 1 and 2 may correspond to any of the systems known in the art, and the present invention is not dependent upon any particular configuration thereof. The flat aluminum electrolytic capacitor of the present invention may be employed generally in conjunction with the various systems illustrated in the aforementioned '209 patent, or in conjunction with the various systems or components disclosed in the various U.S. patents listed in the above-referenced parent patent application Ser. No. 09/103,896.

Control circuitry 44 provides three signals of primary importance to output circuitry 40. Those signals include the first and second control signals discussed above, labeled here as ENAB, line 48, and ENBA, line 50. Also of importance is DMP line 52 which initiates discharge of the output capacitors and VCAP line 54 which provides a signal indicative of the voltage stored on the output capacitors C1, C2, to control circuitry 44. Defibrillation electrodes 28, 30 and 32 illustrated in FIG. 1, above, are shown coupled to output circuitry 40 by means of conductors 22, 24 and 26. For ease of understanding, those conductors are also labeled as "COMMON", "HVA" and "HVB". However, other configurations are also possible. For example, subcutaneous electrode 30 may be coupled to HVB conductor 26, to allow for a single pulse regimen to be delivered between electrodes 28 and 30. During a logic signal on ENAB, line 48, a cardioversion/defibrillation shock is delivered between electrode 30 and electrode 28. During a logic signal on ENBA, line 50, a cardioversion/defibrillation shock is delivered between electrode 32 and electrode 28.

The output circuitry includes a capacitor bank, including capacitors C1 and C2 and diodes 121 and 123, used for delivering defibrillation shocks to the electrodes. Alternatively, the capacitor bank may include a further set of capacitors as depicted in the above referenced '758 application. In FIG. 2, capacitors 265 are illustrated in conjunction with high voltage charging circuitry 64, controlled by the control/timing circuitry 44 by means of CHDR line 66. As illustrated, capacitors 265 are charged by means of a high frequency, high voltage transformer 65. Proper charging polarities are maintained by means of the diodes 121 and 123. VCAP line 54 provides a signal indicative of the voltage on the capacitor bank, and allows for control of the high voltage charging circuitry and for termination of the charging function when the measured voltage equals the programmed charging level.

Pace/sense circuitry 78 includes an R-wave sense amplifier and a pulse generator for generating cardiac pacing pulses, which may also correspond to any known cardiac pacemaker output circuitry and includes timing circuitry for defining ventricular pacing intervals, refractory intervals and blanking intervals, under control of microprocessor 42 via control/data bus 80.

Control signals triggering generation of cardiac pacing pulses by pace/sense circuitry 78 and signals indicative of the occurrence of R-waves, from pace/sense circuitry 78 are communicated to control circuitry 44 by means of a bi-directional data bus 81. Pace/sense circuitry 78 is coupled to helical electrode 34 illustrated in FIG. 1 by means of a conductor 36. Pace/sense circuitry 78 is also coupled to ventricular electrode 28, illustrated in FIG. 1, by means of a conductor 82, allowing for bipolar sensing of R-waves between electrodes 34 and 28 and for delivery of bipolar pacing pulses between electrodes 34 and 28, as discussed above.

FIGS. 3(a) through 3(g) show perspective views of various components of ICD IPG 10, including one embodiment of the capacitor of the present invention, as those components are placed successively within the housing of ICD IPG 10 formed by right and left hand shields 240 and 350.

Figure 3A:
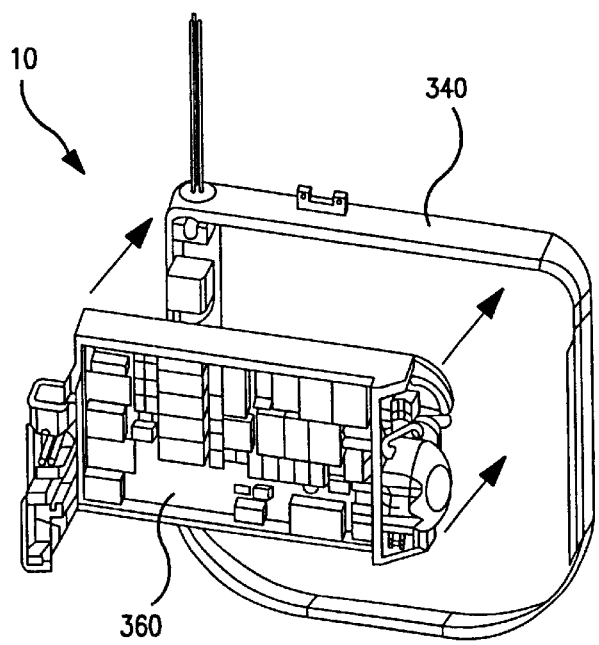
Figure 3B:
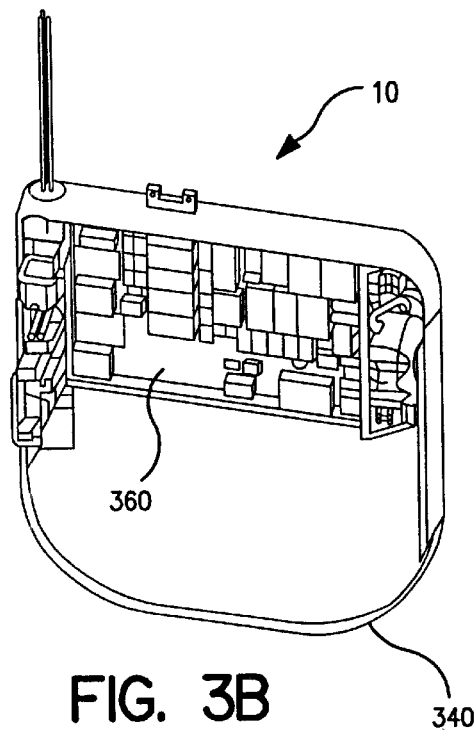

In FIG. 3(a), electronics module 360 is placed in right-hand shield 340 of ICD IPG 10. FIG. 3(b) shows ICD IPG 10 once electronics module 360 has been seated in right-hand shield 340.

FIG. 3(c) shows a pair of capacitors 265 formed as described herein prior to being placed within right-hand shield 340, the capacitors 265 being connected electrically in series by interconnections in electronics module 340. FIG. 3(d) shows ICD IPG 10 once the pair of capacitors 265 has been placed within right-hand shield 340. In accordance with one aspect of the present invention, the space occupied by the epoxy droplet connector block 145 and wire harness 155 of each stacked capacitor 265 within right-hand shield 340 is advantageously minimized. It will be understood that other shapes of capacitors 265 utilizing the improved connector block 145 and wiring harness 155 of the present invention can be inserted into the housing of ICD IPG 10 in the same or similar manner as described here.

Figure 3F:
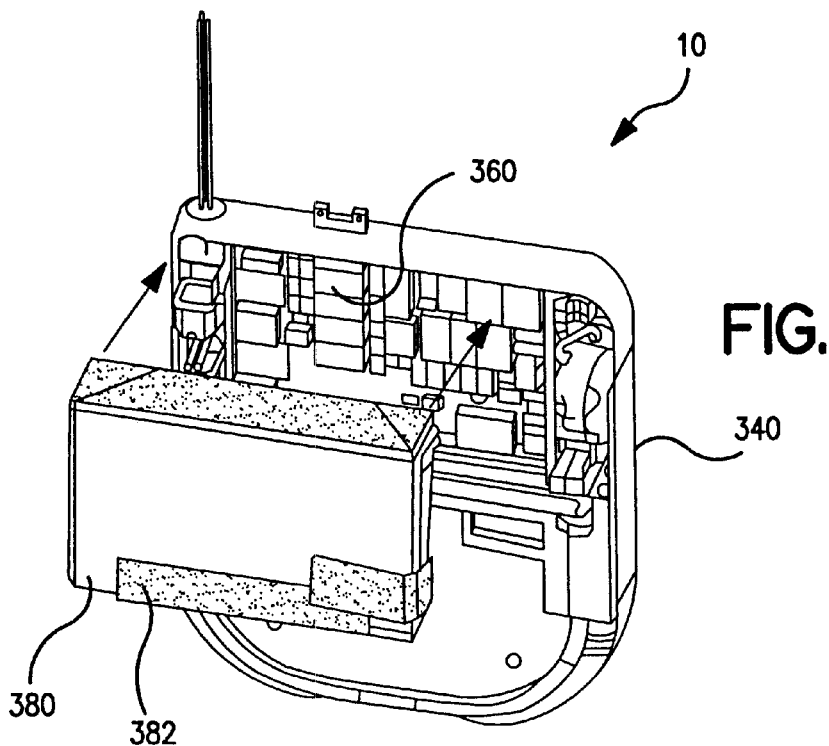

FIG. 3(e) shows insulator cup 370 prior to its placing atop capacitors 265 in right-hand shield 340. FIG. 3(f) shows electrochemical cell or battery 380 having insulator 382 disposed around battery 380 prior to placing it in shield 340. Battery 380 provides the electrical energy required to charge and re-charge capacitors 265, and also powers electronics module 360. Battery 380 may take any of the forms employed in the prior art to provide cardioversion/defibrillation energy, some of which are identified in parent patent application Ser. No. 09/103,876.

Figure 3G:
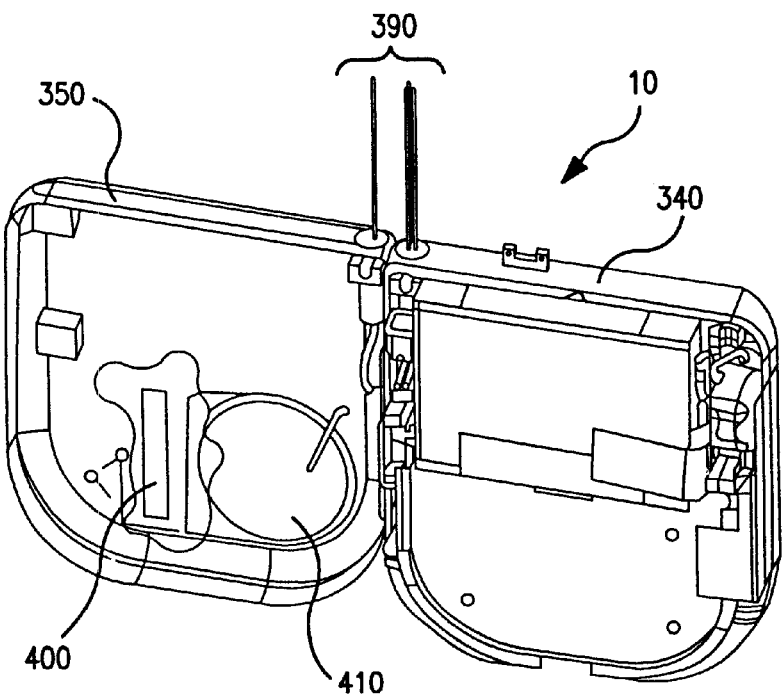

FIG. 3(g) shows ICD IPG 10 having left-hand shield 350 connected to right-hand shield 340 and feedthrough 390 projecting upwardly from both shield halves. Activity sensor 400 and patient alert apparatus 410 are shown disposed on the side lower portion of left-hand shield 350. Left-hand shield 350 and right-hand shield 340 are subsequently closed and hermetically sealed (not shown in the figures).

Figure 4:
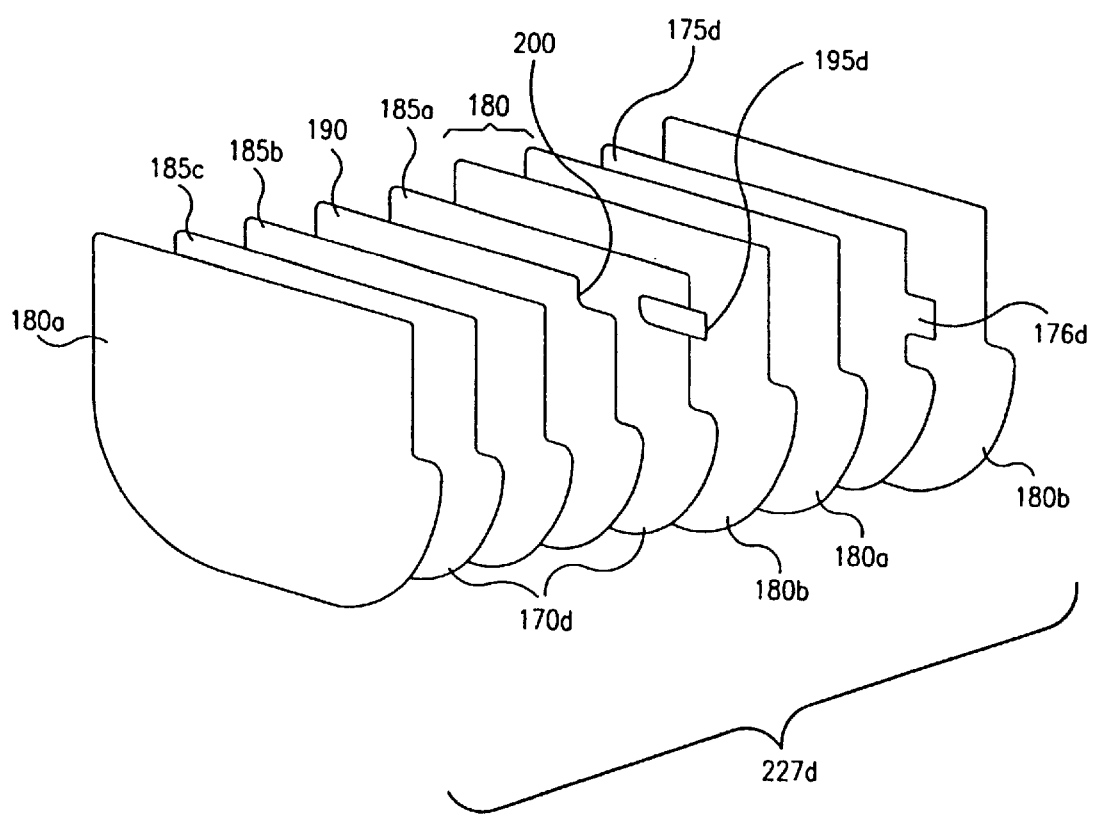
FIG. 4 is an exploded view of one embodiment of a single anode/cathode layer or electrode stack sub-assembly of an electrolytic capacitor incorporating the present invention.

FIG. 4 shows an exploded view of one embodiment of a capacitor layer or single anode/cathode sub-assembly 227 of capacitor 265. The capacitor design described herein employs a stacked configuration of a plurality of capacitor layers or single anode/cathode sub-assemblies 227 as further described below with respect to FIG. 6. Each anode/cathode sub-assembly 227 comprises alternating substantially rectangular-shaped anode layers 185 and cathode layers 175, with a substantially rectangular-shaped separator layer 180 being interposed therebetween. The shapes of anode layers 185, cathode layers 175 and separator layers 180 are primarily a matter of design choice, and are dictated largely by the shape or configuration of case 90 within which those layers are ultimately disposed. Anode layers 185, cathode layers 175 and separator layers 180 may assume any arbitrary shape to optimize packaging efficiency.

Anode sub-assembly 170d most preferably comprises a plurality of non-notched anode layers 185a, 185b, 185c, notched anode layer 190 including anode tab notch 200, and anode tab 195 coupled to anode layer 185a. It will be understood that anode sub-assembly 170d shown in FIG. 4 is but one possible embodiment of an anode sub-assembly 170. Cathode layer 175d most preferably is formed of a single sheet and has cathode tab 176 formed integral thereto and projecting from the periphery thereof.

In one preferred embodiment of the sub-assembly 227 as depicted in the figures, two individual separator layer sheets 180a and 180b form the separator layer 180 that is disposed between each anode sub-assembly 170 and cathode layer 175. Further single separator layer sheets 180a and 180b are disposed against the outer surfaces of the anode layer 185c and the cathode layer 175d. When the sub-assemblies are stacked, the outermost single separator layer sheets 180a and 180b bear against adjacent outermost single separator layer sheets 180b and 180a, respectively, of adjacent capacitor layers so that two sheet separator layers 180 separate all adjacent cathode and anode layers of an electrode stack assembly 225.

It will be understood by those skilled in the art that the precise number of sub-assemblies 227 selected for use in a electrode stack assembly 225 will depend upon the energy density, volume, voltage, current, energy output and other requirements placed upon capacitor 265. Similarly, it win be understood by those skilled in the art that the precise number of notched and un-notched anode layers 185, anode tabs 195, anode sub-assemblies 170, cathode layers 175 and separator layers 180 selected for use in a given embodiment of anode/cathode sub-assembly 227 will depend upon the energy density, volume, voltage, current, energy output and other requirements placed upon capacitor 265. It will now become apparent that a virtually unlimited number of combinations and permutations respecting the number of anode/cathode sub-assemblies 227, and the number of un-notched and notched anode layers 185 forming anode sub-assembly 170, anode sub-assemblies 170, anode tabs 195, cathode layers 175 and separator layers 180 disposed within each anode/cathode sub-assembly 227, may be selected according to the particular requirements of capacitor 265. Anode layers 185, cathode layers 175 and separator layers 180 are most preferably formed of materials typically used in high quality aluminum electrolytic capacitors.

Anode layers 185 and 190 are formed of anode foil that is most preferably through-etched, has a high specific capacitance (at least about 0.3, at least about 0.5 or most preferably at least about 0.8 microfarads/cm$^2$), has a dielectric withstand parameter of at least 425 Volts DC, a thickness ranging between about 50 and about 200 micrometers, more preferably between about 75 and 150 micrometers, more preferably yet between about 90 and about 125 micrometers, and most preferably being about 100 micrometers thick, and a cleanliness of about 1.0 mg/m$^2$ respecting projected area maximum chloride contamination. The anode foil preferably has a rated surge voltage of 390 Volts, an initial purity of about 99.99% aluminum, a final thickness of about 104 micrometers, plus or minus about five micrometers, and a specific capacitance of about 0.8 microfarads per square centimeter. Suitable anode foils are commercially available on a widespread basis.

Individual anode layers 185 are typically somewhat stiff and formed of high-purity aluminum processed by etching to achieve high capacitance per unit area. Thin anode foils are preferred, especially if they substantially maintain or increase specific capacitance while reducing the thickness of the electrode stack assembly 225, or maintain the thickness of electrode stack assembly 225 while increasing overall capacitance. For example, it is contemplated that individual anode layers 185 have a thickness of about 10 micrometers, about 20 micrometers, about 30 micrometers, about 40 micrometers, about 50 micrometers, about 60 micrometers, about 70 micrometers, about 80 micrometers, about 90 micrometers, about 100 micrometers, about 110 micrometers, about 120 micrometers, about 130 micrometers, about 140 micrometers and about 150 micrometers, Cathode layers 175 are preferably high purity and are comparatively flexible. Cathode layers 175 are most preferably formed from cathode foil having high surface area (i.e., highly etched cathode foil), high specific capacitance (preferably at least 200 microfarads/cm$^2$, and at least 250 microfarads/em$^2$ when fresh), a thickness of about 30 micrometers, a cleanliness of about 1.0 mg/m$^2$ respecting projected area maximum chloride contamination, and a purity which may be less than corresponding to the starting foil material from which anode foil is made. The cathode foil preferably has an initial purity of at least 99% aluminum, and more preferably yet of about 99.4% aluminum, a final thickness of about 30 micrometers, and an initial specific capacitance of about 250 microfarads per square centimeter. In other embodiments, cathode foil has a specific capacitance ranging between about 100 and about 500 microfarads/cm$^2$, about 200 and about 400 microfarads/cm$^2$, or about 250 and about 350 microfarads/cm$^2$, a thickness ranging between about 10 and about 150 micrometers, about 15 and about 100 micrometers, about 20 and about 50 micrometers, or about 25 and about 40 micrometers.

It is generally preferred that the specific capacitance of the cathode foil be as high as possible, and that cathode layer 175 be as thin as possible. For example, it is contemplated that individual cathode layers 175 have specific capacitances of about 100 microfarads/cm$^2$, about 200 microfarads/cm$^2$, about 300 microfarads/cm$^2$, about 400 microfarads/cm$^2$, about 500 microfarads/cm$^2$, about 600 microfarads/cm$^2$, about 700 microfarads/cm$^2$, about 800 microfarads/cm$^2$, about 900 microfarads/cm$^2$, or about 1,000 microfarads/cm$^2$. Suitable cathode foils are commercially available on a widespread basis. In still other embodiments, cathode foil is formed of materials or metals in addition to aluminum, aluminum alloys and "pure" aluminum.

Separator layer sheets 180a and 180b outer separator layers 165a and 165b are most preferably made from a roll or sheet of separator material. Separator layers 180 are preferably cut slightly larger than anode sub-assemblies 170 and cathode layers 175 to accommodate misaligmnent during the stacking of layers, to prevent subsequent shorting between anode and cathode layers, and to otherwise ensure that a physical barrier is disposed between the anodes and the cathodes of the finished capacitor.

It is preferred that separator layer sheets 180a and 180b and exterior separator layers 165a and 165b (shown in FIG. 9) be formed of a material that: (a) is chemically inert; (b) is chemically compatible with the selected electrolyte; (c) may be impregnated with the electrolyte to produce a low resistance path between adjoining anode and cathode layers, and (d) physically separates adjoining anode and cathode layers. In one preferred embodiment, separator material is a pure cellulose, very low halide or chloride content Kraft paper having a thickness of about 0.0005 inches (0.0013 mm), a density of about 1.06 grams/cm$^3$, a dielectric strength of 1,400 Volts AC per 0.001 inch (0.025 mn) thickness, and a low number of conducting paths (about 0.4/ft$^2$ or less). Separator layer sheets 180$a$ and 180$b$ and outer separator layers 165$a$ and 165$b$ may also be formed of materials other than Kraft paper, such as Manila paper, porous polymeric materials or fabric gauze materials. For example, porous polymeric materials may be disposed between anode and cathode layers like those disclosed in U.S. Pat. Nos. 3,555,369 and 3,883,784 in some embodiments of the capacitor layers In such capacitor stacks formed of a plurality of capacitor layers, a liquid electrolyte saturates or wets separator layers 180 and is disposed within case 90. It is to be understood, however, that various embodiments include within their scope a solid or adhesive electrolyte such as those disclosed in U.S. Pat. Nos. 5,628,801; 5,584,890; 4,942,501; 5,146,391 and 5,153,820. Note that an appropriate inter-electrode adhesives/electrolyte layer may be employed in place of paper, gauze or porous polymeric materials to form separator layer 180.

Continuing to refer to FIG. 4, a first preferred step in assembling a flat aluminum electrolytic capacitor is to cut anode layers 185 and 190, anode tabs 195, cathode layers 175 and separator layers 180. Those components are most preferably cut to shape using dies having low wall-to-wall clearance, where inter-wall spacing between the substantially vertically-oriented corresponding walls of the punch and die is most preferably on the order of about 6 millionths of an inch per side. Larger or smaller inter-wall spacings between the substantially vertically-oriented corresponding walls of the punch and cavity, such as about 2, about 4, about 5, about 7, about 8, about 10 and about 12 millionths of an inch may also be employed but are less preferred.

Such low clearance results in smooth, burr free edges being formed along the peripheries of anode layers 185 and 190, anode tabs 195, cathode layers 175 and separator layers 180. Smooth, burr free edges on the walls of the dies have been discovered to be critical respecting reliable performance of a capacitor. The presence of burrs along the peripheries of anode layers 185 and 190, anode tabs 195, cathode layers 175 and separator layers 180 may result in short circuit and failure of the capacitor. The means by which anode foil, cathode foil and separator materials are cut or formed may have a significant impact on the lack or presence of burrs and other cutting debris disposed about the peripheries of the formed or cut members. The use of low clearance dies produces an edge superior to the edge produced by other cutting methods, such as steel rule dies. The shape, flexibility and speed of a low clearance die have been discovered to be superior to those achieved by laser or blade cutting. Other methods of cutting or forming anode layers 185 and 190, anode tabs 195, cathode layers 175 and separator layers 180 include, but are not limited to, steel rule die cutting, laser cutting, water jet cutting and blade cutting.

The preferred low clearance of the die apparatus is especially important for cutting thin ductile materials such as the cathode foil. In addition to improving reliability, burr and debris reduction permits reductions in the thickness of separator layer 180, thereby improving energy density of the capacitor. Angle cutting, where the face of the punch is not held parallel to the opposing floor of the die during the cutting step, is another less preferred method of cutting or forming anode layers 185 and 190, anode tabs 195, cathode layers 175 and separator layers 180.

It is preferred to cut or otherwise form separator layer 180 such that its outer periphery conforms closely to that of the corresponding side walls of the interior of case 90. In preferred embodiments, the periphery of separator layer is disposed within plus or minus 0.009 inches of the corresponding side walls of case 90. Such close conformity between the periphery of separator layer 180 and the corresponding internal side walls of case 90 has been discovered to provide the advantage of permitting separator layers 180 to immobilize or secure firmly in place electrode stack assembly 225 in case 90. This immobilization occurs because the separator paper forming separator layers 180 swells after electrolyte is added through the lumen of fill port 107 into otherwise assembled and sealed capacitor 265.

In a preferred method, foil or separator materials are drawn between the punch and cavity portions of a die having appropriate clearances on a roll. An air or hydraulically actuated press is then most preferably employed to actuate the punch or cavity portion of the die. The punch portion of the die is most preferably formed of hardened tool steel, or has other suitable wear resistant materials or coatings disposed on the cutting surfaces thereof When the cavity of the die is aligned vertically, the punch portion of the die may travel either upwards or downwards towards the die cavity during a cutting cycle. In the former case, components are cut and drop downwardly into a container for use in subsequent assembly operations. In the latter case, components are cut and may be presented directly to automated assembly equipment, such as robots equipped with vacuum or other pick-up tooling, for subsequent processing. Low clearance dies of the type described herein may be supplied by Top Tool, Inc. of Minneapolis, Minn.

Anode sub-assembly 170 most preferably includes one notched anode layer 190, which facilitates appropriate placing and positioning of anode tab 195 within anode sub-assembly 170. More than one notched anode layer 190 may also be included in anode sub-assembly 170. It is preferred that the remaining anode layers of anode sub-assembly 170 be non-notched anode layers 185. Anode tab 195 is most preferably formed of aluminum strip material. In one preferred embodiment, the aluminum strip has a purity of about 99.99% aluminum and a lesser degree of anodization than the anode foil or sheet. When anode tab 195 is formed of a non-anodized material, cold welding of anode tab 195 to non-notched anode layers 185 may be accomplished with less force and deflection, more about which we say below. It is preferred that the thickness of anode tab 195 be about equal to that of notched anode layer 190. If more than one notched anode layer 190 is employed in anode sub-assembly 170, a thicker anode tab 195 may be employed.

Figure 13:
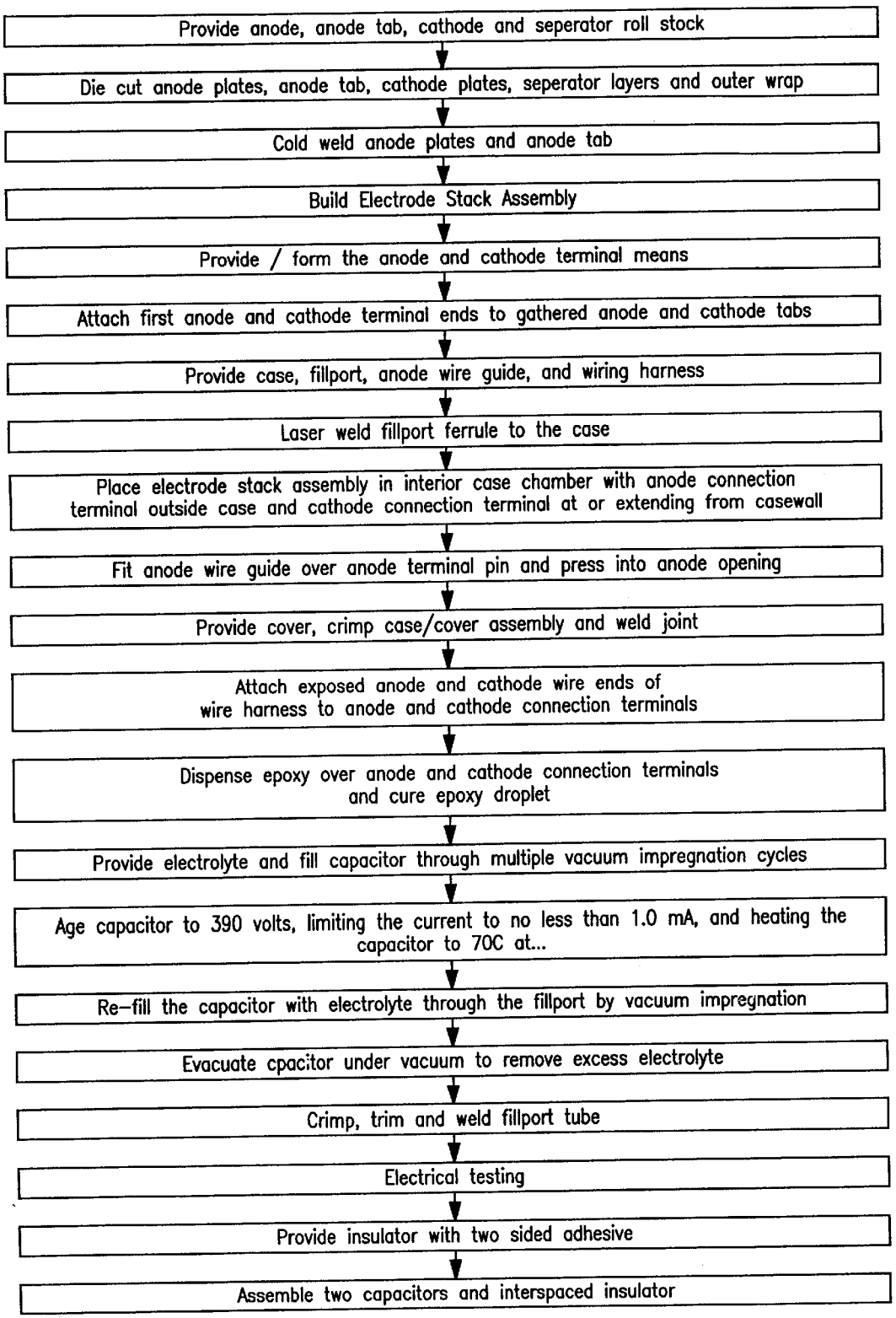
FIG. 13 is a flow chart of one method of the present invention for making a case negative capacitor incorporating the present invention.

FIG. 13 shows a flow chart that generally describes one method, from beginning to end, of making flat aluminum electrolytic capacitor 265 of the various embodiments of the invention. FIGS. 14 through 20, show specific portions of the method or process described generally in FIG. 13. FIG. 18 is specifically directed to the embodiments of the invention wherein the cathode terminal passageway is the cathode opening 143 of FIGS. 9, 10, 11($a$)–11($b$) and 21($a$)–21($b$) that cathode feedthrough pin 135 extends into or through or cathode opening 143' of FIGS. 23($a$)–23($b$) and 24($a$)–24($b$) that the cathode terminal or pin 125' extends into or through. These embodiments are first described, and the specific fabrication of the embodiments wherein the cathode terminal passageway is a portion or section of the upper edge of the case side wall are described further below.

Figure 5A:
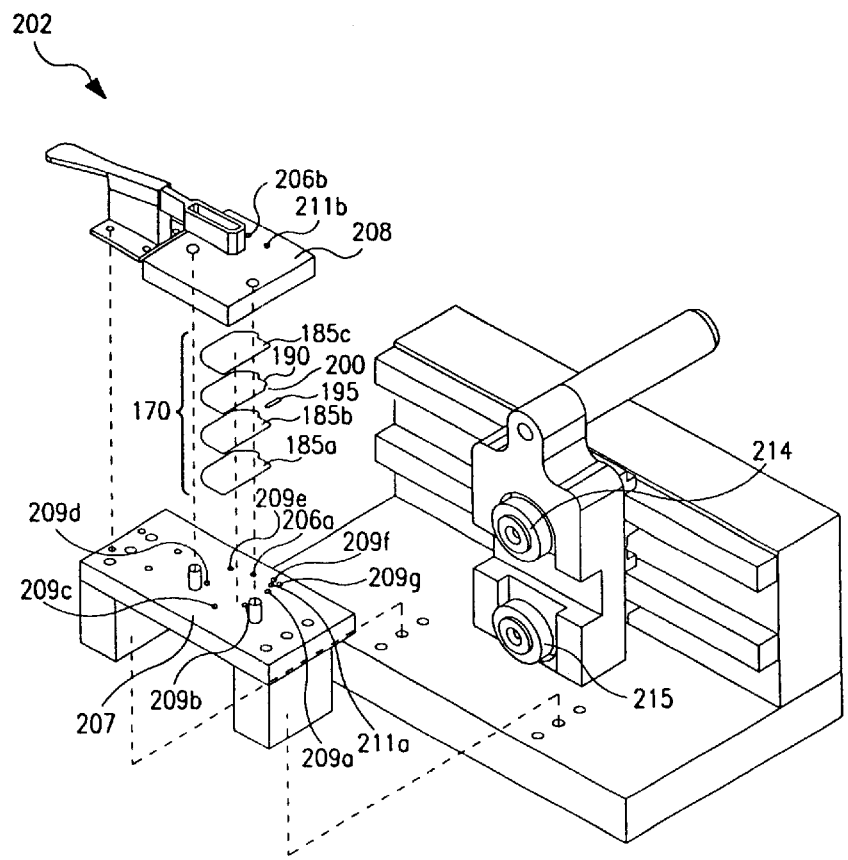
FIG. 5(a) is an exploded perspective view of one embodiment of a cold welding apparatus in which anode layers of the electrode stack sub-assembly of FIG. 4 are cold-welded.
Figure 5B:
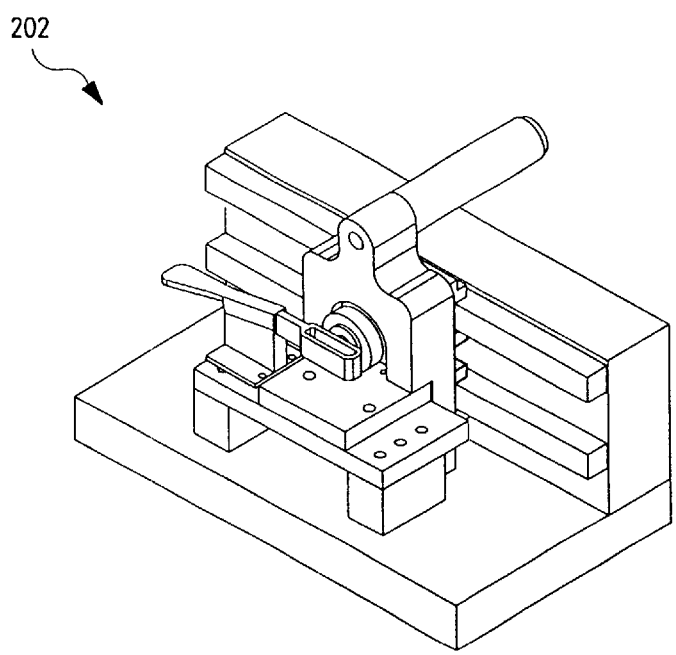
FIG. 5(b) is an unexploded view of the cold welding apparatus of FIG. 5(a)
Figure 14:
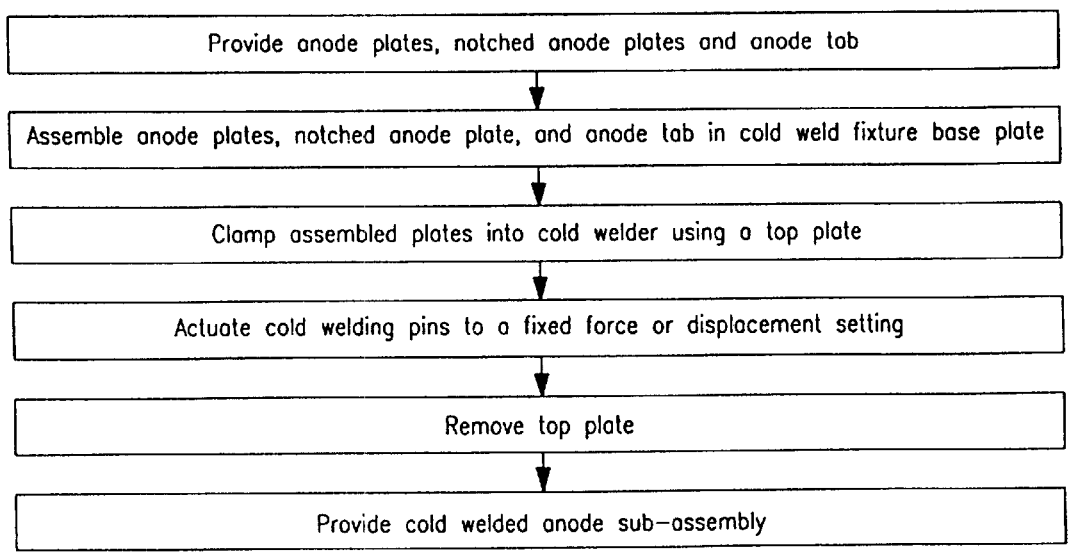
FIG. 14 is a flow chart of one method for making an anode layer of a capacitor incorporating the present invention.

First, the fabrication of the anode layers that can be used in fabricating an exemplary electrode stack assembly usable in all embodiments is described. FIG. 14 shows a flow chart of one method for making anode layer 170 wherein non-notched anode layers 185, notched anode layer 190 and anode tab 195 are provided and assembled within cold welder 202 to form anode sub-assembly 170. Referring now to FIGS. 5(*a*) through 5(*c*), two non-notched anode layers 185*a* and 185*b* are placed on cold welding fixture base layer 207 of cold welding apparatus 202. The various structural members of cold welding apparatus 202 are most preferably formed of precision machined stainless steel or a high strength aluminum alloy. Layers 185*a* and 185*b* are next aligned and positioned appropriately on cold welding fixture base layer 207 using spring loaded alignment pins 209*a* through 209*e*. Pins 209*a* through 209*e* retract upon top layer 208 being pressed downwardly upon layers 185*a* and 185*b* disposed within cold welding cavity 220. See also FIG. 5(*c*), where a cross-sectional view of cold welding apparatus 202 is shown.

Anode layer 190 is similarly disposed within cavity 220, followed by placing anode tab 195 within anode tab notch 200 in notched anode layer 190. Anode tab 195 is most preferably positioned along the periphery of notched anode layer 190 with the aid of additional spring loaded alignment pins 209*f* and 209*g* disposed along the periphery of anode tab 195. Non-notched anode layer 185*c* is then placed atop anode layer 190. Stacked anode sub-assembly 170 is then clamped between top plate 208 and base plate 207. Disposed within base plate 207 are anode layer cold welding pins 206*a* and anode tab cold welding pin 211*a*. Disposed within top plate 208 are anode layer cold welding pin 206*b* and anode tab cold welding pin 211*b*. Base plate 207 and top plate 208 are aligned such that the axes of cold welding pins 206*a* and 206*b* coincide with and are aligned respecting corresponding cold welding pins 211*a* and 211*b*.

Upper actuation apparatus 214 of cold welding apparatus 202 displaces cold welding pins 206*b* and 211*b* downwardly. Lower actuation apparatus 215 displaces cold welding pins 206*a* and 211*a* upwardly. In one embodiment of upper actuation apparatus 214 and lower actuation apparatus 215, pneumatic cylinders are employed to move pins 206*a*, 206*b*, 211*a* and 211*b*. In another embodiment of apparatus 214 and apparatus 215, a pair of rolling wheels is provided that move simultaneously and perpendicularly to the axes of pins 206*a*, 206*b*, 21*a*, and 211*b*. Still other embodiments of apparatus 214 and apparatus 215 may employ hydraulic actuators, cantilever beams, dead weights, springs, servomotors electromechanical solenoids, and the like for moving pins 206*a*, 206*b*, 21*a* and 211*b*. Control of actuation apparatus 214 and apparatus 215 respecting pin displacement force magnitude and timing may be accomplished using any one or combination of constant load, constant displacement, solenoid controller, direct or indirect means.

Following clamping with top plate 208, cold welding pins 206*a*, 206*b*, 211*a* and 211*b* are actuated. Cold welds 205 and 210 in anode sub-assembly 170 are formed by compression forces generated when cold weld pins 206*a*, 206*b*, 211*a* and 211*b* are compressed against anode sub-assembly 170. See FIG. 6(*a*), where the preferred regions in which cold welds 205 and 210 are formed are shown. Cold welds 205 and 210 may be described as not only cold welds, but forged welds. This is because the interfacial boundaries between anode layers 185 are deformed in the region of welds 205 and 210, thereby disrupting oxide layers and bringing base metals into direct contact with one another where metallic bonding occurs. Metallic bonding increases the strength of the welds.

In one embodiment of the method, a plurality of pneumatic cylinders function simultaneously in upper actuation apparatus 214 and lower actuation apparatus 215 to drive pins 206*a*, 206*b*, 211*a* and 211*b* against anode sub-assembly 170. Anode layer cold weld 205 and anode tab cold weld 210 are most preferably formed under direct constant load conditions, where pneumatic cylinders are pressurized to a predetermined fixed pressure. Anode layer cold weld 205 and anode tab cold weld 210 may also be formed under indirect constant displacement conditions, where pneumatic cylinders are pressurized until a displacement sensor placed across cold welding pins 206*a*, 206*b*, 211*a* or 211*b* generates a signal having a predetermined value, whereupon those pins are disengaged from anode/cathode sub-assembly 227.

In another embodiment of the method, a cantilever beam mechanism is incorporated into upper actuation apparatus 214 and lower actuation apparatus 215. Anode layer cold weld 205 and anode tab cold weld 210 are formed under direct constant displacement conditions, where cantilever beams are actuated and cause upper and lower members 208 and 207 to engage anode/cathode sub-assembly 227 until a hard stop point is reached. An indirect load controlled system may also be employed in apparatus 214 and apparatus 215, where cantilever or other means include a load measuring sensor for controlling the stop point of the cantilever beam, for example, when a predetermined load is measured by the sensor.

The cross-sectional shape of cold weld pins 206*a*, 206*b*, 211*a* and 211*b* may be square, circular, oval or any other suitable shape. The shape of the ends of cold weld pins 206*a*, 206*b*, 211*a* and 211*b* may be flat, rounded, domed or any other suitable shape appropriate for selectively controlling the properties of the cold welds produced therein. Likewise, more or fewer than four cold weld pins may be employed. The ends of cold weld pins 206*a*, 206*b*, 211*a* and 211*b* are most preferably rounded or domed and circular in cross-section. Cold weld pins 206*a*, 206*b*, 211*a* and 211*b* preferably have a diameter of about 0.060 inches (0.174 mm) and further have a beveled or radiused end. Cold weld pins 206*a*, 206*b*, 211*a* and 211*b* are preferably made from a high strength material that does not readily deform under the pressures obtained during welding, such as stainless steel, titanium, tool steel or HSLA steel. The ends or side walls of cold welding pins 206*a*, 206*b*, 211*a* and 211*b* may be coated, clad or otherwise modified to increase wear resistance, deformation resistance or other desirable tribilogical attributes of the pins.

The primary function of cold welds 205 and 210 is to provide electrical interconnections between layers 185*a*, 185*b*, 185*c* and 190 and anode tab 195, while minimizing the overall thickness of anode sub-assembly 170 in the regions of welds 205 and 210. Typical prior art commercial cylindrical capacitors exhibit a significant increase in the thickness of the anode layer in the regions of the cold welds. This increase in thickness is typically on the order of about two times the thickness of the tab, or about 0.008 inch (0.020 mm). In the case of cylindrical capacitors where only one or two non-coincident tab connections are present, the overall effect on anode layer thickness may be minimal. In a stacked layer design having many more interconnections and welds, however, increases in weld zone thickness have been found to significantly increase the overall thickness of the anode layer and the electrode stack assembly as a whole.

In one cold welding method and corresponding apparatus, no or an inappreciable net increase in anode sub-assembly 170 thickness results when cold weld geometries and formation processes are appropriately optimized. Several embodiments of anode-assembly 170 have been found to have no more than about a 20% increase in layer thickness due to the presence of cold welds, as compared to about a 200% increase in thickness resulting from cold welds found in some commercial cylindrical capacitors. Two, three, four, five, six or more anode layers 185 and 190 may be cold-welded to form anode sub-assembly 170 as described herein.

Figure 6A:
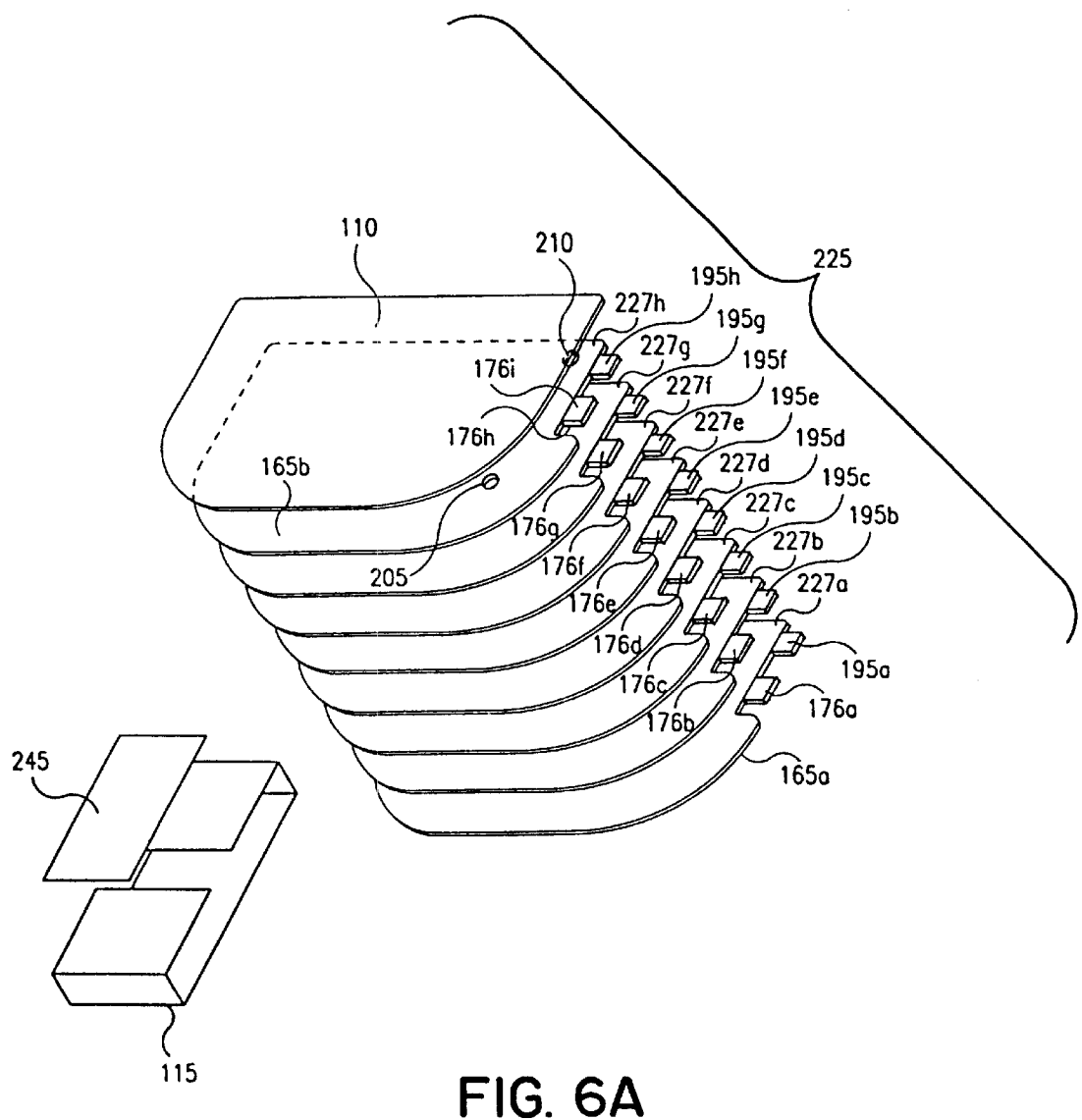
FIG. 6(a) is an exploded top perspective view of one embodiment of a stack of anode/cathode layer sub-assemblies into a stacked electrode stack assembly of an electrolytic capacitor incorporating the present invention.
Figure 6B:
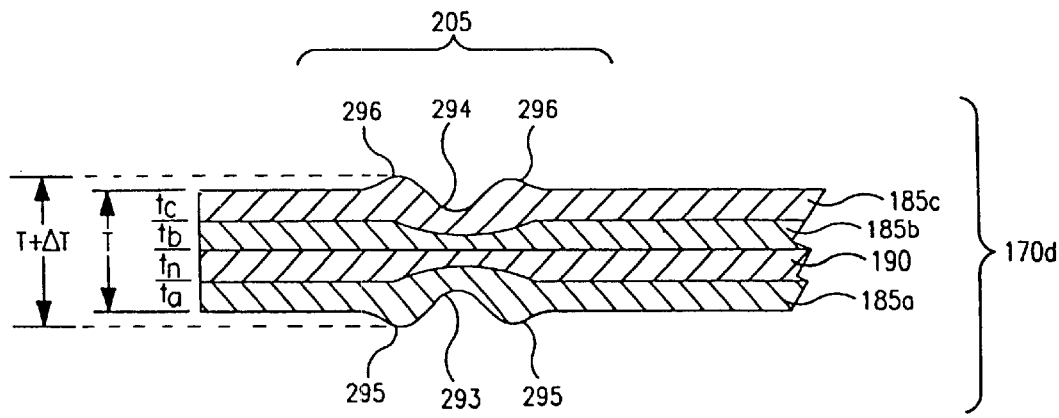
FIG. 6(b) is a cross-sectional view of a portion of one embodiment of a cold-welded anode assembly used in the electrolytic capacitor.
Figure 6C:
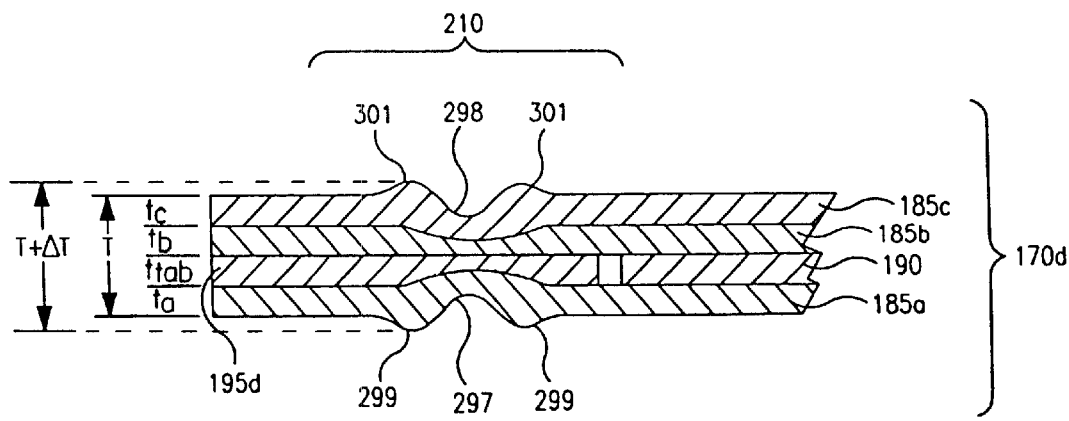
FIG. 6(c) is a cross-sectional view of another portion of one embodiment of a cold-welded anode assembly used in the electrolytic capacitor.

FIG. 6(*b*) shows a cross-sectional view of a portion of one embodiment of a cold-welded anode assembly formed in accordance with the preferred cold welding method. Anode layers 185*a*, 190, 185*b* and 185*c* having anode layer thicknesses $t_a$, $t_N$, $t_b$ and $t_c$, respectively, are cold-welded together at weld 205 through the compressive action of pins 206*a* and 206*b* mounted in bottom plate 207 and top plate 208, respectively. Pins 206*a* and 206*b* form central depressions 293 and 294, respectively, in anode sub-assembly 170*d*, and further result in the formation of rims 295 and 296, respectively. Rims 295 and 296 project downwardly and upwardly, respectively, from the surrounding surfaces of anode sub-assembly 170*d*, thereby increasing the overall thickness T of anode sub-assembly 170*d* by ΔT (T measured in respect of the non-cold-welded surrounding regions or portions of anode sub-assembly 170*d*).

FIG. 6(*c*) shows a cross-sectional view of another portion of one embodiment of a cold-welded anode assembly wherein anode layers 185*a*, 185*b* and 185*c* and anode tab 195, having anode layer/tab thicknesses $t_a$, $t_b$, $t_c$ and $t_{tab}$, respectively, are cold-welded together at weld 210 through the compressive action of pins 211*a* and 211*b* mounted in bottom plate 207 and top plate 208, respectively. Pins 211*a* and 211*b* form central depressions 297 and 298, respectively, in anode sub-assembly 170*d*, and further result in the formation of rims 299 and 301, respectively. Rims 299 and 301 project downwardly and upwardly, respectively, from the surface of anode sub-assembly 170*d*, thereby increasing overall thickness T of anode sub-assembly 170*d* by ΔT (T measured in respect of the non-cold-welded surrounding regions or portions of anode sub-assembly 170*d*).

The overall thickness T of anode sub-assembly 170*d* is therefore defined by the equation:

$$T=nt$$

The maximum overall thickness T+ΔT of anode sub-assembly 170*d* in the region of cold welds 205 or 210 is then defined by the equation:

$$T+\Delta T=nt+\Delta T$$

where $T_{as}$ is the overall thickness of anode sub-assembly 170*d* in non-cold-welded regions, n is the number of anode layers 185 and/or 190 in anode sub-assembly 170*d*, and t is the thickness of individual anode layers 185 and/or 190 or anode tab 195 where the thicknesses $t_n$, $t_a$, $t_b$, $t_c$ and $t_{tab}$ are assumed to be the same.

It is highly desirable to form anode sub-assembly such that the ratio ΔT/T is less than or equal to 0.05, 0.1, 0.15, 0.20, 0.25, 0.30, 0.35, 0.40, 0.45 or 0.50. The lower the value of the ratio ΔT/T, the greater the volumetric efficiency of capacitor 265. Additionally, the overall thickness of capacitor 265 may be reduced when the value of the ratio ΔT/T is made smaller.

Referring now to FIG. 6(*a*), the overall thickness of electrode stack assembly 225 may be reduced further by staggering or offsetting horizontally the respective vertical locations of tabs 195*a* through 195*h* (and corresponding cold welds 210). In this embodiment, tabs 195*a* 195*b*, for example, are not aligned vertically in respect of one another. Such staggering or offsetting of tabs 195 permits the increases in thickness ΔT corresponding to each of anode subassemblies 170*a* through 170*h* to be spread out horizontally over the perimeter or other portion of electrode stack assembly 225 such that increases in thickness ΔT do not accumulate or add constructively, thereby decreasing the overall thickness of electrode stack assembly 225. Cold welds 205 may similarly be staggered or offset horizontally respecting one another and cold weld 210 to achieve a reduction in overall thickness of electrode stack assembly 225.

In another preferred embodiment, the anode sub-assembly 170 of each capacitor layer or electrode sub-assembly comprises a plurality of three, four, five or more anode sheets or layers 185 and 190, each sub-assembly most preferably having at least one anode layer having a corresponding anode tab 195 attached thereto or forming a portion thereof the layers being cold welded together to form anode sub-assembly 170. For example, an anode sub-assembly 170 may comprise six anode layers 185 constructed by cold-welding two separate triple anode layers 185 that were previously and separately cold-welded or otherwise joined together. Alternatively, anode sub-assembly 170 layer may comprise seven anode layers constructed by cold-welding together one triple anode layer 185 and one quadruple anode layer 185 that were previously and separately cold-welded or otherwise joined together. In another preferred embodiment, multiple notched anode layers 190 may employed in anode sub-assembly 170, thereby permitting the use of a thicker anode tab material.

The geometry of base plate 207 and top plate 208 in the regions surrounding cold welding pins 206*a*, 206*b*, 211*a* and 211*b* has been discovered to affect the properties of cold welds 205 and 210. In a preferred method, the mating surfaces of plates 207 and 208 surfaces have no radiused break formed in the perimeters of the pin holes. The presence of radiused breaks or chamfers in those regions may cause undesired deformation of cold welds 205 and 210 therein. Such deformation may result in an increase in the thickness of anode sub-assembly 170, which may translate directly into an increase in the thickness of capacitor 265. Note further that the increase in thickness so resulting is a multiple of the number of anode sub-assemblies 170 present in electrode stack assembly 225. Alternatively, radiused breaks or chamfers may be employed in the region of the pin holes in base plate 207 and top plate 208, but appropriate capacitor design accommodations are most preferably made, such as staggering the positions of adjoining stacked cold welds.

Figure 15:
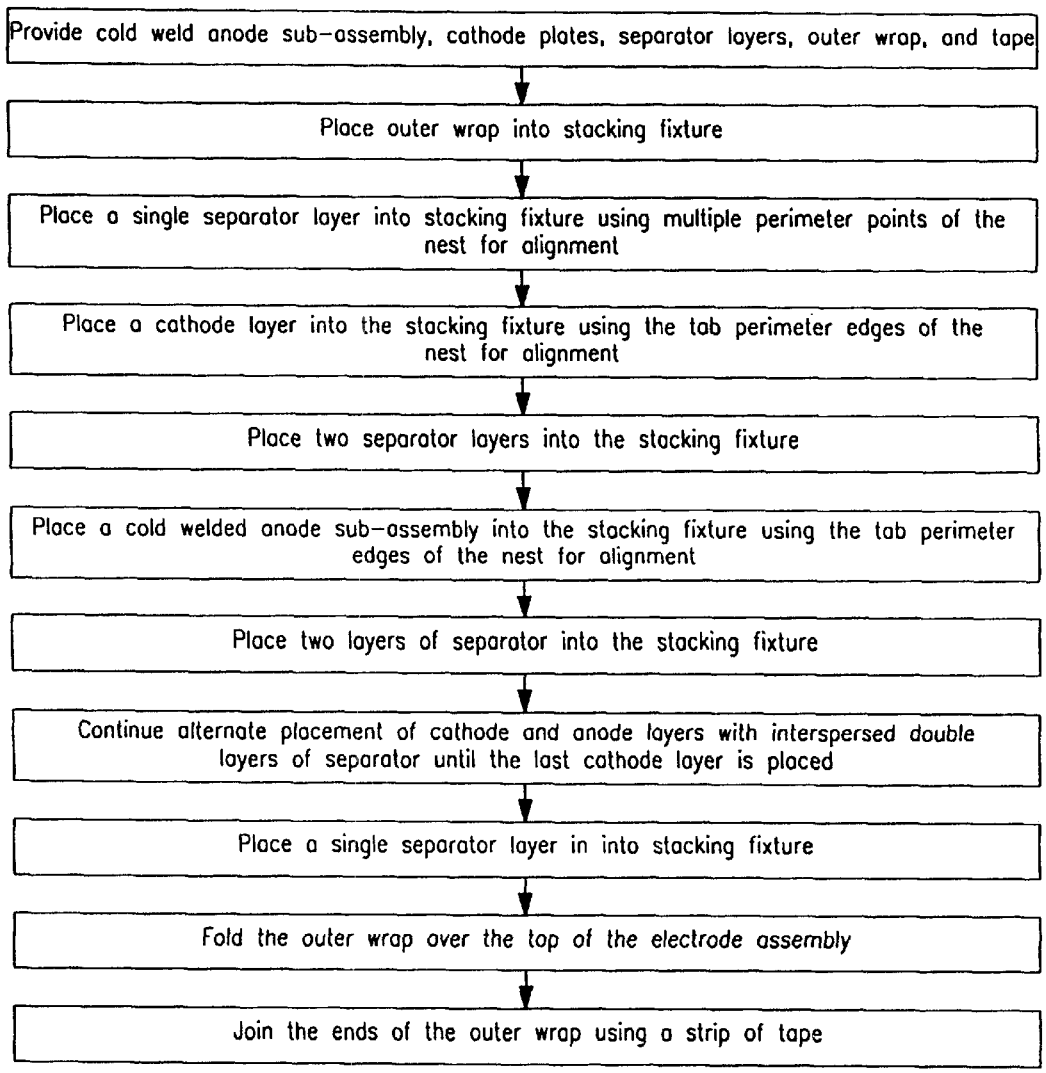
FIG. 15 is a flow chart of one method for making an electrode stack assembly of a capacitor incorporating the present invention.

As shown in FIG. 14, once cold welding pins 206*a*, 206*b*, 211*a* and 211*b* have been actuated against anode sub-assembly 170, top plate 208 is removed and cold-welded anode sub-assembly 170 is provided for further stacking of anode/cathode sub-assembly 227. FIG. 15 shows a flow chart corresponding to one preferred method for making electrode stack assembly 225. See also FIG. 6(*a*), where an exploded top perspective view of one embodiment of an electrode stack assembly 225 of capacitor 265 is shown. As illustrated in FIGS. 4, 6(*a*) and 15, electrode stack assembly 225 most preferably comprises a plurality of cold-welded anode sub-assemblies 175*a* through 175*h*, a plurality of cathode layers 175*a* through 175*i*, a plurality of separator layers 180, outer separator layers 165*a* and 165*b*, outer wrap 115 and wrapping tape 245.

Outer wrap 115 is most preferably die cut from separator material described supra, but may be formed from a wide range of other suitable materials such as polymeric materials, aluminum, suitable heat shrink materials, suitable rubberized materials and synthetic equivalents or derivatives thereof, and the like.

Wrapping tape 245 is most preferably cut from a polypropylene-backed acrylic adhesive tape, but may also be replaced by a staple, an ultrasonic paper joint or weld, suitable adhesives other than acrylic adhesive, suitable tape other than polypropylene-backed tape, a hook and corresponding clasp and so on.

Outer wrap 115 and wrapping tape 245 together comprise an electrode stack assembly wrap which has been discovered to help prevent undesired movement or shifting of electrode stack assembly 225 during subsequent processing. It will now become apparent to one skilled in the art that many means other than those disclosed explicitly herein exist for immobilizing and securing electrode stack assembly 225 during subsequent processing which accomplish substantially the same function as the electrode stack assembly wrap comprising outer wrap 115 and wrapping tape 245. Alternative means for immobilizing and securing electrode stack assembly 225 other than those described hereinabove exist. Such alternative means include, but are not limited to, robotic or other mechanical clamping and securing means not necessarily forming a portion of electrode stack assembly 225, adhesive electrolytes for forming separator layers 180, and so on.

The stacking process by which electrode stack assembly 225 is most preferably made begins by placing outer wrap 115 into a stacking fixture followed by placing outer paper or separator layer 165a thereon. Next, cathode layer 175a is placed atop separator layer 165a, followed by separator layers 180a and 180b being disposed thereon. Cold-welded anode sub-assembly 170a is then placed atop separator layer 180b, followed by placing separator layers 180a and 180b thereon, and so on. The placing of alternating cathode layers 175 and anode sub-assemblies 170 with separator layers 180a and 180b interposed therebetween continues in the stacking fixture until final cathode layer 175h has been placed thereon.

In the embodiment of electrode stack assembly 225 shown in FIG. 6(a), eight anode sub-assemblies (anode sub-assemblies 170a through 170h) and nine cathode layers (cathode layers 175a through 175i) are illustrated. The voltage developed across each combined anode sub-assembly/separator layer/cathode layer assembly disposed within electrode stack assembly 225 most preferably ranges between about 360 and about 390 Volts DC. As described below, the various anode sub-assemblies of electrode stack assembly 225 are typically connected in parallel electrically, as are the various cathode layers of electrode stack assembly 225.

Consistent with the discussion hereinabove concerning FIG. 4, it will now be understood by one skilled in the art that electrode stack assembly 225 shown in FIG. 6(a) is merely illustrative, and does not limit the scope of the present invention in any way respecting the number or combination of anode sub-assemblies 170, cathode layers 175, separator layers 180, anode tabs 195, cathode tabs 176, and so on. The number of electrode components is instead determined according to the total capacitance required, the total area of each layer, the specific capacitance of the foil employed and other factors.

In another embodiment of electrode stack assembly 225, the number of anode layers 185 employed in each anode sub-assembly 170 is varied in the stack. Such a design permits the fabrication of capacitors having the same layer area but nearly continuously varying different and selectable total capacitances that a user may determine by increasing or decreasing the number of anode layers 185/190 included in selected anode sub-assemblies 170 (as opposed to adding or subtracting full anode/cathode sub-assemblies 227 from electrode stack assembly 225 to thereby change the total capacitance). Following placing of cathode layer 175i in the stack, outer paper layer 165b is placed thereon, and outer wrap 115 is folded over the top of electrode stack assembly 225. Wrapping tape 245 then holds outer wrap 115 in place and secures the various components of electrode stack assembly 225 together.

The physical dimensions of separator layers 165 and 180 are most preferably somewhat larger than those of anode sub-assemblies 170 and cathode layers 175 to prevent contact of the electrodes with the case wall or electrical shorting between opposing polarity electrode layers due to the presence of burrs, stray or particulate material, debris or imperfections occurring therein. The reliability and functionality of capacitor 265 may be compromised if a portion of anode sub-assembly 170 comes into contact with a conducting case wall, if a burr on the periphery of anode sub-assembly 170 or cathode layer 175 comes into contact with an adjoining layer of opposing polarity, or if separator layer 180a or 180b does not provide sufficient electrical insulation between adjoining opposite-polarity electrode layers and conducting particulate matter bridges the gap therebetween.

The additional separator material most preferably disposed about the periphery of electrode stack assembly 225 is referred to herein as separator overhang. Decreasing the amount of separator overhang increases the energy density of capacitor 265. It is beneficial from an energy density optimization perspective, therefore, to decrease the amount or degree of separator overhang. The amount of separator overhang required has been discovered to be primarily a function of the stack-up tolerance characteristic of the stacking method employed.

In commercial cylindrical capacitors, the amount of separator overhang is typically on the order of 0.050 to 0.100 inches (0.127 to 0.254 mm). The above-referenced '851 patent describes a flat aluminum electrolytic capacitor wherein the housing of the capacitor has at least two internal alignment members. Those alignment members necessarily add volume to the capacitor while taking away from the total amount of "active" electrode material available, thereby decreasing the energy density of the capacitor.

A preferred method for assuring consistent registration of separator layers 165 and 180, anode sub-assemblies 170 and cathode layers 175 in electrode stack assembly 225 involves stacking the various elements of electrode stack assembly 225 using robotic assembly techniques. More particularly, the various electrode and separator layers of electrode stack assembly 225 are stacked and aligned using an assembly work cell comprising four Seiko 4-axis SCARA Model No. TT8900 and TT8500, or equivalent, to pick up and place the various electrode and separator elements in an appropriate stacking fixture. Other suitable methods for stacking and registering electrode and separator layers include cam driven walking beam assembly machine techniques, rotary table machine techniques, multiple station single stacking machine techniques, and the like.

In a preferred method, a pre-formed or cut separator, electrode layer or sub-assembly is presented to a robot arm, which then picks the part up with end-of-arm tooling. A Venturi system produces a vacuum in the end-of-arm tooling. The system creates a vacuum at an appropriate time such that the part is sucked up onto the end-of-arm tooling. The vacuum is next released when the part is placed in the stacking fixture. A direct vacuum system, such as rubber suction cups, or other contact or non-contact pick up robotic or manual assembly methods may also be employed. The position of the part is robotically translated from the pickup point into the stacking fixture by the robot arm with an accuracy of 0.005 inch (0.013 mm) or less. After placing the part in the stacking fixture, part alignment is most preferably verified electronically with a SEIKO COGNEX 5400 VISION System, or equivalent, in combination with a SONY XC-75 camera, or equivalent. The camera is mounted on the robot arm to permit the accuracy of part placing to be verified. This system can accurately determine the position of each part or element in electrode stack assembly 225 to within 0.01 millimeters. Once all layers have been placed in the stacking fixture by the robot arm, the stack is presented for wrapping.

The foregoing methods permit precise alignment and stacking of separator layers 165 and 180, anode sub-assemblies 170, and cathode layers 175 in electrode stack assembly 225, while minimizing the addition of undesirable unused volume to capacitor 265.

Another method for assuring registration of separator layers 165 and 180, anode sub-assembly 170 and cathode layer 175 in electrode stack assembly 225 involves alignment elements disposed within the stacking fixture are employed in a manual process which utilizes fixture registration points. In such a method, the stacking fixture has several alignment elements such as posts or side walls disposed about its periphery for positioning separator layers 165 and 180. Because cathode layers 175 and anode sub-assemblies 170 do not extend to the periphery of the separator, an alternative means for accurately positioning those electrodes becomes necessary.

Positioning of alternating cathode layers 175 and anode sub-assemblies 170 is most preferably accomplished using alignment elements such as posts or side walls disposed about the periphery of cathode tab 176 and anode tab 195. It has been discovered that the accuracy of layer placing and positioning is primarily a function of the length of the electrode tabs. The longer the tab, the less significant the alignment error becomes. Electrode tab length must typically be balanced against the loss of electrode material which occurs during die cutting, which in turn results primarily due to the longer length of cathode tab 176 in respect of the length of anode tab 195. Tabs 176 and 195 may include or contain alignment features therein having any suitable geometry for facilitating registration and positioning in respect of alignment elements. Any additional tab length utilized for registration of the electrode layers is most preferably trimmed from electrode stack assembly 225 during the process of electrode tab interconnection (more about which we say below).

Another method for ensuring registration of separator layers 165 and 180, anode sub-assembly 170 and cathode layer 175 in electrode stack assembly 225 does not require the use of internal alignment elements within capacitor 265 is enveloping or covering anode sub-assembly 170 and cathode layer 175 with separator material. In this method, separator layers 180a and 180b are combined into a single die cut piece part that is folded around either anode sub-assembly 170 or cathode layer 175. The free edges of the separator are then secured by doubled-sided transfer tape, another adhesive, stitching or ultrasonic paper welding. Construction of an electrode sub-assembly in this manner secures and registers anode sub-assembly 170 and cathode layer 175 in respect of the periphery of the separator envelope so formed. The resulting anode/cathode sub-assembly or capacitor layer 227 is then presented for stacking in electrode stack assembly 225.

Yet another method for securing the separator to anode sub-assembly 170 is through the use of pressure bonding techniques. In such a method, separator layer 165 or 180 is pressed into a surface of anode sub-assembly 170 or anode layer 185 over a localized region thereof with sufficient force to rigidly affix the separator paper to anode sub-assembly 170, but not with such great force that a portion of underlying anode sub-assembly 170 is fractured. Other methods of securing all or portions of separator layer 165 or 180 to anode sub-assembly 170 or anode layer 185 include, but are not limited to, stitching, adhesive bonding and ultrasonic paper welding techniques.

Figure 7:
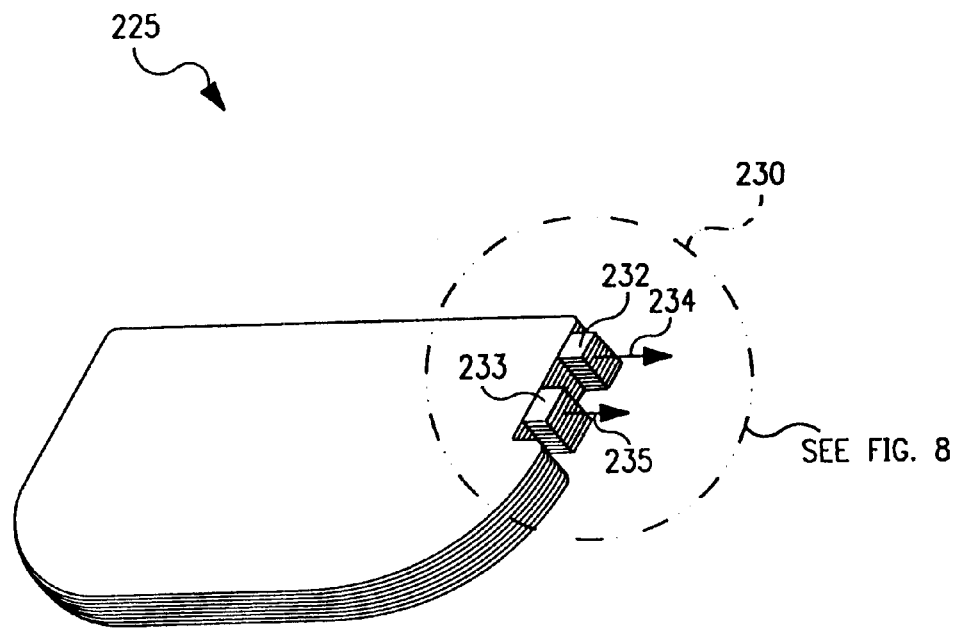
FIG. 7 is a top perspective view of one embodiment of an electrode stack assembly of an electrolytic capacitor incorporating the present invention.
Figure 8:
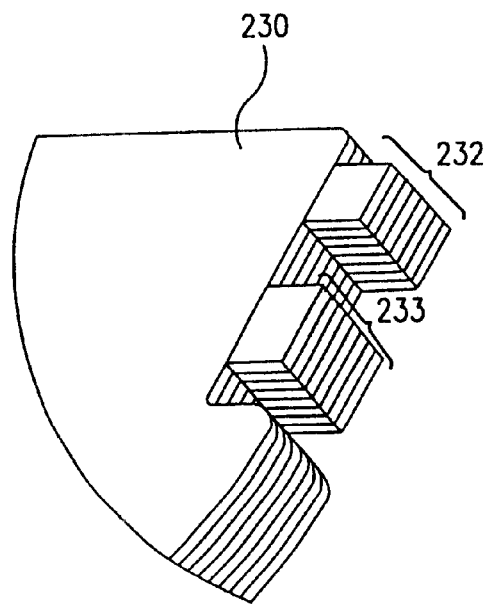
FIG. 8 is an enlarged view of a portion of the electrode stack assembly shown in FIG. 7.

FIG. 7 shows a top perspective view of one embodiment of an electrode stack assembly 225 of the electrolytic capacitor 265. FIG. 8 shows an enlarged view of a portion of the electrode stack assembly 225 of FIG. 7. After wrapping electrode stack assembly 225 with outer wrap 115 and wrapping tape 245, interconnection of gathered anode tabs 232 and gathered cathode tabs 233 with their respective external terminals is most preferably made.

Figure 9:
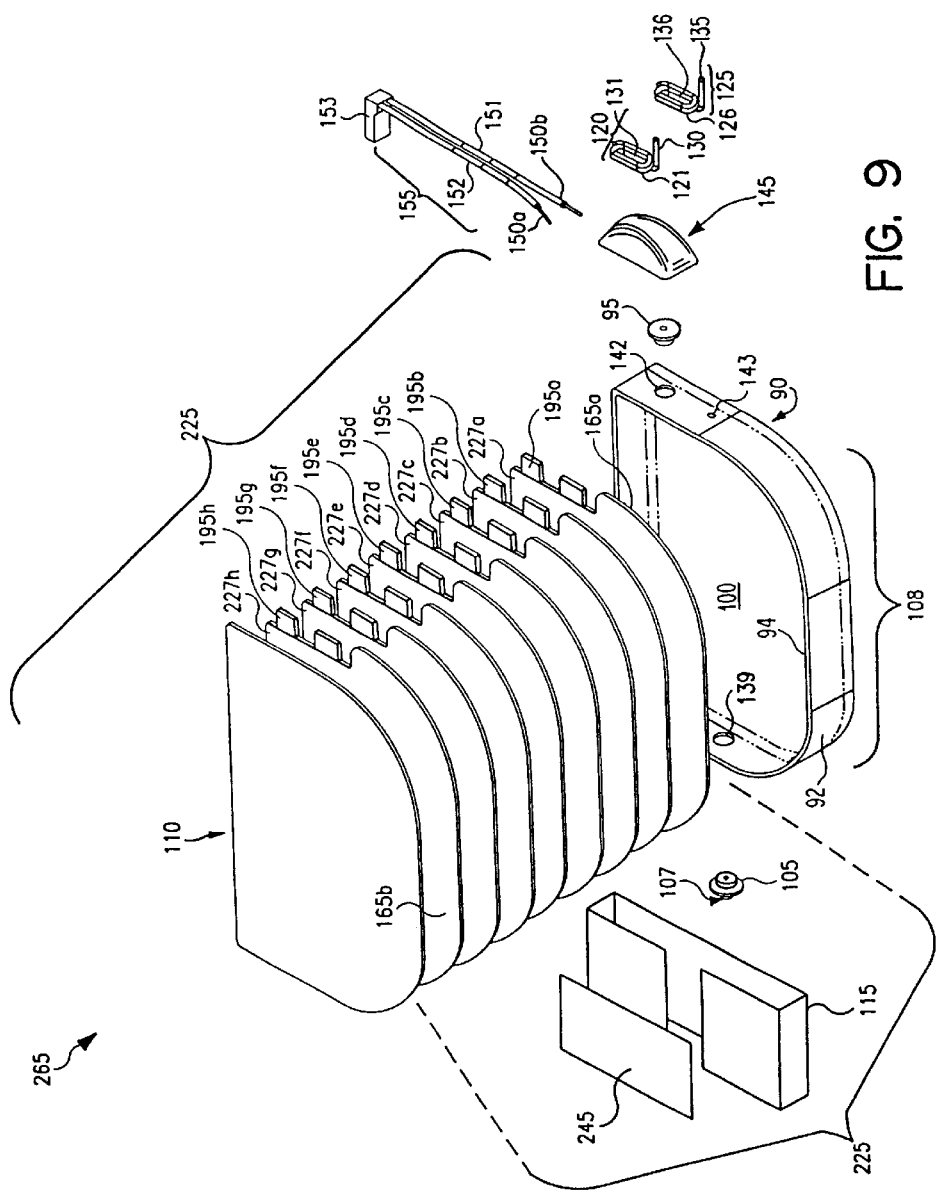
FIG. 9 is an exploded top perspective view of one embodiment of a case negative capacitor of the present invention employing the electrode stack assembly of FIGS. 6, 7 and 8 therein.
Figure 10:
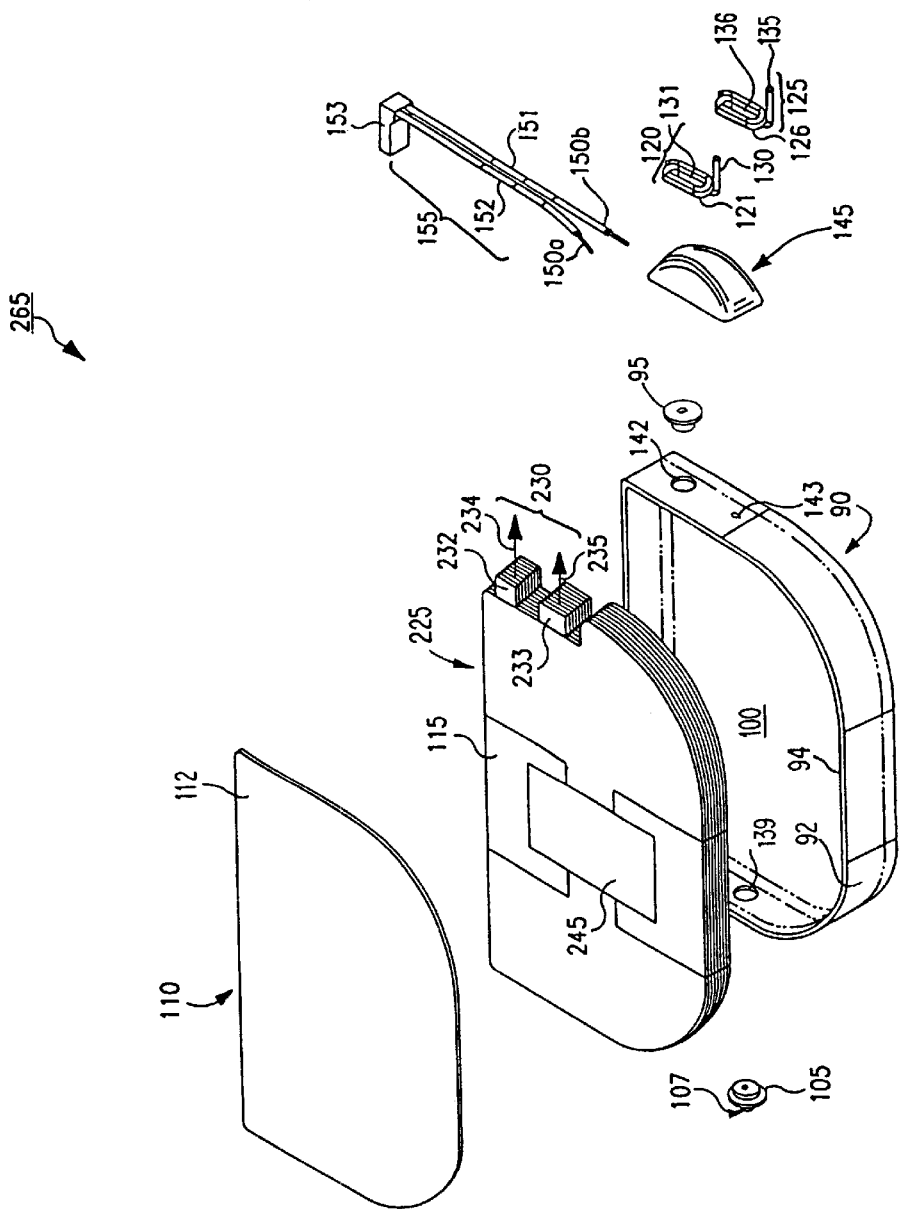
FIG. 10 is an exploded top perspective view of the partially assembled capacitor of FIG. 9.
Figure 11A:
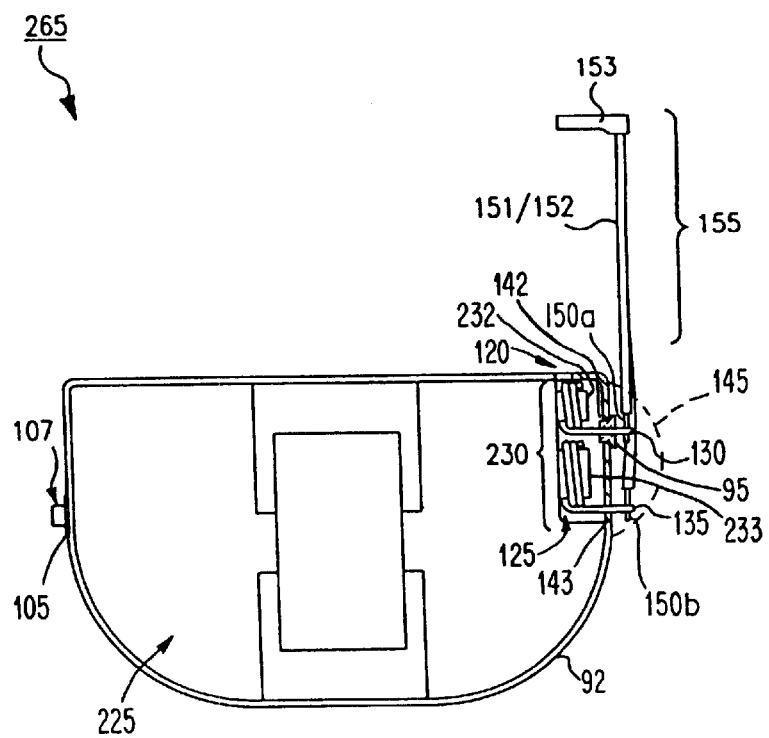
FIG. 11(a) is a top view of one embodiment of a partly assembled capacitor of the present invention having no cover disposed thereon.
Figure 11B:
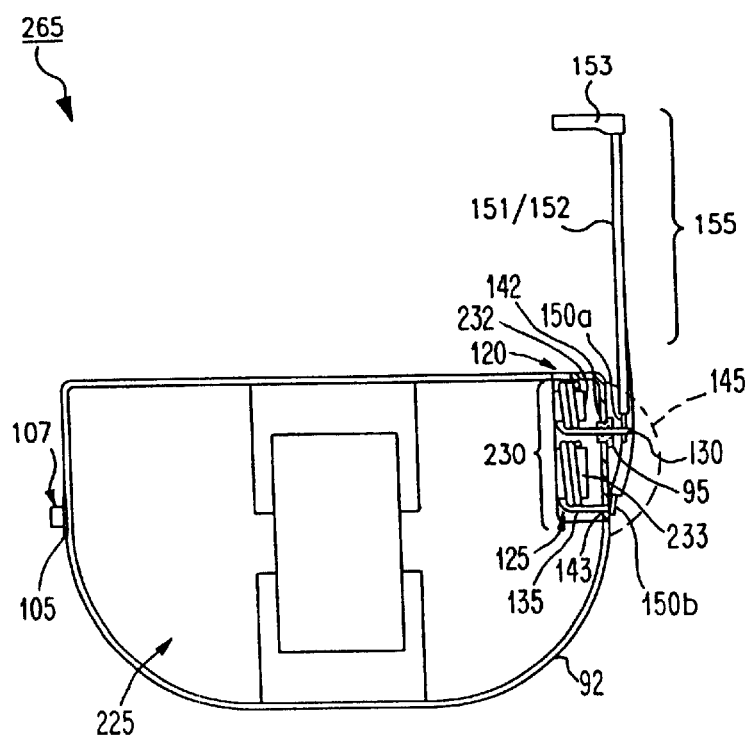
FIG. 11 (b) is a top view of one embodiment of a partly assembled capacitor of the present invention having no cover disposed thereon.
Figure 12:
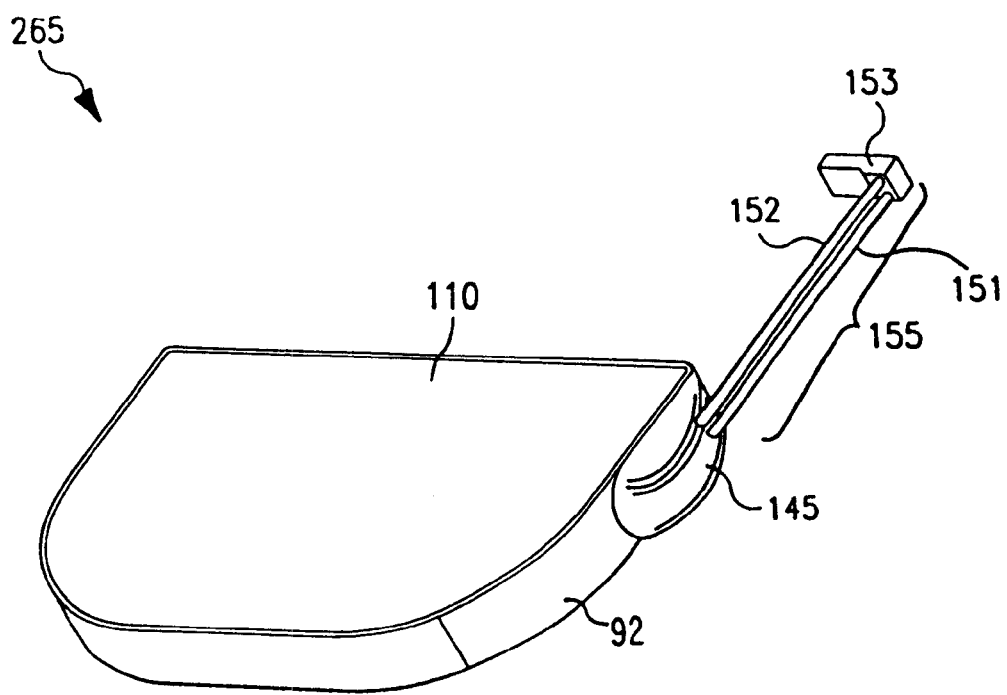
FIG. 12 is a top perspective view of the capacitor of FIG. 11 having a cover disposed thereon.
Figure 22A:
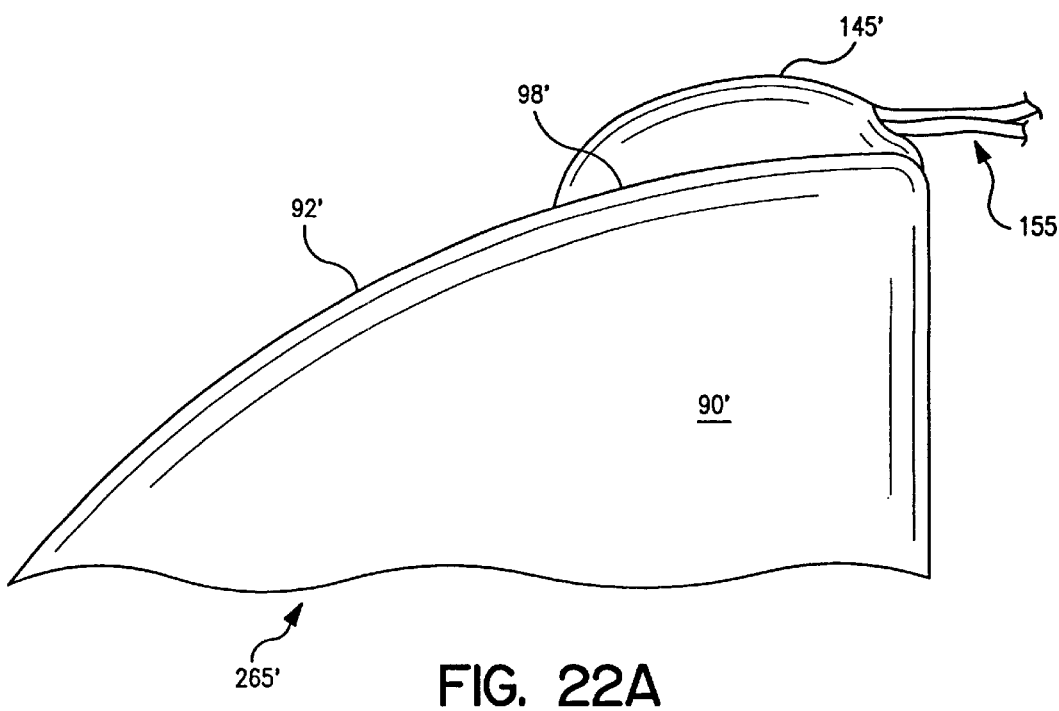
FIGS. 22(a) and 22(b) are side elevation views of two embodiments of miniaturized, case negative, capacitors formed with epoxy droplet connector blocks.

FIGS. 9 and 10 show exploded top perspective views of one case negative embodiment of a capacitor 265 employing the electrode stack assembly of FIGS. 6, 7 and 8 therein and the connector block 145 formed of an epoxy droplet over the anode and cathode feedthroughs 120 and 125. Other case negative embodiments are described further below in reference to FIGS. 22–24. The connector block 145 is shown as a discrete part, but it will be understood that it is formed in situ, after assembly of the capacitor 265, of a cured epoxy droplet as shown in FIGS. 11 and 12 and described further below with reference to the flow chart of FIG. 20.

Figure 16:
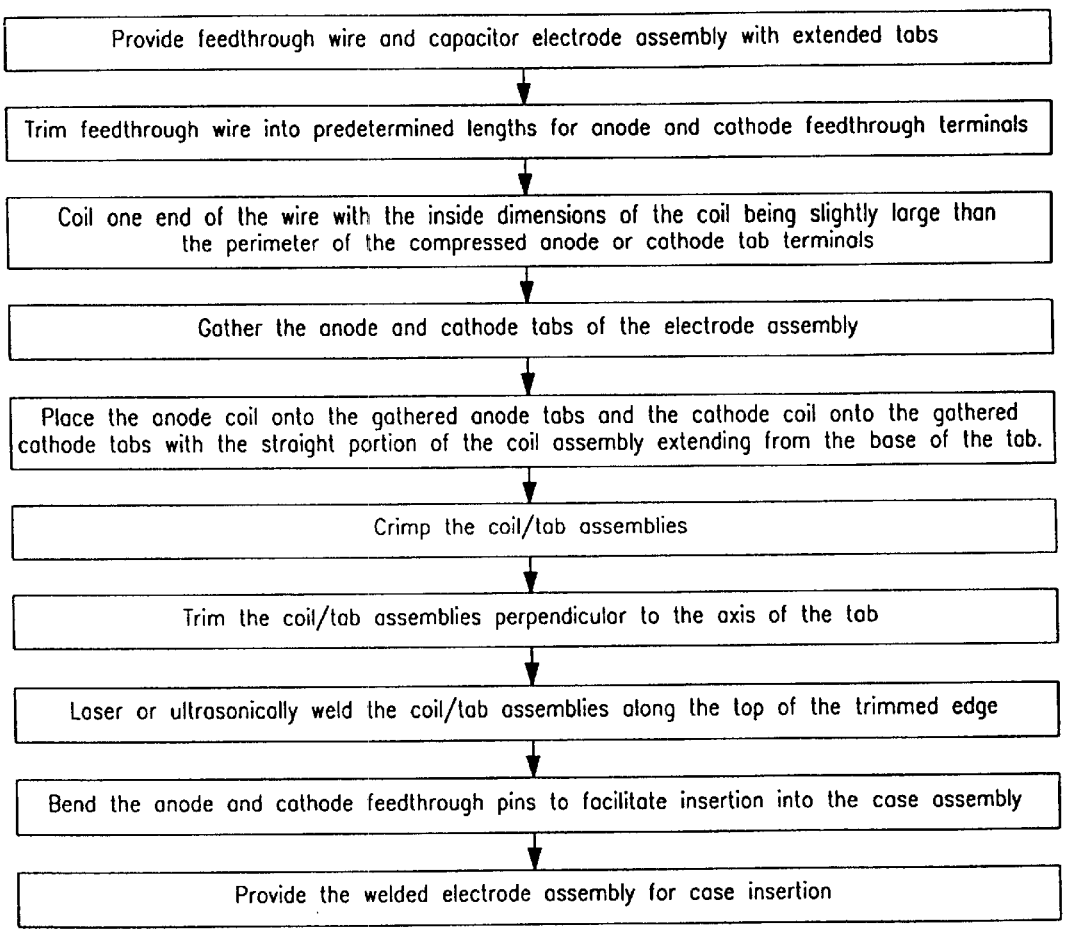
FIG. 16 is a flow chart of one method for making tab interconnections and feedthrough terminal connections of a capacitor incorporating the present invention.

FIG. 16 shows a flow chart corresponding to one method of forming anode terminal means and a cathode terminal extending through anode and cathode terminal passageways in the case wall, particularly, the case side wall 92. The tab interconnections and feedthrough terminal connections of certain steps of FIG. 13 (that are also shown in FIGS. 11(a) and 11(b)) provide anode and cathode connection terminals. This case negative embodiment employs anode feedthrough 120 and cathode feedthrough 125 most preferably have coiled basal portions 121 and 126, respectively, that surround and are welded to gathered anode tabs 232 and gathered cathode tabs 233, respectively. The feedthrough pins 130 and 135 provide external connection terminals for capacitor 265.

In this method, feedthrough wire is first provided for construction of feedthroughs 120 and 125. In one embodiment, a preferred feedthrough wire is aluminum having a purity is greater than or equal to 99.99% and a diameter of 0.020 inch (0.510 mm). Wire is trimmed to predetermined lengths for use in anode feedthrough 120 or cathode feedthrough 125. One end of the trimmed wire is coiled such that its inside diameter or dimension is slightly larger than the diameter or dimension required to encircle gathered anode tabs 232 or gathered cathode tabs 233.

Anode tabs are next gathered, or brought together in a bundle of gathered anode tabs 232 by crimping, and inside diameter 131 of anode feedthrough coil assembly 120 is placed over gathered anode tabs 232 such that anode feedthrough pin 130 extends outwardly away from the base of gathered anode tabs 232. Similarly, gathered cathode tabs 233 are gathered and inside diameter 136 of cathode feedthrough coil assembly 125 is placed over gathered cathode tabs 233 such that cathode feedthrough pin 135 extends outwardly away from the base of cathode tab 233. Coiled basal portions 121 and 126 of anode and cathode feedthroughs 120 and 125 are then most preferably crimped onto anode and cathode tabs 232 and 233, followed by trimming the distal ends thereof. Most preferably the crimps so formed are oriented substantially perpendicular to imaginary axes 234 and 235 of tabs 232 and 233. Trimming the tab distal ends may also, but less preferably, be accomplished at other non-perpendicular angles respecting imaginary axes 234 and 235.

A crimping force is applied to feedthrough coils 121 and 126 and gathered tabs 232 and 233 throughout a subsequent preferred welding step. In one method, it is preferred that the crimped anode and cathode feedthroughs be laser or ultrasonically welded along the top portion of the trimmed edge of the distal ends to anode and cathode tabs 232 and 233. Pins 130 and 135 are bent for insertion through anode and cathode holes 142 and 143 of case 90 following welding of feedthroughs 120 and 125 to gathered anode tabs 232 and gathered cathode tabs 233, respectively.

Many different embodiments of the feedthroughs 120 and 125, and means for connecting the feedthroughs to anode and cathode tabs 232 and 233 exist other than those shown explicitly in the figures. For example, the feedthroughs include embodiments comprising basal portions having open sides, forming "U" or "T" shapes in cross-section, forming a coil having a single turn of wire, forming a coil having three or more turns of wire, formed from flattened wire, or basal portions formed from crimping sleeves or layers of metal for connecting feedthrough pins 130 and 135 to gathered anode and cathode tabs 232 and 233.

Figure 17:
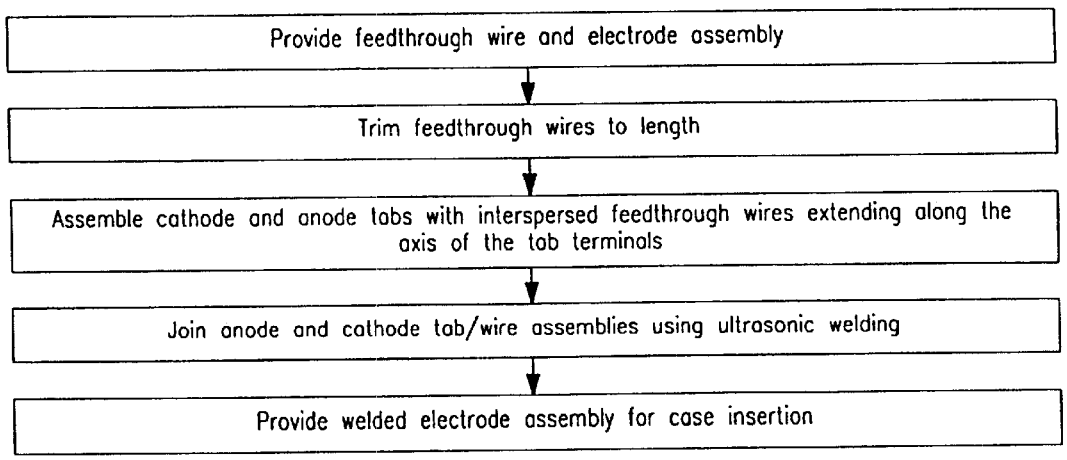
FIG. 17 is a flow chart of one method for making tab interconnections and feedthrough terminal connections of a capacitor incorporating the present invention.
Figure 18:
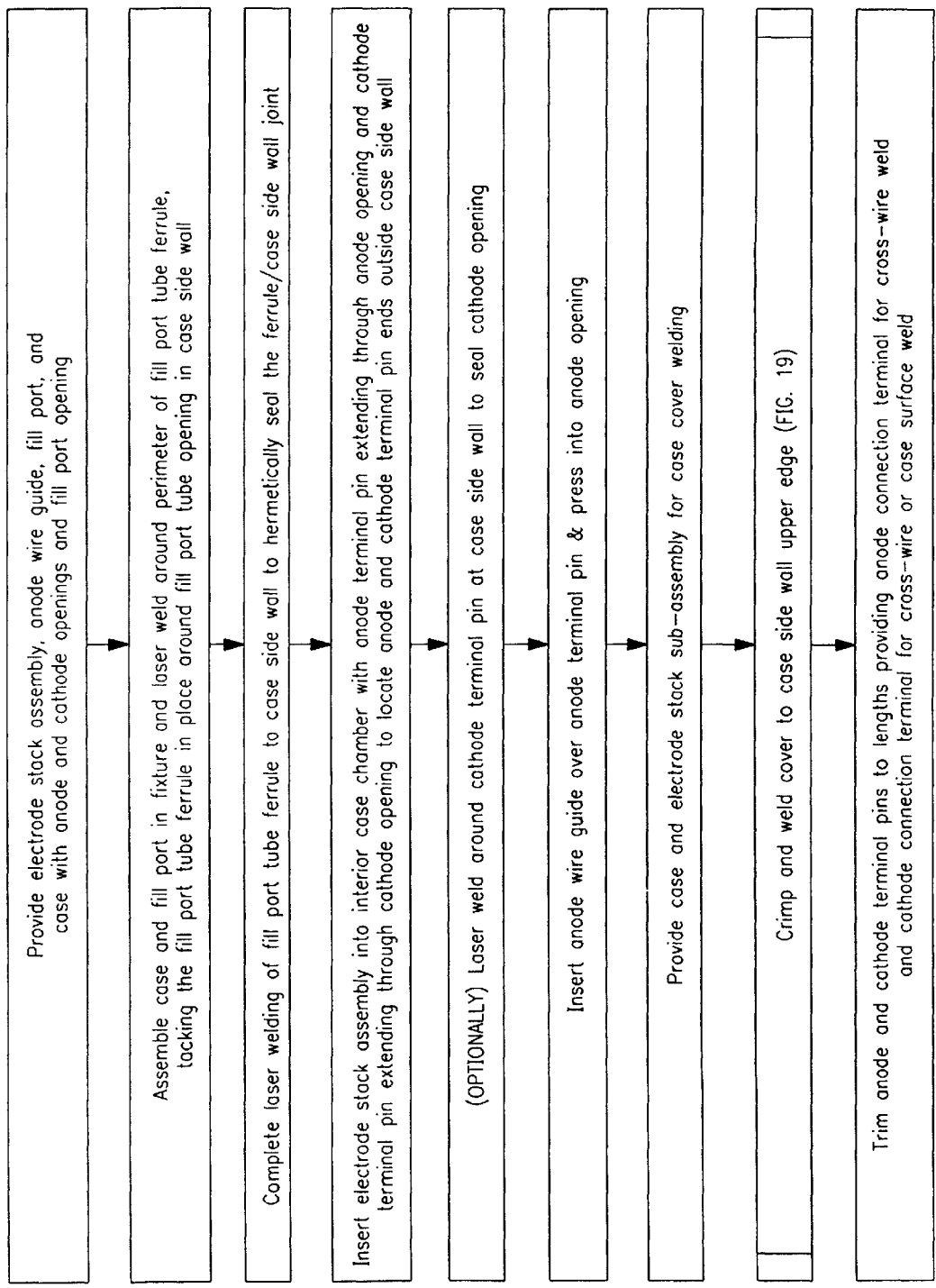
FIG. 18 is a flow chart of one method for making a case sub-assembly of a capacitor incorporating the present invention.

FIG. 17 shows a flow chart corresponding to a further method for making tab interconnections and feedthrough connections. In this method, anode feedthrough 120 and cathode feedthrough 125 have no coiled portions. Gathered anode tabs 232 and gathered cathode tabs 233 are gathered and trimmed, followed by the basal portions of anode and cathode feedthroughs 120 and 125 being placed near to gathered anode tabs 232 and gathered cathode tabs 233, respectively. The basal portions of feedthroughs 120 and 125 are then joined to gathered anode tabs 232 and gathered cathode tabs 233, respectively, most preferably by ultrasonic welding means.

In yet another method, the basal portions of feedthroughs 120 and 125 are flattened to facilitate welding to gathered anode and cathode tabs 232 and 233 (as also shown, for example, in FIGS. 23(*a*) and 24(*a*). In still another method, the basal portions of feedthrough pins 130 and 135 are formed such that they engage gathered anode tabs 232 or gathered cathode tabs 233 around the periphery of the tabs by means other than coiling. For example, basal portions 121 and 126 of feedthroughs 120 and 125 may be "flag shaped," and the flag portions thereof may be wrapped around tabs 232 and 233. In yet other attachment methods, feedthrough pins 130 and 135 may be attached to anode and cathode tabs 232 and 233 with resistance welds, cold welds, brazing, friction welds, or an additional feedthrough component such as a crimping sleeve may capture and join tabs 232 and 233 for providing electrical and mechanical connections thereto.

It has been discovered that the processes of forming electrical connections between gathered tabs 232 and 233 and feedthrough coil assemblies 120 and 125 can introduce undesirable stress on the individual tabs 176 and 195. The resultant strain induced in those tabs has further been found to manifest itself as tears in cathode layer 175 at the base of cathode tab 176, or as fractures in relatively low strength cold welds 205 or 210 within anode sub-assembly 170. One advantage of the coiled portions of feedthroughs 120 and 125 is that they can provide strain relief between feedthrough pins 130 and 135 and gathered tabs 232 and 233. Thus, the strain relief features of feedthroughs 120 and 125 help minimize or eliminate undesirable stress in feedthrough connections.

Table 2 sets forth optimized, preferred processing parameters under which various components of capacitor 265 are laser welded to one another. The parameters set forth in Table 2 correspond to those for a Model No. JK702H pulsed Nd:YAG laser welding system having hard optic beam delivery manufactured by Lumonics Laserdyne of Eden Prairie, Minn. Table 3 sets forth a range of parameters under which the same type of laser welding system provides acceptable weld characteristics.

TABLE 2

Optimized Nd YAG Laser Welding Parameters

Optimized Laser Welding Parameters*

| Weld Type | Energy per Pulse (Joules/ pulse) | Pulse Frequency (Hertz) | Feed Rate (inches/ min) | Pulse Width (msec) | Argon Cover Gas (SCFH) |
|---|---|---|---|---|---|
| Fill port Ferrule to Case Tack 1 | 13.5 | 4.5 | 3 | 5 | 35 |
| Fill port Ferrule to Case Weld | 15 | 15 | 2 | 6 | 35 |
| Anode Feedthrough Tabs | 8 | 10 | 2 | 5 | 35 |
| Cathode Feedthrough Tabs | 4 | 10 | 2 | 5 | 35 |
| Cover to Case | 7.5 | 40 | 6 | 5.4 | 60 |
| Fill Tube Seal | 13.5 | 15 | 4 | 7 | 30 |

*Lumonics JK702H Nd:YAG laser having an initial beam diameter of approximately 1.0 inch (2.54 cm) passing through a final focusing lens with a 146 mm focal length (purchased having "160 mm lens", actual fine focal point measured was 146 mm) and a spot size at the joint surface of 0.022 inch (0.560 mm) diameter. The cover gas was coaxial. It will be understood that variations respecting the manufacturer of the laser, beam delivery optics, the initial beam size, final focusing lens, spot size of the beam and the like may be made.

TABLE 3

Generalized Nd:YAG Laser Welding Parameters

Optimized Laser Welding Parameters*

| Weld Type | Energy per Pulse (Joules/ pulse) | Pulse Frequency (Hertz) | Feed Rate (inches/ min) | Pulse Width (msec) | Argon Cover Gas (SCFH) |
|---|---|---|---|---|---|
| Fill port Ferrule to Case | 2–15 | 3–30 | 1–5 | 3.5–8 | 30–60 |
| Feedthrough Tabs | 1–10 | 1–10 | 1–7 | 3.5–8 | 30–60 |
| Cover to Case | 5–25 | 10–40 | 1–7 | 3.5–8 | 30–60 |
| Fill Tube Seal | 8–20 | 5–20 | 1–10 | 3.5–8 | 30–60 |

*Lumonics JK702H Nd:YAG laser having an initial beam diameter of approximately 1.0 inch (2.54 cm) passing through a final focusing lens with a 146 mm focal length (purchased having "160 mm lens", actual fine focal point measured was 146 mm) and a spot size at the joint surface of 0.022 inch (0.560 mm) diameter. The cover gas was coaxial. It will be understood that variations respecting the manufacturer of the laser, beam delivery optics, the initial beam size, final focusing lens, spot size of the beam and the like may be made.

As employed in the specification and claims hereof, the term "laser welding" means, but is not necessarily limited to, a method of welding wherein coherent light beam processing is employed. Coherent light beam processing include electron beam or laser welding methods (e.g., Nd:YAG, $CO_2$ processes) having hard or fiber optic beam delivery in pulsed, continuous, or q-switched modes. Other welding processes, such as micro metal inert gas welding and micro plasma welding processes, may be substituted for coherent light beam welding.

FIG. 10 shows an exploded top perspective view of capacitor 265 of FIG. 9 in a partially assembled state, again with the connector block 145 depicted as a discrete part for convenience of illustration. FIG. 18 shows a flow chart of one method of making case sub-assembly 108 that the cover 110 is attached to pursuant to the steps illustrated in FIG. 19. In the preferred embodiments, case 90 and cover 110 are formed of aluminum and are electrically connected to the cathode layers, and where case 90 and cover 110 are at the same electrical potential as the cathode layers, i.e., at negative potential, or is not connected to either the anode or cathode potentials.

First the electrode stack assembly 225, the fill port 107 and the case 90 having the anode and cathode openings 142 and 143 and the fill port opening 139 through the side wall 92 are provided. In the next two steps of FIG. 19, the fill port ferrule 105 is then laser welded around the fill port opening 139. The electrode stack assembly 225 is inserted into the interior case chamber with the anode feedthrough or terminal pin 130 extending through the anode opening 142 and the cathode feedthrough or terminal pin 135 extending through the cathode opening 143. Optionally, the gap between the cathode terminal pin 135 and the edge of the cathode opening 143 is laser welded to ensure that the case 90 is at cathode potential. However, this step can be eliminated when it does not matter what potential the case 90 is to be at, and epoxy is employed to seal the gap from leakage of electrolyte.

The external end of the anode terminal pin 130 is passed through the lumen of the anode wire guide 95 which is then pressed into the anode opening 142. Wire guide 95 is electrically insulating and centers anode feedthrough pin 130 within the inside diameter opening of the anode opening 142 to permit anode pin 130 to be spaced from and electrically insulated from the inside surface of case 90. The size tolerances of the wire guide 95, the feedthrough pin 130 and the anode hole 142 are such that the wire guide 95 can be fitted into the hole 142 and the feedthrough pins 130 fitted through a centrally disposed hole in the wire guide 95. The assemblies are not hermetically sealed with the case side wall 92, and it necessary to effect a hermetic seal to prevent loss of electrolyte. In accordance with one aspect of the present invention, the seal is effected by formation of the epoxy droplet connector block 145 in accordance with the method of FIG. 20. Epoxy seeps into the gaps between the wire guide 95, the feedthrough pin 130 and the anode hole 142.

Wire guide 95 most preferably contains an annular, ramped, or "snap-in" feature formed integrally therein. This feature prevents wire guide 95 from being pushed out of anode opening 142 during handling, but is most preferably formed such that insertion of wire guide 95 into anode opening 142 may occur using force sufficiently low so as not to damage case 90 during the inserting step. Wire guide 95 may be formed from any of a wide variety of electrically insulating materials that are stable in the environment of an electrolytic capacitor. In one preferred embodiment, the material from which wire guide 95 is made is an injection molded polysulfone known as AMOCO UDEL supplied by Amoco Performance Products of Atlanta, Ga. In other embodiments, wire guide 95 may be formed from other chemically resistant polymers such as fluoroplastics (e.g., ETFE, PTFE, ECTFE, PCTFE, FEP, PFA or PVDF), fluoroelastomers, polyesters, polyamides, polyethylenes, polypropylenes, polyacetals, polyetherketones, polyarylketones, polyether sulfones, polyphenyl sulfones, polysulfones, polyarylsulfones, polyetherimides, polyimides, poly(amide-imides), PVC, PVDC-PVC copolymers, CPVC, polyfurans, poly(phenylene sulfides), epoxy resins, silicone elastomers, nitrile rubbers, chloroprene polymers, chlorosulfonated rubbers, polysulfide rubbers, ethylene-polypropylene elastomers, butyl rubbers, polyacrylic rubbers, fiber-reinforced plastics, glass, ceramic and other suitable electrically insulating, chemically compatible materials.

As used in the specification and claims hereof, the foregoing acronyms have the following meanings: the acronym "ETFE" means poly(ethylene-co-tetrafluoroethylene); the acronym "PTFE" means polytetrafluoroethylene; the acronym "CTFE" means poly(ethylene-co-chlorotrifluoroethylene); the acronym "PCTFE" means polychlorotrifluoroethylene, the acronym "PEP" means fluorinated ethylene-propylene copolymer; the acronym "PFA" perfluoroalkoxy fluoropolymer, the acronym "PVDF" means polyvinylidene fluoride; the acronym "PVC" means polyvinyl chloride; the acronym "PVDC-PVC" means polyvinylidene chloride-polyvinyl chloride copolymer, and the acronym "CPVC" means chlorinated polyvinyl chloride.

The case assembly and the cover 110 are then provided for attachment of the cover 110 to the side wall upper edge pursuant to the steps of FIG. 19 as described below. Finally, in FIG. 18, the ends of the cathode and anode terminal pins 130 and 135 are trimmed if necessary.

The electrode stack assembly 225 is thereby seated in the interior case chamber 100 of case 90 as shown in FIGS. 11(a) and 11(b). FIGS. 11(a) and 11(b) also show the head space portion of electrode stack assembly 225 (referred to herein as head space 230) is insulated from case 90 and cover 110. The means by which head space insulation may be provided include molded, thermally-formed, die cut, or mechanically formed insulating materials and means, where the materials and means are stable in the environment of an electrolytic capacitor. Suitable materials from which head space insulators may be formed include all those listed hereinabove respecting materials for forming wire guide 95. Another means of providing head space insulation is to wrap electrically insulating tape, similar to wrapping tape 245, around head space 230 to prevent the anode or cathode terminals from contacting case 90 or cover 110 or each other.

Figure 19:
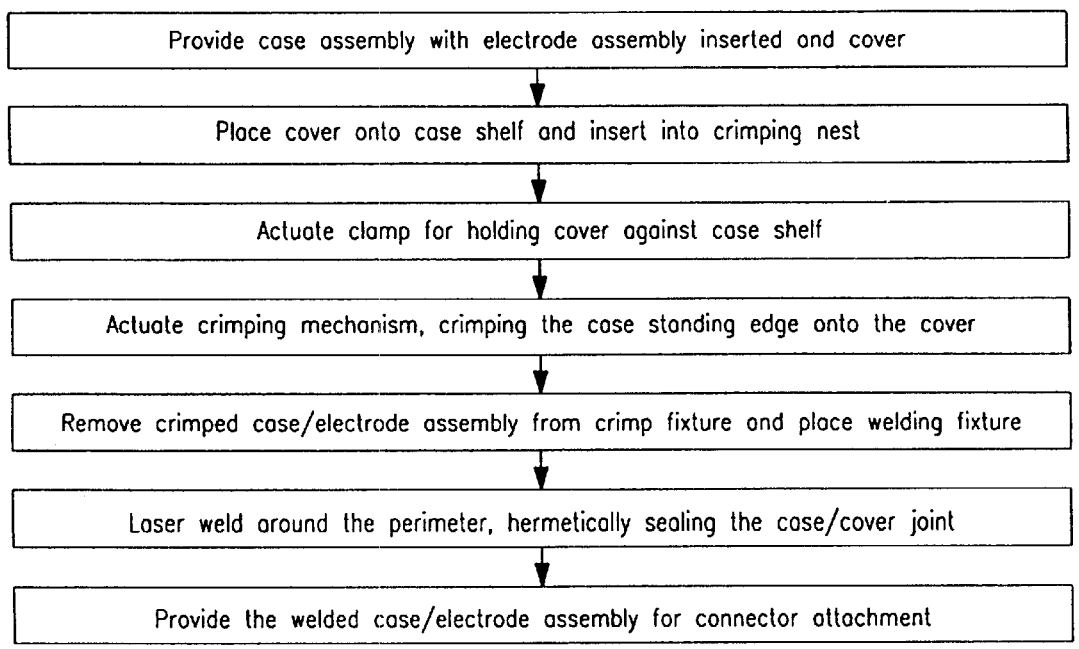
FIG. 19 is a flow chart of one method for sealing a case and cover of a capacitor incorporating the present invention.

FIG. 19 shows an expanded flow chart of the step in FIG. 13 of welding the cover 110 to the case 90 and effecting a hermetic seal therebetween as described in greater detail in the above-referenced parent application Ser. No. 09/103, 876. Case sub-assembly 108 is provided with electrode stack assembly 225 inserted into interior case chamber 100 of case 90 and the anode and cathode tab/feedthrough connections completed as described above. Cover 110 is disposed atop an upper edge 94 formed in the side wall 92 of case 90. In one case side wall upper edge configuration, a raised portion of the upper edge extends about 0.014 inches (0.35 mm) above an upper surface 112 of cover 110 when cover 110 is placed on the upper edge 94. The assembly is placed within a crimping mechanism or nest, and a clamp is actuated to hold cover 110 against upper edge 94. The crimping mechanism is actuated to crimp or fold the raised edge portion onto, along or over upper surface 112 of cover 110.

In another preferred method, crimping of the raised portion of upper edge 94 is accomplished using a die cut to the shape of case 90 and further having angled or ramped side walls for engaging and pressing inwardly the raised portion over upper surface 112 of cover 110. A crimp may also be formed with a moving crimp apparatus that travels around the perimeter of case 90 while continuously crimping the raised portion over upper surface 112 of cover 110. The foregoing methods may be readily adapted to permit the crimping or folding of the edge of cover 110 downwardly over outer side wall 92.

Crimping of the raised portion onto cover 110 or the cover edge onto the side wall upper edge 94 provides several advantages. First, laser welding of cover 110 to case 90 may be accomplished using relatively simple tooling, thereby resulting in short process times. Laser welding often provides a bottleneck in manufacturing process flow when components such as case 90 and cover 110 typically must be aligned precisely respecting one another. The elimination of such alignment steps during the laser welding process has been discovered to help eliminate manufacturing process bottlenecks. Folding or crimping raised edge portion or outer cover edge prevents a laser beam from entering the interior of capacitor 265. Instead, a laser beam is forced to couple with the material of case 90 and cover 110 to thereby induce melting. It was discovered that joints not having crimps forming at least a portion thereof may permit a laser beam to damage components inside capacitor 265.

Another advantage of the crimped joint is that the crimp provides additional metal in the weld zone. Aluminum, having a high thermal expansion coefficient, is sensitive to cracking upon rapid cooling from the high temperatures characteristic of welding processes. The additional metal provided by the crimp decreases cracking sensitivity in the joint between the cover and the case upper edge.

Crimped case 90 and cover 110 are next removed from the crimp fixture and placed in a welding fixture. A laser weld is made in the joint formed between the cover edge and the case upper edge 94 to hermetically seal case 90 to cover 110. Table 2 sets forth an optimized set of parameters under which the crimped case/cover joint may be sealed using a pulsed Nd:YAG laser welding system. Table 3 sets forth a generalized range of conditions under which the same laser welding system provides acceptable results.

Returning to the final step of FIG. 18, the anode and cathode terminal pins are then trimmed to an appropriate length to provide anode and cathode connection terminals of at least two types. FIGS. 11(*a*) and 11(*b*) show preferred attachment methods for attaching the exposed anode wire end 150*a* to the an anode connection terminal along the side of anode feedthrough pin 130 and the exposed cathode wire end 150*b* to the a cathode connection terminal along the side of cathode feedthrough pin 135 or to the exterior surface of the case side wall 92 adjacent to the trimmed or ground down end of the cathode terminal pin 135. FIGS. 11(*a*) and 11(*b*) also show the epoxy droplet connector block 145 (shown in phantom outline) which is formed in situ on the case wall 92 and encapsulates these connections. The steps of attaching the exposed wire ends 150*a* and 150*b* to the feedthrough pins 130 and 135, respectively, and forming the epoxy droplet connector block 145 are also shown in the flow chart of FIG. 20.

In preferred embodiments, the electrical connections of the exposed wire ends 150*a* and 150*b* to the feedthrough pins 130 and 135, respectively, are made using techniques such as ultrasonic welding, resistance welding and laser welding. In such joining techniques, the joint geometry is preferably a cross-wire weld, i.e. at right angles, between feedthrough wire 130 and 135 and the exposed ends 150*a* and 150*b* of harness lead wires 151 and 152, respectively. However, the connection may be made using the crimping tubes and methods described in detail in the above-referenced parent application Ser. No. 09/103,876, particularly with the connector block and attachment methods disclosed therein. Table 4 sets forth an optimized set of parameters of the cross-wire and alternative surface welds for resistance welding of stranded wire exposed ends 150*a* and 150*b* to the anode and cathode a connection terminals:

TABLE 4

Generalized Resistance Welding Parameters (Single or Dual Pulse)

| Weld Type | Resistance Welding Parameters* | | | | | | | |
|---|---|---|---|---|---|---|---|---|
|  | a. | b. | c. | d. | e. | f | g. | h. |
| Cross Wire | 0–20.0 | .250–.550 | 0–15 | 8.0–30.0 | .500–1.500 | 1.0–7.0 | 1.5–8.5 | 20–50 |
| Wire to Case | 0–20.0 | .500–.750 | 0–15 | 8.0–30.0 | .500–2.30 | 1.0–7.0 | 1.5–8.5 | 20–50 | a. 1$^{st}$ pulse width in milliseconds
b. 1$^{st}$ pulse current in KA
c. Cooling cycle in milliseconds
d. 2$^{nd}$ pulse width in milliseconds
e. 2$^{nd}$ pulse current in KA
f. Weld head force in lbs
g. Follow-up weld head force in lbs.
h. Argon Cover Gas in SCFH
*Unitek Miyachi HF 25 high frequency inverter with a Unitek Miyachi 302H linear actuated electromagnetic weld head with a Unitek Miyach C350 weld head controller. Electrodes: oversized class 2 copper lower electrode, molybdenum, copper/tungsten or HD-17 alloy upper electrode .030"–.060" in diameter.

Figure 20:
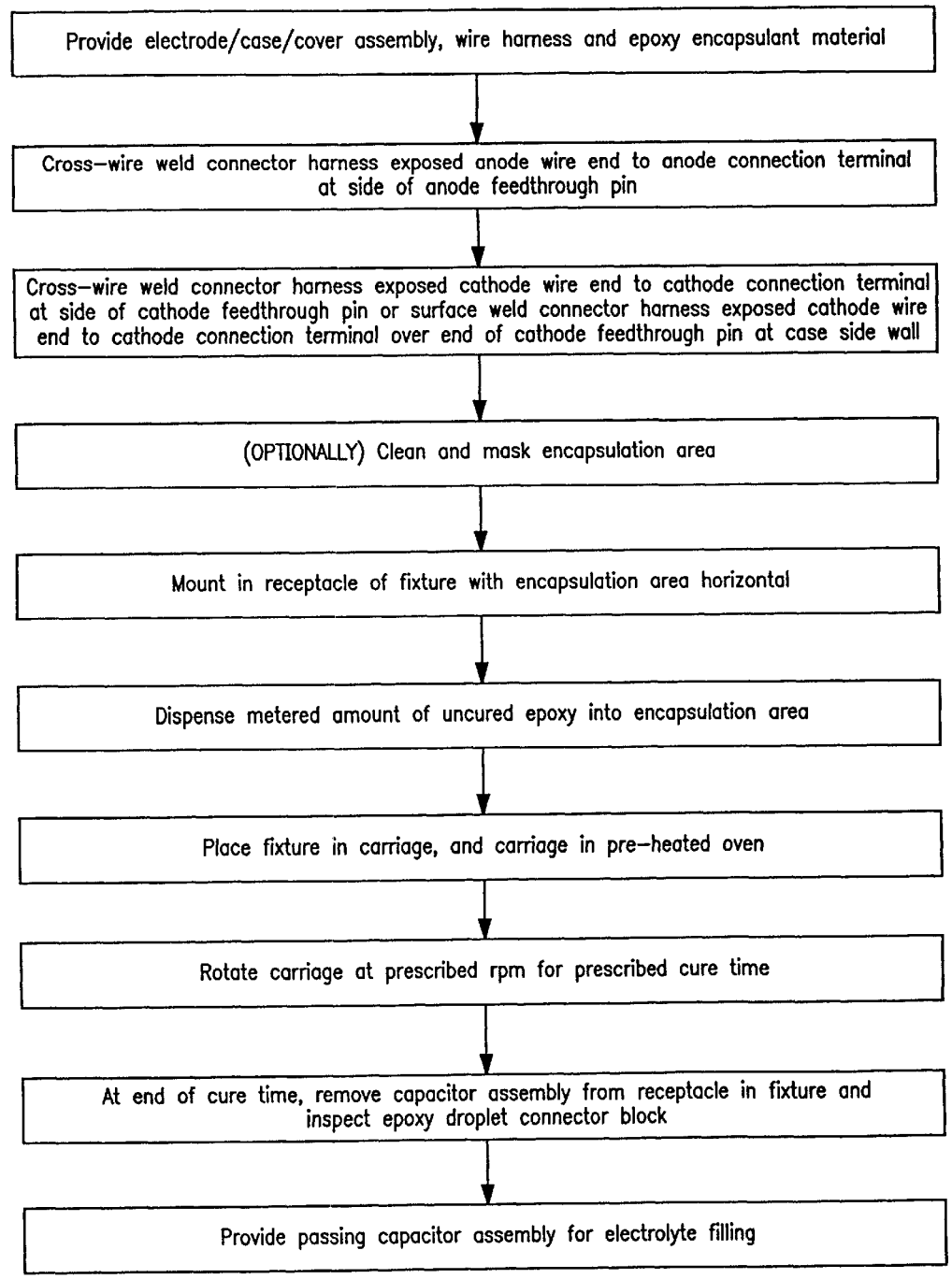
FIG. 20 is a flow chart of one method for sealing a feedthrough of a capacitor incorporating the present invention.

In FIG. 20, the epoxy droplet connector block 145 is formed after the electrical connections are completed in a manner also illustrated in FIGS. 21(*a*)–21(*c*). In general, after the electrical connections with the wire harness are made, the encapsulation area is prepped, a metered amount of relatively viscous liquid epoxy is applied in a droplet over the electrical connections in the encapsulation area, and the epoxy is cured in an oven while the capacitor assembly is rotated slowly. The controlled temperature and the slow rotation allow the epoxy to flow and seep into any cavities around the feedthrough components and electrical connections, to release any gas that would form bubbles and to form a bulbous, smooth, glossy exterior surface having a somewhat hemispheric shape that is consistent from one capacitor to the next.

In FIG. 21(*a*), the electrical connections are completed by cross-wire welding the wire harness wire ends 150*a* and 150*b* to the anode and cathode terminal pins 130 and 135 as described above. In FIG. 21(*b*), the encapsulation area 98 and the electrical connections are prepped by cleaning, and the masking tape 99 is optionally applied to the side wall 92 to limit epoxy flow along the flat side wall surface and to provide a neat and consistent edge of the epoxy droplet that is formed over the encapsulation area 98. It is not necessary to mask all four edges of the encapsulation area 98, because the other edges are bounded by the curved case edges, and epoxy flow over those case edges is inhibited by surface tension of the liquid epoxy that cures as the capacitor assembly is rotated.

The metered amount of epoxy that forms the connector block 145 is applied to the encapsulation area 98 as shown in FIG. 21(*c*), while the encapsulation area surface is disposed horizontal in a receptacle of a fixture that may have a plurality of such receptacles for holding a plurality of capacitor assemblies. Then, the fixture holding the capacitor assembly or assemblies is placed in carriage that is coupled to a motorized drive that rotates the carriage at a predetermined rate. The rotation of the carriage and fixture rotates each capacitor assembly about the axis A—A of FIG. 21(*c*) (or any other preferred axis) while in the temperature controlled oven. The elevated temperature lowers the viscosity of the epoxy allowing the epoxy to assume a minimum volume (and surface area) as governed by gravity, epoxy-aluminum surface energy (wetting) and epoxy surface tension. The epoxy droplet connector block 145 so formed provides strain relief to feedthrough pins 130 and 135 and to the harness wire electrical connections. The epoxy provides an epoxy seal between wire guides 140 and 141, case 90 and ferrules 95 and 100.

The epoxy cures within 30 minutes in an oven operating between 85°–105° Centigrade (e.g., 90° C.) with the carriage rotating at about two rpm. Moreover, we have found that the masking tape 99 is not necessary to confine the epoxy flow as long as there is no failure in the rotation of the carriage in a position that would allow epoxy flow away from the area.

After curing is completed, the capacitor assembly so formed is removed from the receptacle of the carriage, the masking tape 99 is removed (if applied earlier), and the epoxy droplet connector block 145 is inspected. The overall shape, the droplet edge, and the coverage of the internally encapsulated components must meet prescribed standards.

The method by which the epoxy droplet connector block 145 is made provides excellent electrical insulation of the feedthrough pins 130, 135 and the wire ends 150a, 150b. The method provides a predictable, uniform, reliable and attractive connector block 145 that exhibits a high quality hermetic seal.

The epoxy employed to form the epoxy droplet connector block 145 is most preferably chemically resistant to the electrolyte employed in capacitor 265 and adheres well to surrounding surfaces. Adhesion promotion (such as by chemical deposition, etching, corona, ion gun, or plasma treatment) of each polymeric wire guide (or a polymeric case side wall, if one is substituted for the above-described aluminum case) may be employed to maximize the reliability of capacitor 265. In a preferred method, an epoxy is employed which has few or no voids and cracks and completely or substantially completely adheres to the surrounding pin, ferrule wall and wire guide components, Filling of the ferrule hole with sealing epoxy may be accomplished in several ways, depending largely on the viscosity and wetting angle (surface energy) of the epoxy selected. A balance in wetting angle and viscosity characteristics of the epoxy has been found to be desirable. More particularly, it is desired that the epoxy be thin enough to fill without voids forming and to wet the surface, yet thick or viscous enough not to escape around or through the wire guides or around the capacitor case edges and masking tape bounding the encapsulation area 98.

One suitable epoxy comprises an aliphatic epoxy such as CIBA-Geigy Araldite 2014. Other suitable potting adhesives include chemically resistant thermoplastic hot melt materials such as polyamides, polyesters, polyurethanes, epoxies, and polyethylene-vinyl acetates, UV curable resins such as acrylates and methacrylates, and other thermosetting resins such as aliphatic and aromatic epoxies, silicones, polyamides, polyesters and polyurethanes. Many suitable potting adhesives may be thermally cured or cured with ultraviolet light. A focused IR procedure may be employed in some instances to minimize cure time and localize heat. A transparent epoxy droplet connector block 145 is depicted in FIG. 21(c), but the epoxy material may be opaque.

Figure 22B:
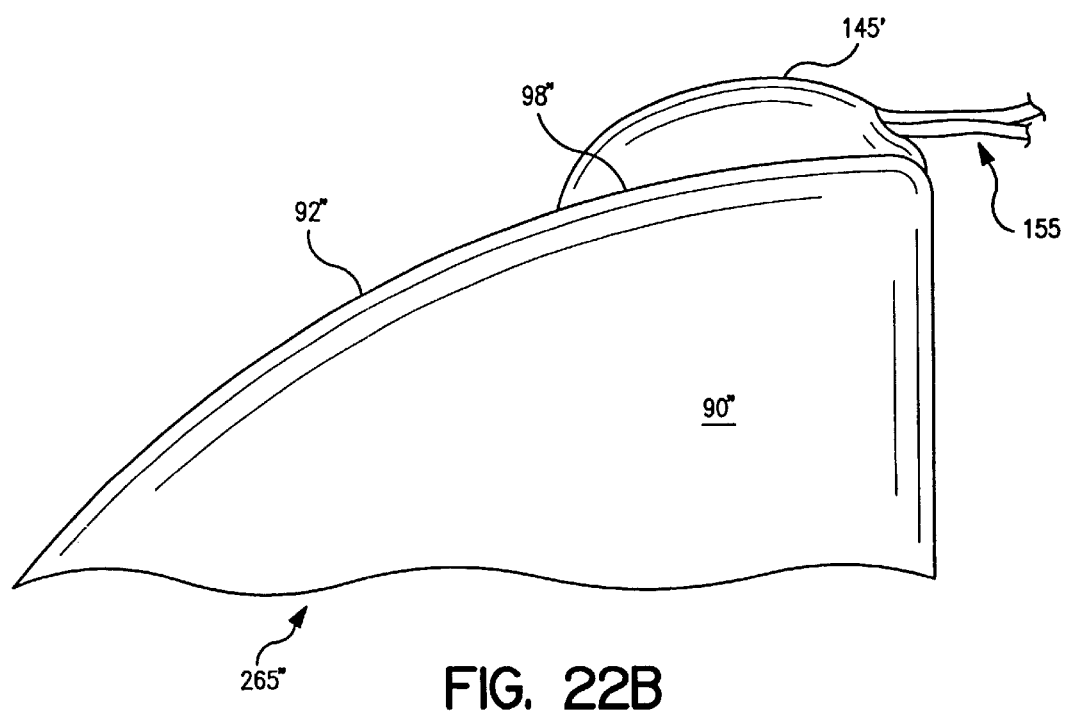

Further case negative or case neutral capacitor embodiments formed with epoxy droplet connector blocks 145' are depicted in FIGS. 22(a)–22(b) through 24(a)–24(b). The method of making the electrical connections and forming the epoxy droplet connector block 145' follows the steps of FIG. 20 as described above. The capacitor cases 90' and 90" and the mating covers and interior disposed electrode stack assembly of these case negative embodiments are somewhat smaller and more hemispheric than the above-described case neutral embodiments. The encapsulation area 98' of the embodiment depicted in FIG. 22(a) follows the curvature of the side wall 92', whereas the encapsulation area 98" of the embodiment depicted in FIG. 22(b) is in a flattened portion of the side wall 92". FIGS. 23(a)–23(b) and 24(a)–24(b) depict alternative ways of making case neutral or case negative electrical connections in the embodiment of FIG. 22(a), but it will be understood that these and equivalent forms of making case negative connections can be employed in the embodiment of FIG. 22(b). Moreover, these and equivalent forms of making case negative connections can be employed to change the above-described case neutral capacitors into case negative capacitors.

FIGS. 23 (a) and 24(a) shows one embodiment of the electrical connections of the gathered anode tabs 232 with the wiring harness 155 within the epoxy droplet connector block 145'. An anode feedthrough pin 120' is supported in anode hole or opening 142' and electrically insulated from the case side wall 92' by an electrically insulating, ring-shaped, guide 95'. These anode feedthrough components may be formed and assembled to the case side wall 92' in the manner described above or can be formed as a discrete feedthrough, wherein the ferrule is welded to the case side wall 92' as a unit and then connected to the gathered anode tabs 232 and the exposed wire end 150a. The anode feedthrough pin 120' is coupled at an internal end to the gathered anode tabs 232. The externally disposed end of the anode feedthrough pin 120' provides an anode connection terminal for connection with the exposed wire end 150a of wire 152 of wiring harness 155 by any convenient method including those described above. The preferred cross-wire weld is illustrated.

Figure 23A:
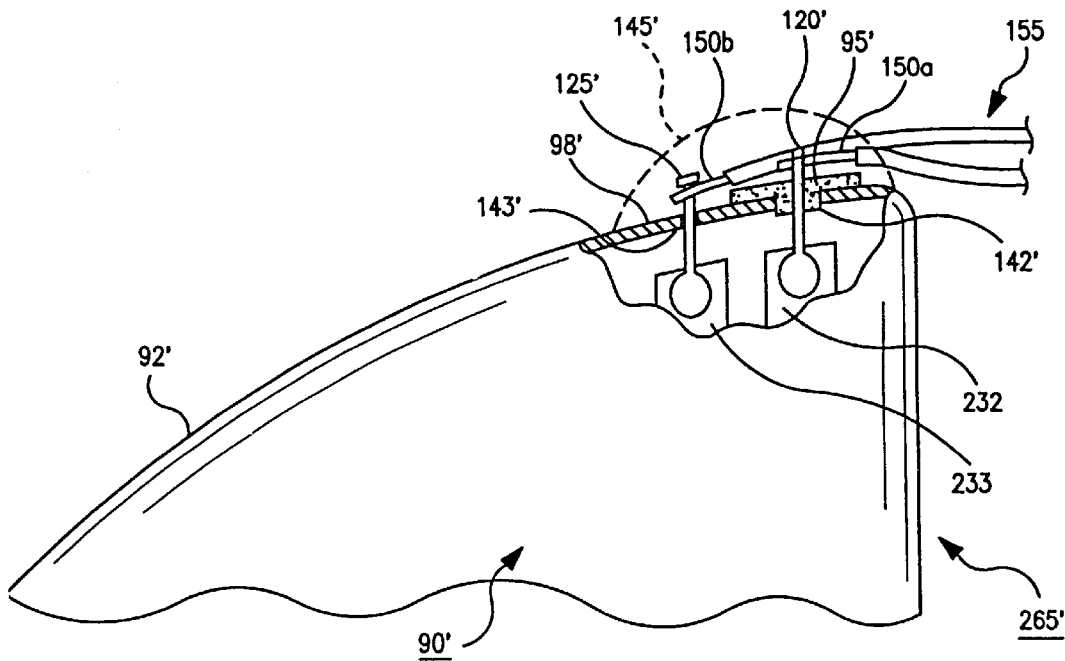
FIG. 23(a) is a side elevation view in partial exposed section illustrating one embodiment of the electrical connections of the gathered anode and cathode tabs with the wiring harness within the epoxy droplet connector block.
Figure 23B:
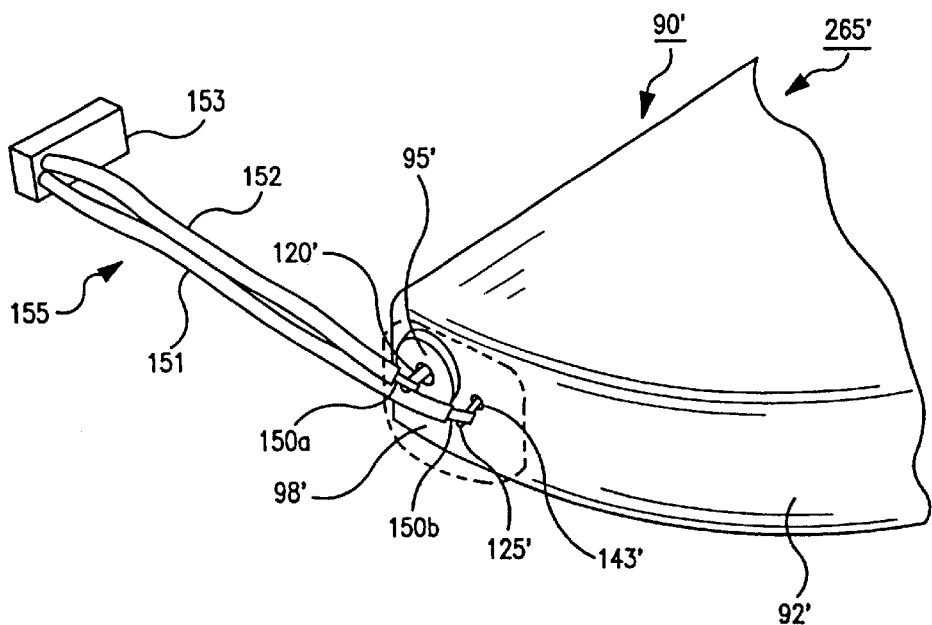
FIG. 23(b) is an end perspective view illustrating the electrical connections of the feedthrough terminal pins of FIG. 23(a) with the wiring harness within the epoxy droplet connector block.

FIGS. 23(a) and 23(b) illustrate one manner of making the connection of the gathered cathode tabs 233 with the wiring harness 155 within the epoxy droplet connector block 145' and for providing a cathode connection terminal. A cathode pin 125' is coupled at an internal end to the gathered cathode tabs 233 and at an external end to the exposed wire end 150b of wire 151 of wiring harness 155 by any convenient method including those described above. The preferred cross-wire weld is illustrated. In this embodiment depicted in FIGS. 23(a) and 23(b), the cathode pin 125' is simply extended through the cathode opening 143', and it is not necessary to weld any remaining gap between the cathode pin 125' and the edge of cathode opening 143' closed, since that gap will be filled with the flowing epoxy. Thus, the gathered cathode tabs 233 may or may not be electrically coupled to the case 90', depending upon whether the cathode pin 125' happens to contact an edge of the cathode opening 143'

Figure 24A:
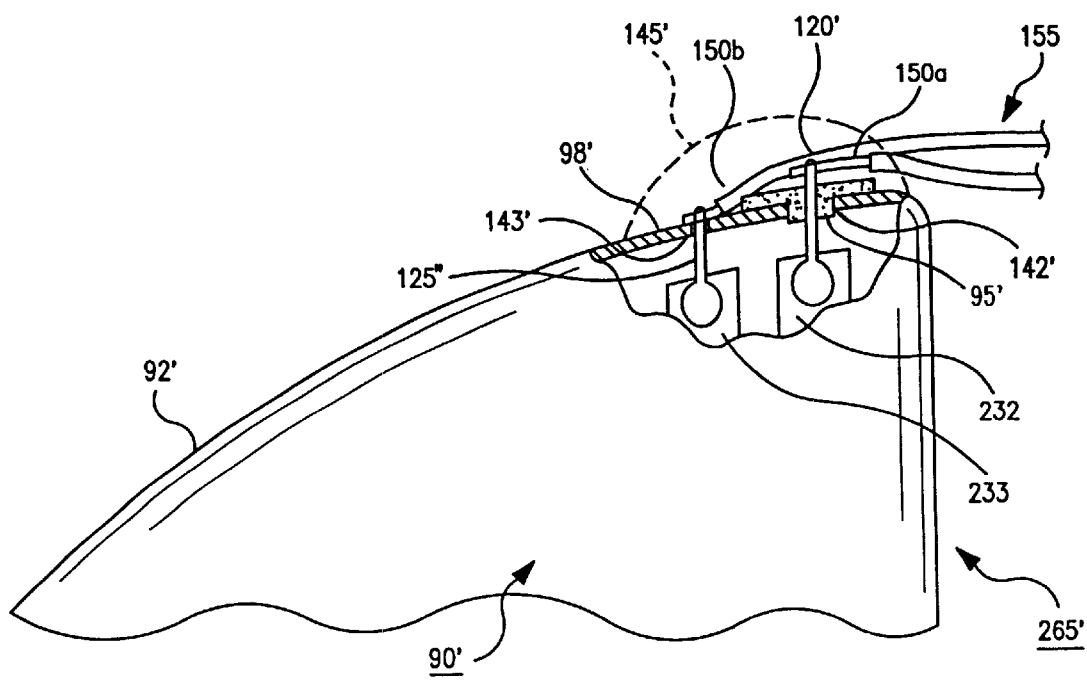
FIG. 24(a) is a side elevation view in partial exposed section illustrating a further embodiment of the electrical connections of the gathered anode and cathode tabs with the wiring harness within the epoxy droplet connector block.
Figure 24B:
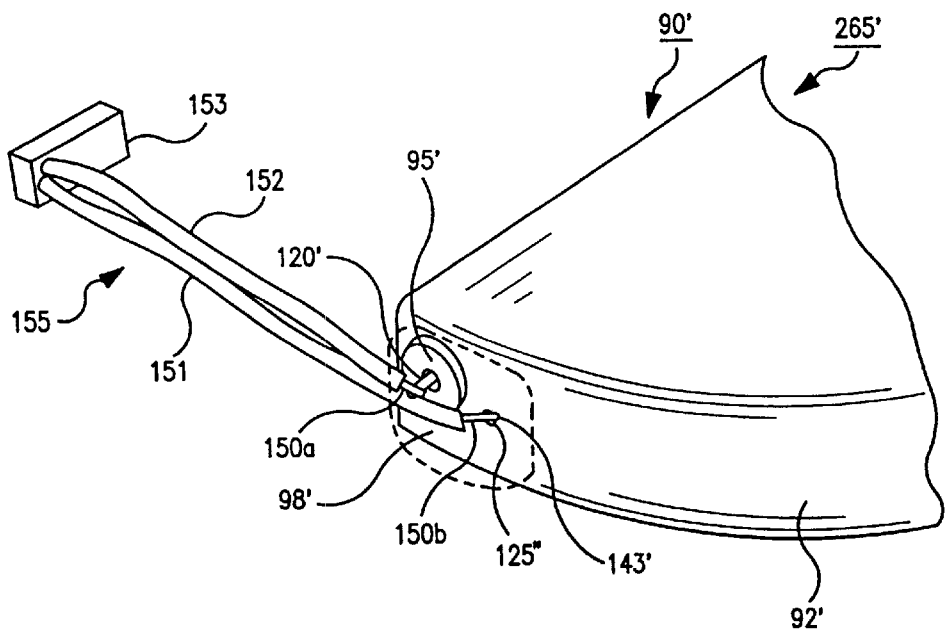
FIG. 24(b) is an end perspective view illustrating the electrical connections of the wiring harness with the anode feedthrough terminal pin and the case of FIG. 24(a) within the epoxy droplet connector block.
Figure 25:
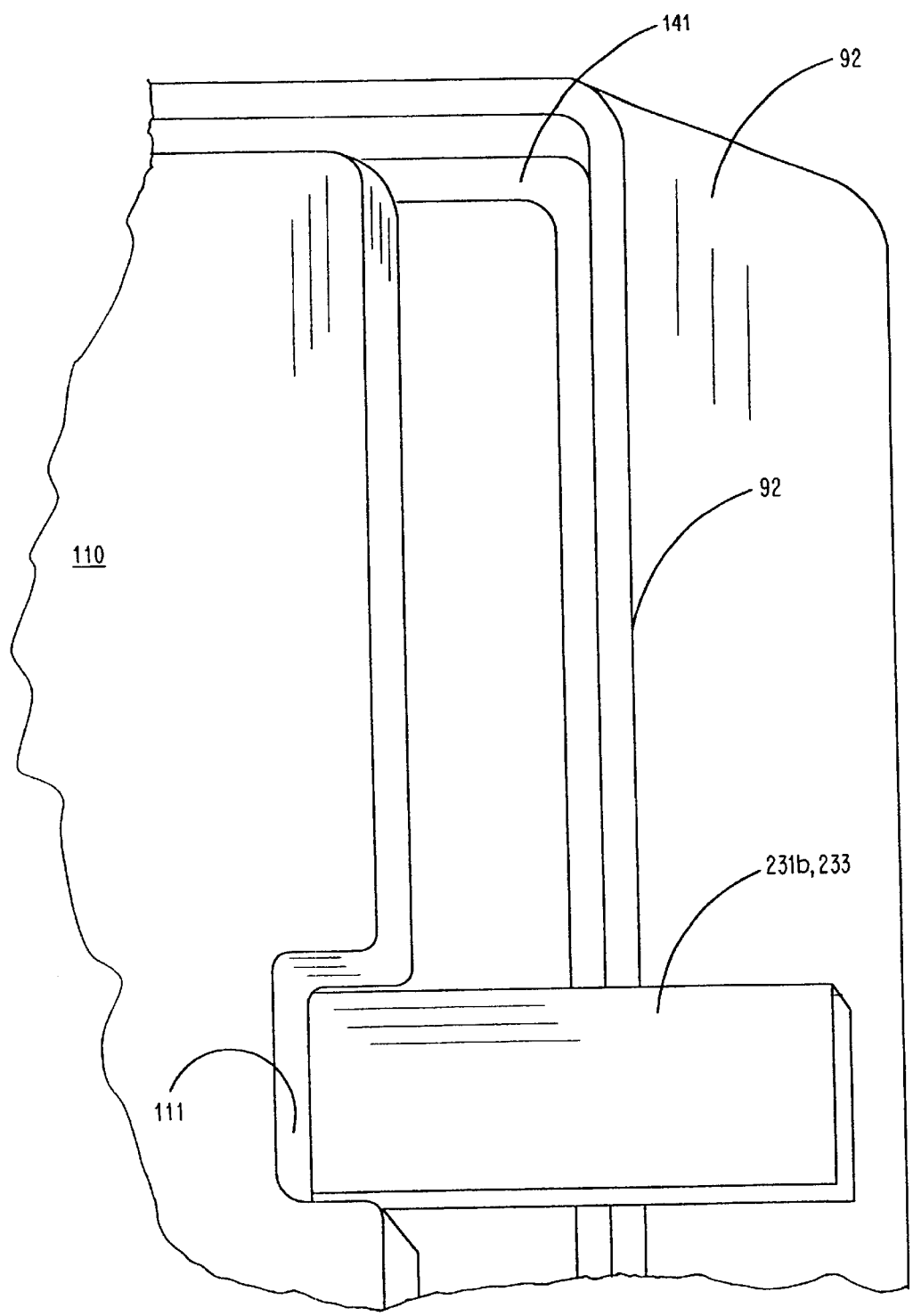
FIG. 25 is a detail view of a cathode terminal passageway comprising a portion of the side wall upper opening edge and a relieved section of the cover edge.

FIGS. 24(a) and 24(b) illustrate a further manner of making the case negative connection of the gathered cathode tabs 233 with the wiring harness 155 within the epoxy droplet connector block 145' and providing a cathode connection terminal. A cathode pin 125' is coupled at an internal end to the gathered cathode tabs 233 and at an external end to the exposed wire end 150b of wire 151 of wiring harness 155 by any convenient method including those described above. The cathode pin 125' is extended through small diameter cathode hole 143' and electrically coupled with the case side wall 92' by application of welding energy that also seals the cathode hole 143'. In this embodiment, the cathode pin 125' is then ground down to the surface of the case side wall 92', and the exposed wire end 150b is welded to that surface at the cathode connection terminal within the encapsulated area 98'. The welding may close the gap between the cathode pin 125' and the edge of cathode opening 143'.

Welding parameters for such surface or wire to case resistance welds are set forth in Table 4 above.

In a further embodiment and variations thereof illustrated in FIGS. 25–30, the cathode terminal passageway comprises a portion of an interior ledge 141 of the side wall upper opening edge 94 having a width and depth depressed below the upper opening edge 94 and a cover edge portion 111 of the cover 110 overlying the portion of interior ledge 141. The anode terminal means may be formed as described above or may simply comprise an anode wire or feedthrough pin 130' having a first anode terminal end 130a' electrically and mechanically connected with the gathered anode tabs 232 and a second anode terminal end 130b' and an insulating spacer 95' within the anode terminal passageway or anode opening 142 for supporting the anode wire or feedthrough pin 130'. The spacer 95' may be formed as a discrete annular insulator part inserted into anode opening 142 or formed in situ surrounding the anode wire or feedthrough pin 130' and electrically insulating it from the case side wall 92 thereby locating an anode connection terminal at the second anode terminal end 130b' exterior to the case side wall 90. The fabrication steps of these embodiments generally follow the steps set forth in FIGS. 13–15, 17, 19 and 20 and substituting FIGS. 29 or 30 for FIG. 18.

Figure 28:
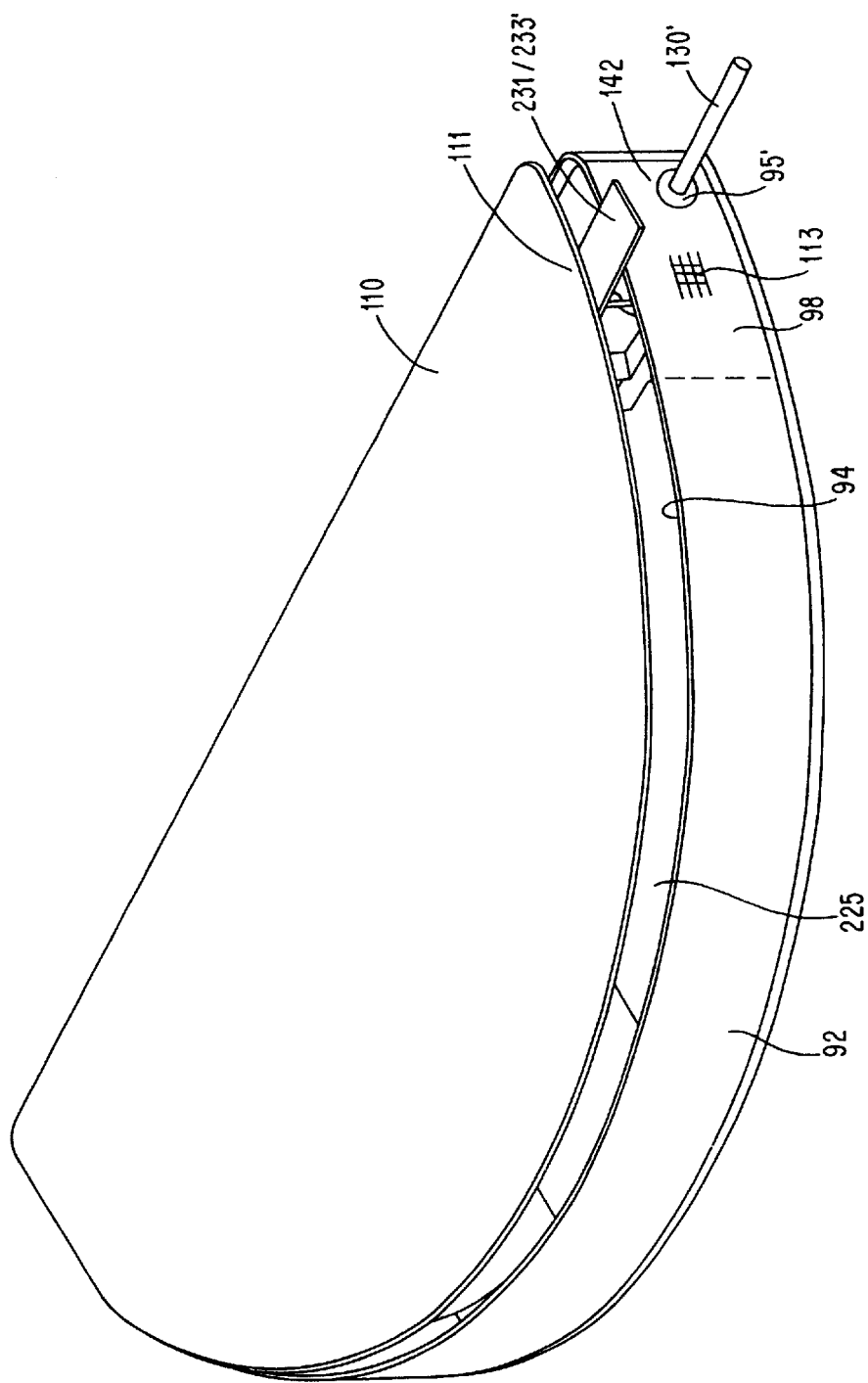
FIG. 28 is a perspective exploded view illustrating the assembly of the cathode terminals illustrated in FIGS. 26 and 27.

In these embodiments, a first cathode terminal end is attached to the gathered anode tabs 233, and the second cathode terminal end is trapped against ledge 141 by the cover 110 when it is sealed against the side wall upper opening edge 94 and the trapped second cathode terminal end. The exposed wire end 150 of the cathode wire of the connector assembly is flush welded to the exterior of the case wall 92 at a defined cathode connection terminal 113 within the encapsulation area 98 as shown in FIG. 28.

Figure 26:
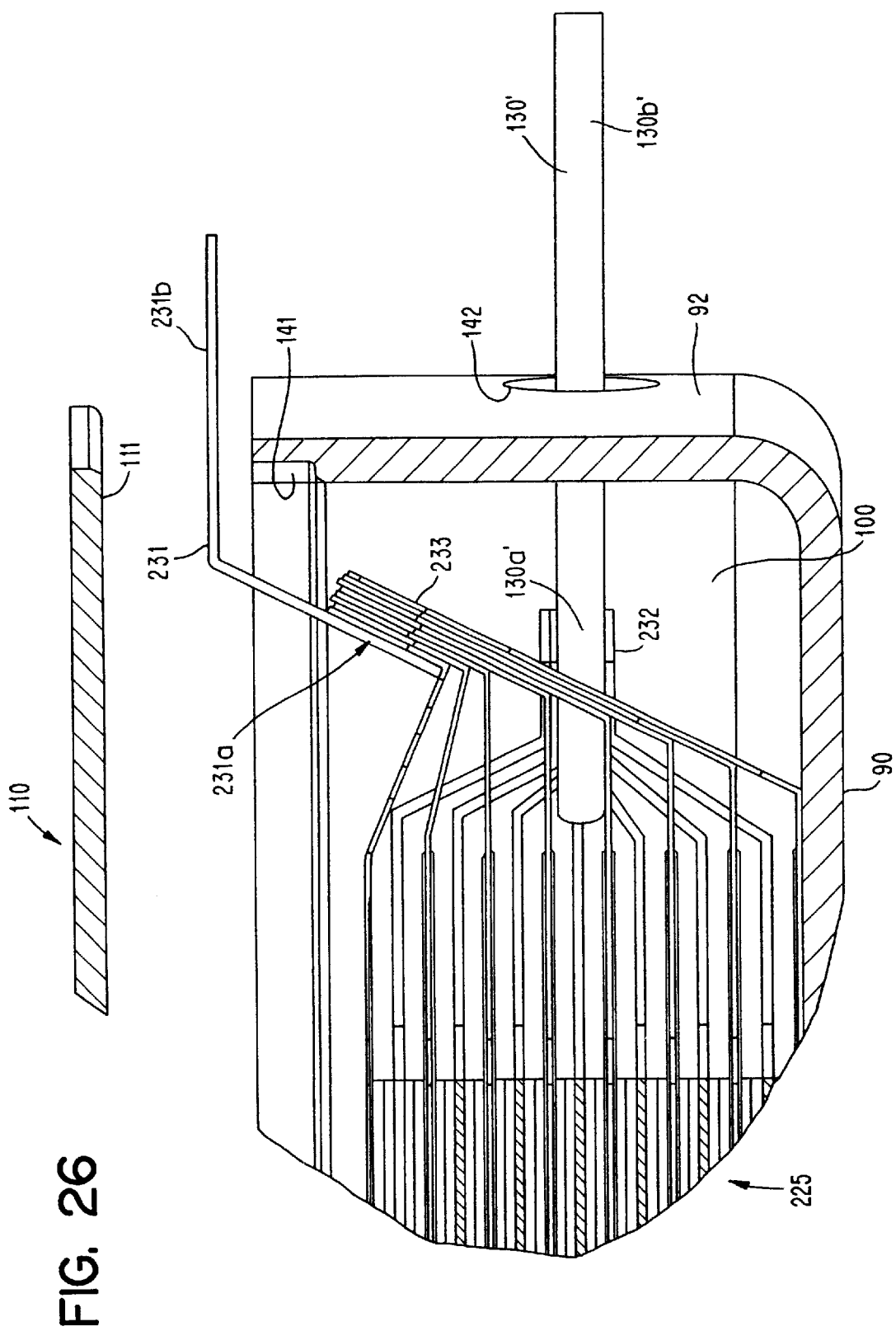
FIG. 26 is a side elevation, cross-section view illustrating a further form of anode and cathode terminals employing a cathode foil trapped between the cover edge and the side wall upper opening edge.
Figure 29:
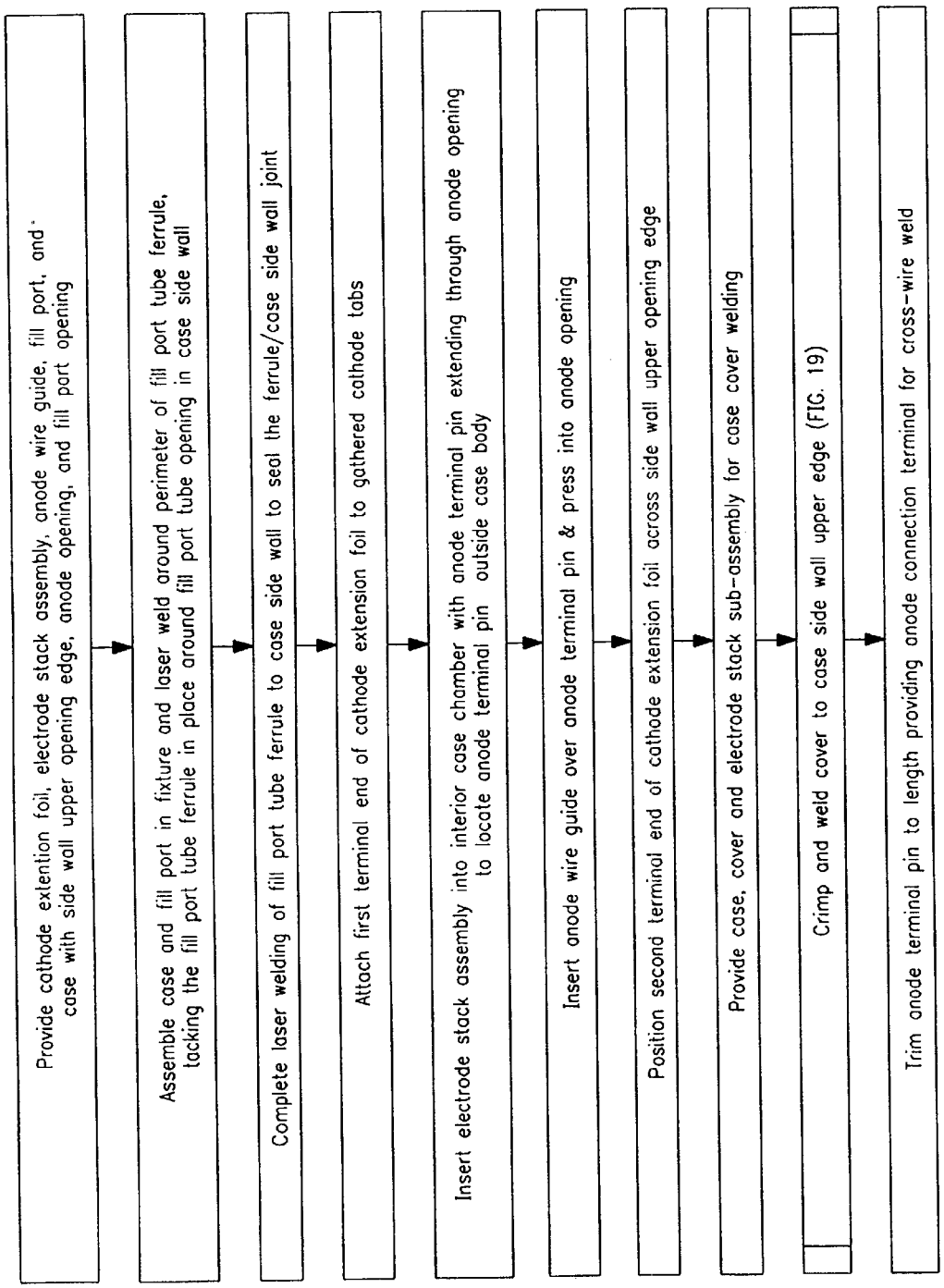
FIG. 29 is a flow chart illustrating the process of making the electrical connections of the cathode terminal illustrated in FIG. 26.

In the first variation of this embodiment depicted in FIGS. 26 and 29, the cathode terminal comprises a cathode tab extension foil 231 of conductive material, e.g. aluminum anode foil having a foil length extending between a first cathode terminal end 231a thereof coupled with the gathered cathode tabs 233 and a second cathode terminal end 231b thereof extending across the ledge 141. The second cathode terminal end 231b extends across the ledge 141 and upper edge 94 and is trapped by the cover 110 as shown in FIG. 28 when the joint between the cover edge and the side wall upper opening edge 94 is formed and welded as described further below. The second terminal end 231b is sealed in the joint when it is formed, and any portion extending to the exterior is trimmed either before or after welding the joint.

Figure 27:
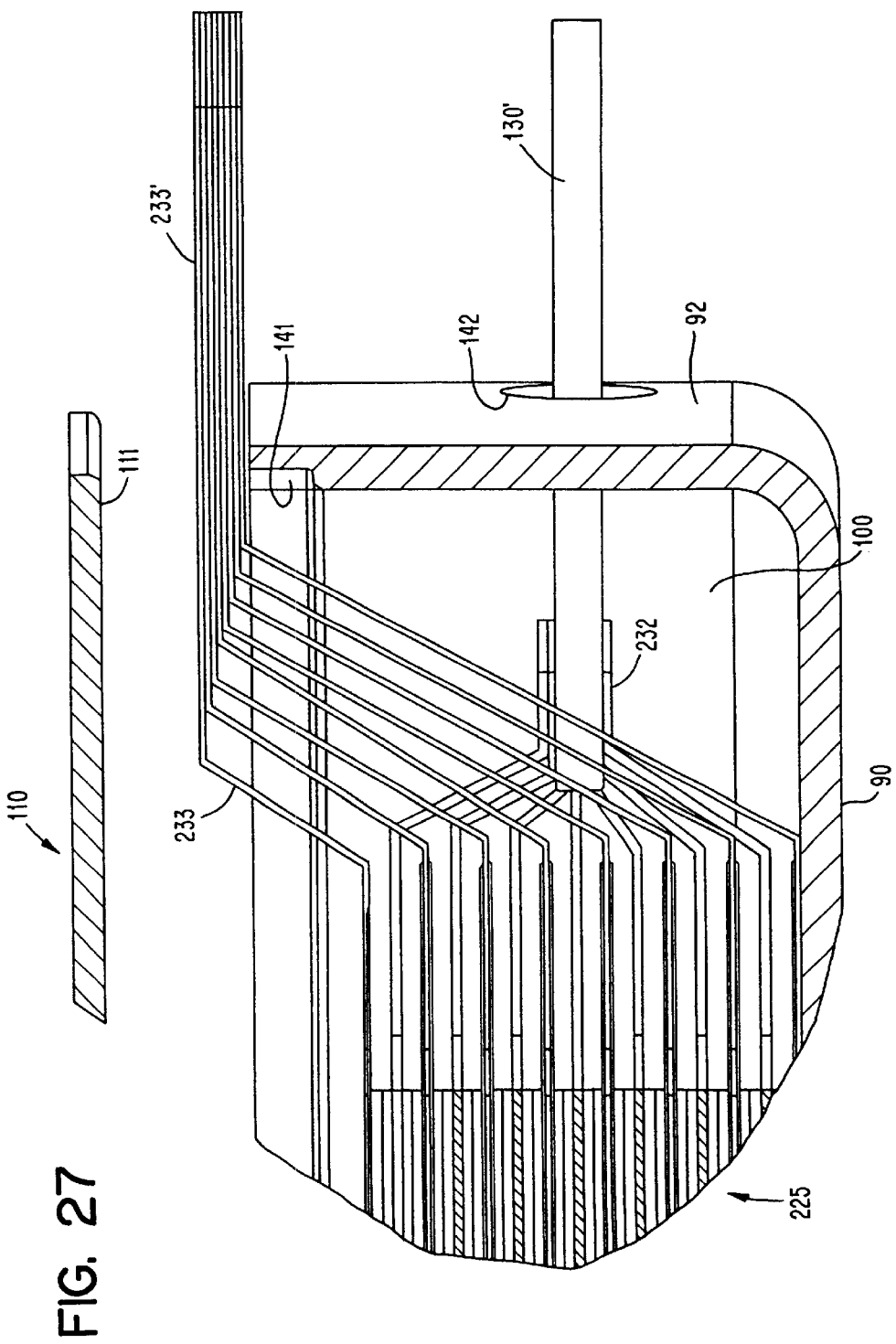
FIG. 27 is a side elevation, cross-section view illustrating a further form of anode and cathode terminals illustrating a stack of cathode tabs trapped between the cover edge and the side wall upper opening edge.
Figure 30:
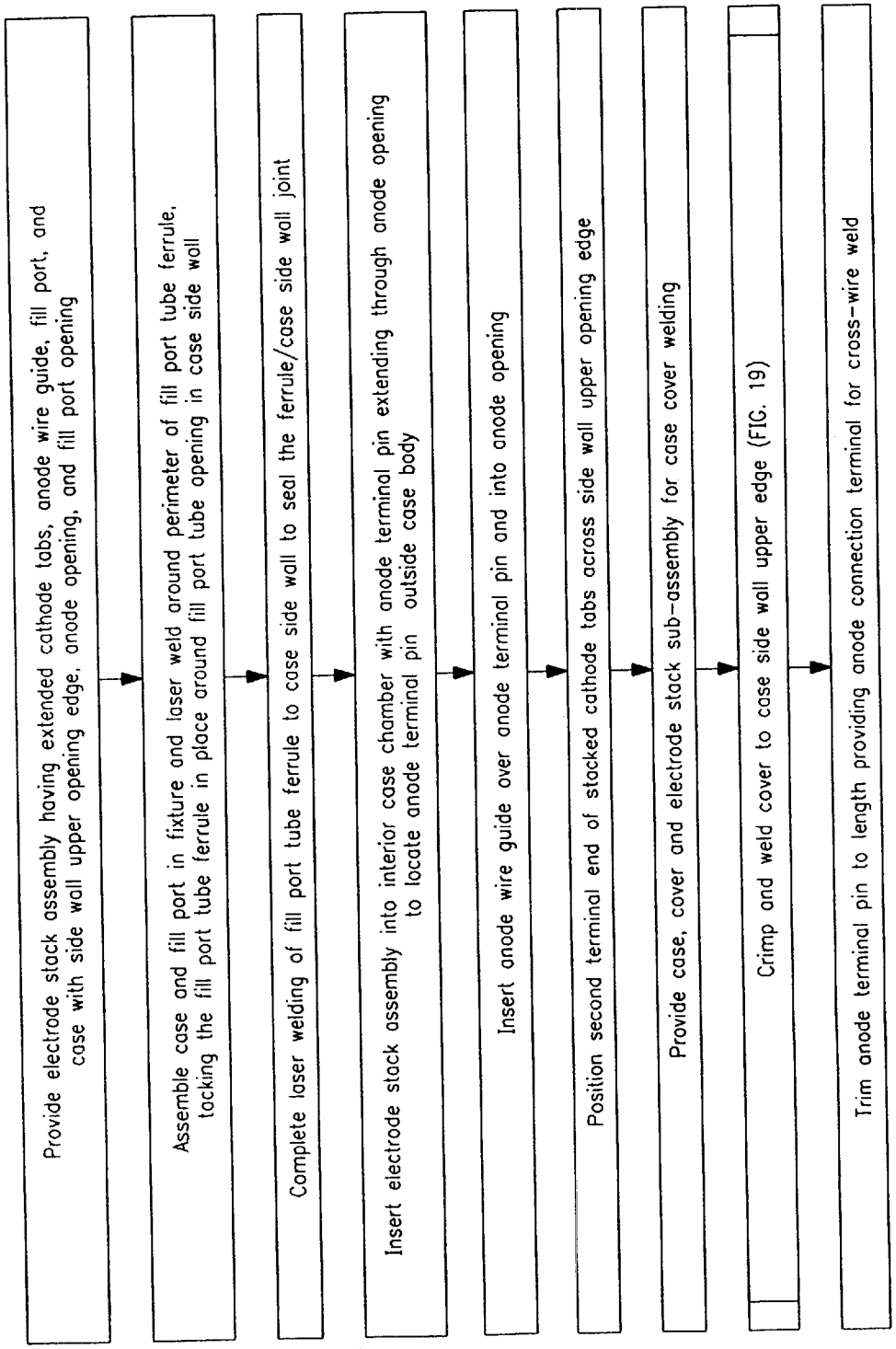
FIG. 30 is a flow chart illustrating the process of making the electrical connections of the cathode terminal illustrated in FIG. 26.

In a further variation of this embodiment illustrated in FIGS. 27 and 30, the cathode terminal comprises an extended length 233' of a plurality or all of the cathode tabs 233 extending from the cathode layers of the electrode stack assembly 225 across the ledge 141. The second cathode terminal ends of the extended cathode tabs 233 have a cathode tab stack thickness about equal to the depth of the relief 111 of FIG. 25 and a tab end width equal to or less than the width of relief 111. The cathode tab stack extends across the ledge 141 and upper edge 94 and is trapped by the cover 110 sealed against the side wall upper opening edge 94 and the cathode tab stack.

It should be noted that the present invention can be employed with the illustrated wiring harness 155 or with equivalent harnesses or connector assemblies. The wire harness 155 may then serve as a means of routing capacitor electrical connections as desired in, for example, device level assembly steps as shown in FIGS. 3(a)–3(g), for example. In the embodiments shown in FIGS. 9–12, 23(b) and 24(b), terminal connector 153 forms the female end of a slide contact adapted to be connected to a mating connector of a circuit or module. In another embodiment, terminal connector 153 may be a male end of a slide contact. Moreover, the wires 151 and 152 may be shortened such that the terminal connector 153 is mechanically bonded to the epoxy droplet connector block 145, 145'. Or the terminal connector 153 can be eliminated so that the ends of the wires 151 and 152 can be connected to other circuits or modules by resistance spot welding, ultrasonic wire bonding, soldering, crimping, or other attachment means.

The remaining capacitor fabrication steps following formation of the epoxy droplet connector block 145, 145' are illustrated in FIG. 13. After the welding steps and the formation of the connector block 145, 145' are completed, capacitor 265 is filled with electrolyte through a fill port 107 welded into a hole in the side wall 92 of the capacitor case, and the fill port lumen is then closed. The filling is accomplished in a plurality of vacuum impregnation cycles described in detail in the above-referenced parent application Ser. No. 09/103,876. The electrolyte may be any suitable liquid electrolyte for high voltage electrolytic capacitors. In a preferred embodiment, the electrolyte is an ethylene glycol based electrolyte having an adipic acid solute. It is contemplated that other electrolytes suitable for use in high voltage capacitors may also be employed.

Fill port 107 provides electrolyte filling and helium leak verification capabilities and is easy to hermetically seal when these functions are completed. The hermeticity of capacitor 265 is preferably measured using a helium leak test that. In one type of helium leak testing, a helium leak testing apparatus forms a seal around fill port 107. It is preferred that an O-ring be disposed between the fitting and the fill port 107 as a vacuum of about 50 Tor is pulled on the interior of capacitor 265 through the fill port tube lumen and the gas pulled from the interior of capacitor 265 is directed past a tuned mass spectrometer. Helium gas is then emitted about and around capacitor 265, cover 110, case 90, the joint between the cover 110 and case 90, connector block 145, ferrule 105, fill port 107 and ferrule 105 and other components while the helium leaktightness testing apparatus tests gas and molecules evacuated from the interior of capacitor 265 for the presence of helium gas which has leaked from the exterior of capacitor 265 into the interior thereof The leak rate for helium through the materials and joints within capacitor 265 is determined by the mass spectrometer. This measure of leaktightness or hermeticity provides a means of assuring the quality of the welded joints of the cover to the case opening, the feedthrough ferrules to the case side wall and the fill tube ferrule to the case side wall.

In another type of helium leak testing, "bombing" or filling of the interior chamber of capacitor 265 with helium gas is accomplished immediately prior to sealing of fill port 107. The exterior of the sealed capacitor 265 is then monitored under vacuum conditions with a tuned mass spectrometer to determine the rate of helium leakage past the materials and joints of capacitor 265.

A tuned mass spectrometer is most preferably included in the helium leaktightness testing apparatus. The spectrometer is sensitive to the presence of helium atoms or molecules. An example of such an apparatus is a LEYBOLD INFICON Model No. UL-200 Helium Leaktester manufactured in East Syracuse, N.Y. An O-ring having a leaktightness rating of about $1 \times 10^{-9}$ cm$^3$/sec. is most preferably employed in conjunction with the fill tube and the fitting of the leaktightness testing apparatus. A typical fail point specification for the leaktightness testing apparatus when employed with the capacitor 265 is about $1 \times 10^{-9}$ cm$^3$/sec.

When hermeticity testing is completed, the fill tube 107 is employed to fill the capacitor case with electrolyte. The capacitor 265 and the electrolyte source are then placed in a vacuum chamber with the exterior tube end 106 of fill port 107 connected to a source of the electrolyte optionally using a temporary fill tube attached thereto. Preferably, multiple vacuum impregnation cycles are then performed at pressures exceeding the vapor pressure of the electrolyte described further below. In a less preferred method, capacitor 265 is filled with electrolyte by immersing capacitor 265 in the electrolyte or by vacuum-filling capacitor 265 with a metered filling machine.

Once capacitor 265 is filled with electrolyte, it is preferred that an aging process be undertaken to form the dielectric aluminum oxide layer. Aging is generally accomplished by applying a current through the capacitor terminals and gradually raising the voltage across those terminals from zero to the peak aging voltage of the capacitor (usually between about 360 and about 390 Volts DC). Once the aging voltage is attained, capacitor 265 is held at that voltage until the leakage current stabilizes at an acceptably low value. It is preferred that capacitor 265 be aged until a voltage of about 370 Volts is attained during a current limiting process.

The aging process is preferably carried out with the voltage set at 370 Volts and the current limited to about 1.5 mA (for capacitor 265 having a capacitance of 214 microfarads) while observing leakage current. It is beneficial to increase the temperature of the aging system at higher voltages. In one preferred method, the temperature is increased to about 70 degrees Celsius when the voltage reaches 230 Volts. After charging to 370 Volts, the capacitors are most preferably permitted to continue aging with the voltage held at 370 Volts until the leakage current decreases to a predetermined value, a predetermined time at 370 Volts has elapsed, or until a predetermined rate of decrease in leakage current has been obtained.

Following aging, post aging vacuum treatment or filling of the capacitor 265 contributes to significant improvements in capacitance and equivalent series resistance (ESR) as described in detail in the above-referenced parent application Ser. No. 09/103,876.

After the aging and vacuum refilling cycles are completed, distal end 106 of fill port tube 107 is hermetically sealed to inhibit the loss of electrolyte, even when gas pressures build up within the capacitor. Preferably the fill port lumen is first crimped shut at the end of fill port tube 107 mechanically by pliers or other suitable means such as compression rollers or welding. The crimped or closed joint so formed is next most preferably trimmed with side cutter metal shears or in a metal die, and sealed. The fill port thereof may be closed and sealed quickly at minimum cost without any requirement for additional high tolerance, expensive piece parts or components for sealing fill tube 197. The gaps in the crimped end of fill port tube 107 are then sealed, most preferably by using joining techniques such as ultrasonic welding, cold welding or laser welding. See, for example, Tables 2 and 3.

But other steps may be undertaken to seal fill port tube 107 including gluing, epoxying, or any other suitable means. For example, the lumen of fill port tube 107 may be sealed by inserting a compression-fit spherical ball into a corresponding spherical recess disposed inside the lumen of fill port tube 107 or ferrule 105. The ball is most preferably formed from a metal, plastic or ceramic material that is stable in the capacitor electrolyte. Dimensional control of the fill port tube or ferrule lumen inside diameter in respect of the diameter of the ball is critical to controlling the quality of the seal being made. Ideally, the ball fits in the inside diameter in as tight an interference fit as possible without damaging the fill port ferrule weld or deforming case 90 to any significant extent. The "ball" need not conform to a spherical geometry, and may be a fitting that is cylindrically, conically or otherwise-shaped.

Still another method for sealing fill port ferrule 105 is to integrate a hydrogen permeable membrane seal into or near to fill port ferrule 105 that does not permit electrolyte components to escape through fill port tube 107 but that does permit hydrogen gas evolved through charge and discharge of capacitor 265 to escape from the interior thereof. By sealing fill port tube 107 with a barrier having sufficient chemical resistance, but that is selective to hydrogen gas (such as some silicones, polyphenylene oxides, cellulose acetates and triacetates and polysulfones), no electrolyte is lost. Several potting adhesives (such as epoxy or silicone) have the foregoing chemical resistance and hydrogen permeability properties and thus are suitable for such use. Those adhesives most preferably seal feedthroughs while permitting hydrogen gas to escape from otherwise hermetically sealed capacitor 265. Alternatively, the sealing of fill port tube 107 can be accomplished by an adhesive strip disposed over distal end 106 of fill port tube 107, similar to the types of seals employed in commercial ethylene glycol coolant canisters.

Once the fill port tube lumen is sealed by one of the means and methods described above, the capacitor 265, 265', 265" is electrically tested. Applications in implantable defibrillators may require two capacitors 265, 265', 265" to be connected in series. In this embodiment, an insulator is provided by a two sided adhesive being disposed between the capacitors 265, 265', 265" so that they are joined along opposing faces with the insulator/adhesive strip disposed therebetween. The pair of capacitors 265, 265', 265" is then provided for assembly in ICD IPG 10 as shown and described above with respect to FIGS. 3(a) through 3(g).

In the case negative electrolytic capacitor embodiments of the invention described herein, the cathode layers have cathode layer edges that may be in electrical contact with the interior case side wall.

Although only a few exemplary embodiments of a capacitor 265, 265', 265" in which the present invention is advantageously implemented have been described in detail above, those skilled in the art will appreciate readily that many modifications are possible in the exemplary embodiments without materially departing from the novel teachings and advantages of the invention. Accordingly, all such modifications are intended to be included within the scope of the present invention as defined in the following claims.

The preceding specific embodiments are illustrative of a capacitor structure and method of fabrication thereof and its incorporation into an IMD in accordance with the present invention. It is to be understood, therefore, that other expedients known to those skilled in the art or disclosed herein, and existing prior to the filing date of this application or coming into existence at a later time may be employed without departing from the invention or the scope of the appended claims. In the claims, means-plus-function clauses are intended to cover the structures described herein as performing the recited function and not only structural equivalents but also equivalent structures.

All patents and printed publications disclosed herein are hereby incorporated by reference herein into the specification hereof, each in its respective entirety.

We claim:

1. A method of fabricating an electrolytic capacitor comprising:

providing a capacitor case defining an interior case chamber bounded by a case wall, the case further comprising a case base with a case side wall extending from the case base to a side wall upper opening edge and a cover adapted to be hermetically sealed at a cover edge against the side wall upper opening edge to enclose the interior case chamber;

forming an anode terminal passageway through said case wall;

forming a cathode terminal passageway through said case wall;

forming an electrode stack assembly adapted to be located within the interior case chamber, the electrode stack assembly further comprising a plurality of capacitor layers stacked in registration upon one another, each capacitor layer comprising a cathode layer having a cathode tab, an anode sub-assembly comprising at least one anode layer having an anode tab, and a separator layer located between adjacent anode and cathode layers, whereby all adjacent cathode layers and anode layers of the stack are electrically insulated from one another by a separator layer;

providing an anode terminal;

coupling a first anode terminal end of an anode terminal electrically and mechanically with a plurality of said anode tabs;

extending a second anode terminal end of said anode terminal through said anode terminal passageway;

supporting said anode terminal extending through said anode terminal passageway while electrically insulating said anode terminal from said case wall thereby locating an anode connection terminal at said second anode terminal end exterior to said case wall;

providing a cathode terminal;

coupling a first cathode terminal end of a cathode terminal electrically and mechanically with a plurality of said cathode tabs extending a second cathode terminal end of said cathode terminal through said cathode terminal passageway;

electrically and mechanically sealing said cathode terminal into said cathode terminal passageway to seal said cathode terminal passageway thereby making electrical connection of said cathode tabs with said case wail and providing a cathode connection terminal at or coupled to the exterior surface of the case wall; and attaching a connector assembly to said anode connection terminal to make electrical connection with said anode tabs and to said cathode connection terminal to make electrical connection with said cathode tabs.

2. The method of claim 1, further comprising the step of:

forming a connector block against said capacitor case to cover and electrically insulate said exposed anode and cathode connection terminals and the connector assemble coupled thereto.

3. The method of claim 2, wherein the step of electrically coupling a connector assembly to said anode and cathode connection terminals further comprises:

cross-wire welding an exposed anode wire end of an anode lead wire of the wiring harness to said anode connection terminal at said second anode terminal end; and cross-wire welding an exposed cathode wire end of a cathode lead wire of the wiring harness to said cathode connection terminal at said second cathode terminal end.

4. The method of claim 2, wherein the step of electrically coupling a connector assembly to said anode and cathode connection terminals further comprises:

cross-wire welding an exposed anode wire end of an anode lead wire of the wiring harness to said anode connection terminal at said second anode terminal end;

grinding the second cathode terminal end flush with the case wall at the cathode connection terminal; and surface welding an exposed cathode wire end of a cathode lead wire of the wiring harness to said cathode connection terminal on the exterior case wall.

5. The method of claim 1, wherein the step of electrically coupling a connector assembly to said anode and cathode connection terminals further comprises:

cross-wire welding an exposed anode wire end of an anode lead wire of the wiring harness to said anode connection terminal at said second anode terminal end;

grinding the second cathode terminal end flush with the case wall at the cathode connection terminal; and surface welding an exposed cathode wire end of a cathode lead wire of the wiring harness to said cathode connection terminal on the exterior case wall.

6. The method of claim 1, wherein the step of electrically coupling a connector assembly to said anode and cathode connection terminals further comprises:

cross-wire welding an exposed anode wire end of an anode lead wire of the wiring harness to said anode connection terminal at said second anode terminal end; and cross-wire welding an exposed cathode wire end of a cathode lead wire of the wiring harness to said cathode connection terminal at said second cathode terminal end.

7. The method of claim 1, wherein:

the step of forming a cathode terminal passageway through said case wall comprises defining a cathode terminal passageway between a portion of the cover edge and the side wall upper opening edge;

the step of providing a cathode terminal comprises providing a cathode tab extension foil of conductive material having a foil length and foil width, a first cathode terminal end and a second cathode terminal end; and the step of electrically and mechanically sealing said cathode terminal into said cathode terminal passageway to seal said cathode terminal passageway thereby making electrical connection of said cathode tabs with said case wall and providing a cathode connection terminal at or coupled to the exterior surface of the case wall comprises sealing the second cathode terminal end of the cathode tab extension foil between a portion of the cover edge and the side wall upper opening edge.

8. The method of claim 7, wherein the step of providing a capacitor case further comprises forming a relief in the case cover edge to receive said second cathode terminal end extending across said side wall upper opening edge and trapped there by the relieved portion of the cover edge.

9. The method of claim 7, wherein the step of electrically coupling a connector assembly to said anode and cathode connection terminals further comprises:

cross-wire welding an exposed anode wire end of an anode lead wire of the wiring harness to said anode connection terminal at said second anode terminal end; and surface welding an exposed cathode wire end of a cathode lead wire of the wiring harness to said cathode connection terminal on the exterior case wall.

10. The method of claim 7, further comprising the step of:

forming a connector block against said capacitor case to cover and electrically insulate said exposed anode and cathode connection terminals and the connector assemble coupled thereto.

11. The method of claim 1, wherein:

the step of forming a cathode terminal passageway through said case wall comprises defining a cathode terminal passageway between a portion of the cover edge and the side wall upper opening edge;

the step of providing a cathode terminal comprises providing cathode tab extensions of the cathode tabs having a tab length and tab width, a first cathode terminal end and a second cathode terminal end; and the step of electrically and mechanically sealing said cathode terminal into said cathode terminal passageway to seal said cathode terminal passageway thereby making electrical connection of said cathode tabs with said case wall and providing a cathode connection terminal at or coupled to the exterior surface of the case wall comprises sealing at least one of the second cathode terminal ends of the cathode tabs between a portion of the cover edge and the side wall upper opening edge.

12. The method of claim 11, wherein the step of providing a capacitor case further comprises forming a relief in the case cover edge to receive said second cathode terminal end extending across said side wall upper opening edge and trapped there by the relieved portion of the cover edge.

13. The method of claim 11, wherein the step of electrically coupling a connector assembly to said anode and cathode connection terminals further comprises:

cross-wire welding an exposed anode wire end of an anode lead wire of the wiring harness to said anode connection terminal at said second anode terminal end; and surface welding an exposed cathode wire end of a cathode lead wire of the wiring harness to said cathode connection terminal on the exterior case wall.

14. The method of claim 11, further comprising the step of:

forming a connector block against said capacitor case to cover and electrically insulate said exposed anode and cathode connection terminals and the connector assemble coupled thereto.

\* \* \* \* \*

UNITED STATES PATENT AND TRADEMARK OFFICE
CERTIFICATE OF CORRECTION

PATENT NO. : 6,402,793 B1
DATED : June 11, 2002
INVENTOR(S) : Thomas P. Miltich et al.

It is certified that error appears in the above-identified patent and that said Letters Patent is hereby corrected as shown below:

<u>Title page,</u>
Item [54], delete entire title and replace it with -- METHOD OF MAKING A FLAT ELECTROLYTIC CAPACITOR WITH CATHODE/CASE ELECTRICAL CONNECTIONS FOR USE IN IMPLANTABLE MEDICAL DEVICE --.
Item [57], ABSTRACT, delete entire ABSTRACT and replace it with --A method for making flat electrolytic capacitors particularly for use in implantable medical devices is characterized by forming a stack of cathode and anode layers each having a tab, forming an anode and a cathode terminal passageways through the capacitor case wall, extending an anode terminal through the anode passageway to connect the anode tabs with a connector assembly located outside the case, extending a cathode terminal through the cathode passageway to connect cathode tabs with the exterior surface of the case and to the connector assembly. The cathode terminal passageway comprises a cathode opening extending through the case wall and the cathode terminal comprises a cathode wire or feedthrough pin extending from gathered cathode tabs into or through the cathode opening providing the cathode connection terminal electrically connected with the case. Alternatively, the cathode terminal passageway comprises a portion of an interior ledge of the side wall upper opening edge having a width and a depth depressed below the upper opening edge and a cover edge portion overlying the ledge to trap the cathode terminal when the cover is welded to the crimped upper edge--.

<u>Column 35,</u>
Line 46, delete "wail" and insert -- wall --.
Line 55, delete "exposed."
Line 57, delete "assemble" and insert -- assembly --.
Line 58, delete "electrically coupling" and insert -- attaching --.
Line 62, delete "the wiring" and insert -- a wiring --.

<u>Column 36,</u>
Lines 5, 16, 27 and 61, delete "electrically."
Lines 6, 17, 28 and 62, delete "coupling" and insert -- attaching --.
Lines 9, 20, 31 and 65, delete "the wiring" and insert -- a wiring --.
Lines 15 and 26, before "case" insert -- surface of the --.
Line 60, delete "relieved portion" and insert -- relief --.

UNITED STATES PATENT AND TRADEMARK OFFICE
CERTIFICATE OF CORRECTION

PATENT NO.     : 6,402,793 B1
DATED          : June 11, 2002
INVENTOR(S)    : Thomas P. Miltich et al.

It is certified that error appears in the above-identified patent and that said Letters Patent is hereby corrected as shown below:

Column 37,
Line 3, before "case" insert -- surface of the --.
Line 6, delete "exposed."
Line 8, delete "assemble" and insert -- assembly --.
Line 15, before "tab" insert -- a --.

Column 38,
Line 7, delete "relieved portion" and insert -- relief --.
Lines 8-9, delete "electrically coupling" and insert -- attaching --.
Line 12, delete "the wiring" and insert -- a wiring --.
Line 17, before "case" insert -- surface of the --.
Line 21, delete "exposed."
Line 23, delete "assemble" and insert -- assembly --.

Signed and Sealed this

Eighth Day of April, 2003

JAMES E. ROGAN
*Director of the United States Patent and Trademark Office*